United States Patent
Kondou et al.

(10) Patent No.: US 8,435,013 B2
(45) Date of Patent: May 7, 2013

(54) RECIPROCATING COMPRESSOR AND OXYGEN CONCENTRATOR

(75) Inventors: Keita Kondou, Settsu (JP); Satoshi Ueda, Settsu (JP); Yuki Kuwamura, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 757 days.

(21) Appl. No.: 12/526,453

(22) PCT Filed: Feb. 8, 2008

(86) PCT No.: PCT/JP2008/052194
§ 371 (c)(1),
(2), (4) Date: Aug. 7, 2009

(87) PCT Pub. No.: WO2008/096874
PCT Pub. Date: Aug. 14, 2008

(65) Prior Publication Data
US 2010/0319547 A1    Dec. 23, 2010

(30) Foreign Application Priority Data

Feb. 9, 2007 (JP) .................... 2007-030471
Feb. 9, 2007 (JP) .................... 2007-030473
Jul. 25, 2007 (JP) .................... 2007-192792

(51) Int. Cl.
*F04B 1/04* (2006.01)
*F04B 27/04* (2006.01)

(52) U.S. Cl.
USPC ............... 417/273; 417/269; 417/271

(58) Field of Classification Search .......... 417/269, 417/271, 273, 902; 92/240
See application file for complete search history.

(56) References Cited

U.S. PATENT DOCUMENTS

| | | | | |
|---|---|---|---|---|
| 1,820,883 A * | 8/1931 | Hueber | ........... | 417/273 |
| 2,752,088 A * | 6/1956 | Borgerd et al. | ........... | 417/419 |
| 3,248,044 A * | 4/1966 | Parker | ........... | 417/372 |
| 3,334,808 A * | 8/1967 | Parker et al. | ........... | 417/372 |
| 3,807,907 A * | 4/1974 | Gannaway | ........... | 417/415 |
| 4,057,979 A * | 11/1977 | Abell et al. | ........... | 62/469 |
| 4,470,772 A * | 9/1984 | Gannaway | ........... | 417/368 |
| 5,288,211 A * | 2/1994 | Fry | ........... | 417/312 |
| 5,584,675 A * | 12/1996 | Steurer et al. | ........... | 417/372 |

FOREIGN PATENT DOCUMENTS

| | | |
|---|---|---|
| JP | 58-176484 A | 10/1983 |
| JP | 2-64274 A | 3/1990 |
| JP | 2001-271744 A | 10/2001 |
| JP | 2003-222077 A | 8/2003 |

(Continued)

OTHER PUBLICATIONS

Notice of Reasons for Rejection of corresponding Japanese Application No. 2007-030471 dated Mar. 25, 2008.

(Continued)

*Primary Examiner* — Peter J Bertheaud
(74) *Attorney, Agent, or Firm* — Global IP Counselors

(57) ABSTRACT

A reciprocating compressor includes a motor having a motor shaft, four cylinders provided in perpendicular directions relative to an axial direction of the motor shaft, and four pistons Each piston has a piston head part and a rod part formed integrally with the piston head part. Each piston head part is fitted into one of the four cylinders in a reciprocable fashion. Each rod part is rotatably mounted to an eccentric shaft that is fixed to the motor shaft.

27 Claims, 41 Drawing Sheets

FOREIGN PATENT DOCUMENTS

| | | |
|---|---|---|
| JP | 2004-92638 A | 3/2004 |
| JP | 2004-211708 A | 7/2004 |
| JP | 2004-293319 A | 10/2004 |
| JP | 2005-23788 A | 1/2005 |
| JP | 2005-245926 A | 9/2005 |

OTHER PUBLICATIONS

Notice of Reasons for Rejection of corresponding Japanese Application No. 2007-030473 dated Apr. 1, 2008.

Notice of Reasons for Rejetion of corresponding Japanese Application No. 2007-192792 dated Mar. 25, 2008.

Notice of Reasons for Rejetion of corresponding Japanese Application No. 2007-192792 dated Nov. 18, 2008.

Notice of Reasons for Rejetion of corresponding Japanese Application No. 2007-192792 dated Jun. 16, 2009.

Chinese Office Action of corresponding Chinese Application No. 200880004474.6 dated Feb. 23, 2011.

* cited by examiner

DIRECTION OF MOTOR SHAFT

CROSS SECTIONAL VIEW ALONG B-B LINE

FIG.15 (a)
FIG.15 (b)
CROSS SECTIONAL VIEW ALONG N-N LINE
FIG.15 (c)
CROSS SECTIONAL VIEW ALONG M-M LINE
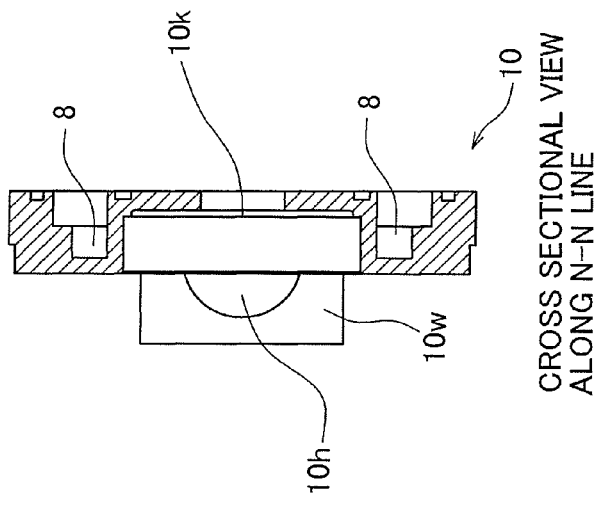
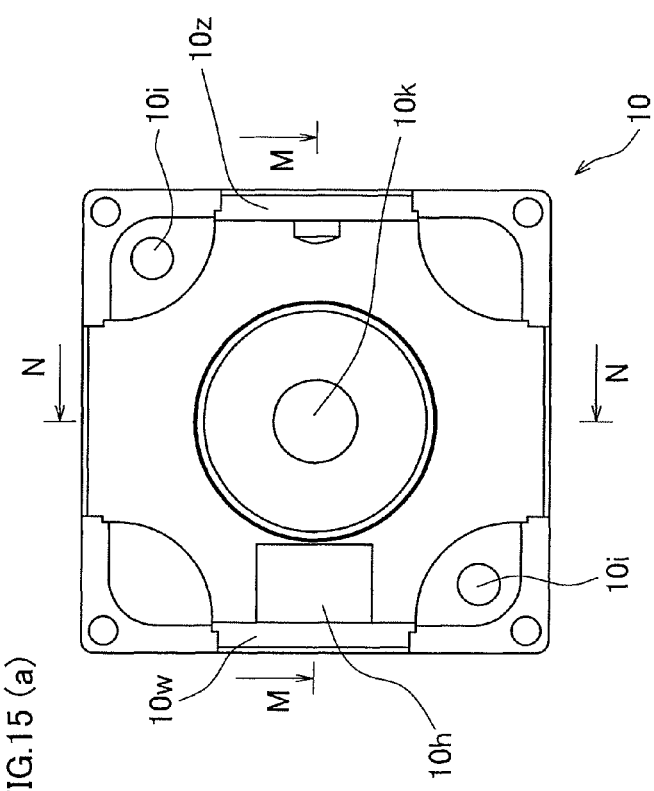
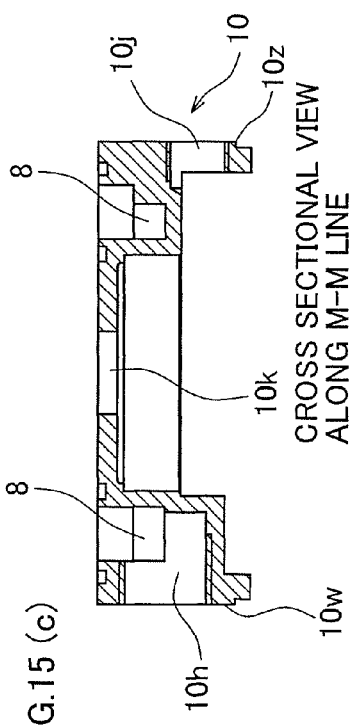

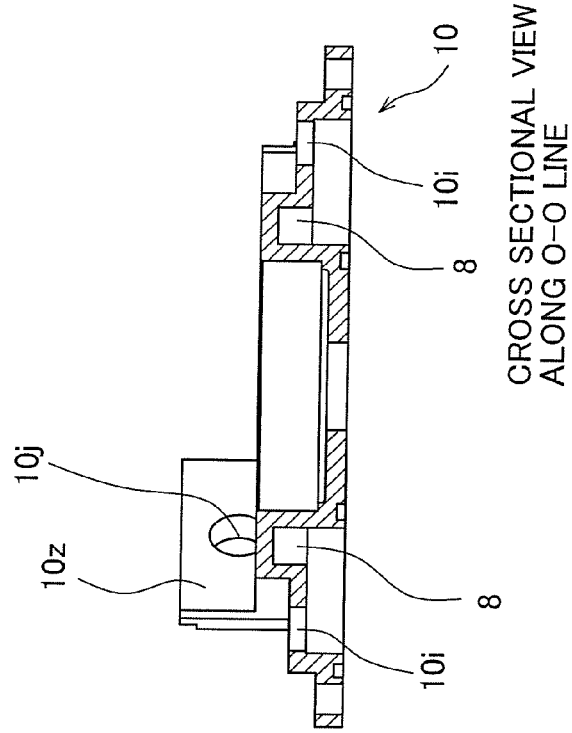
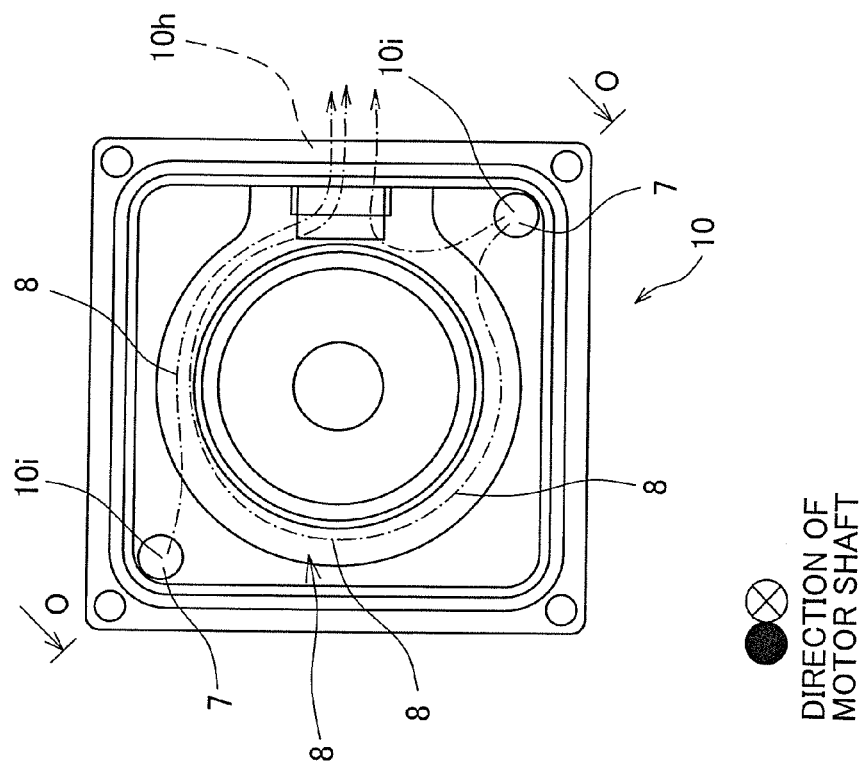

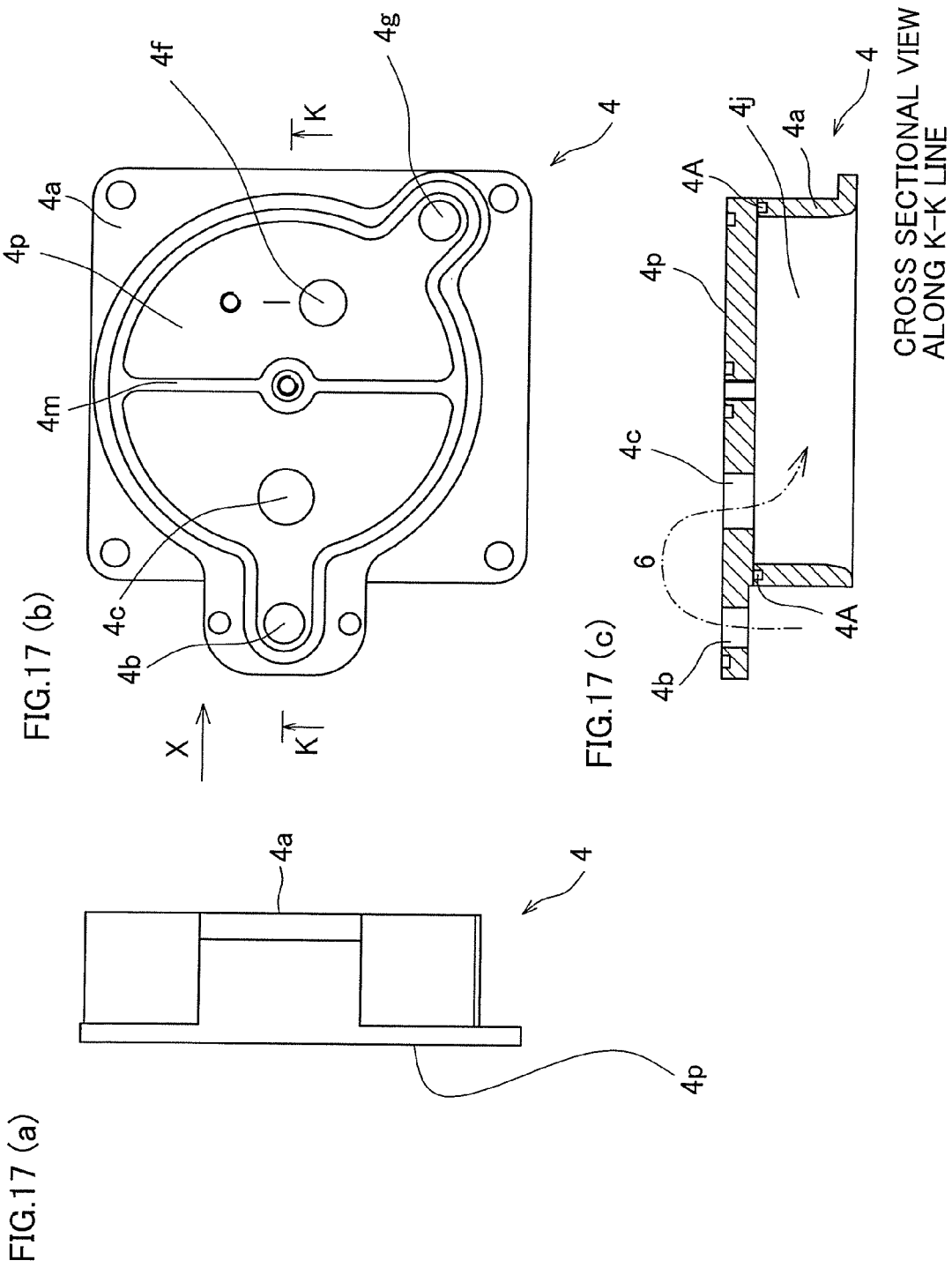

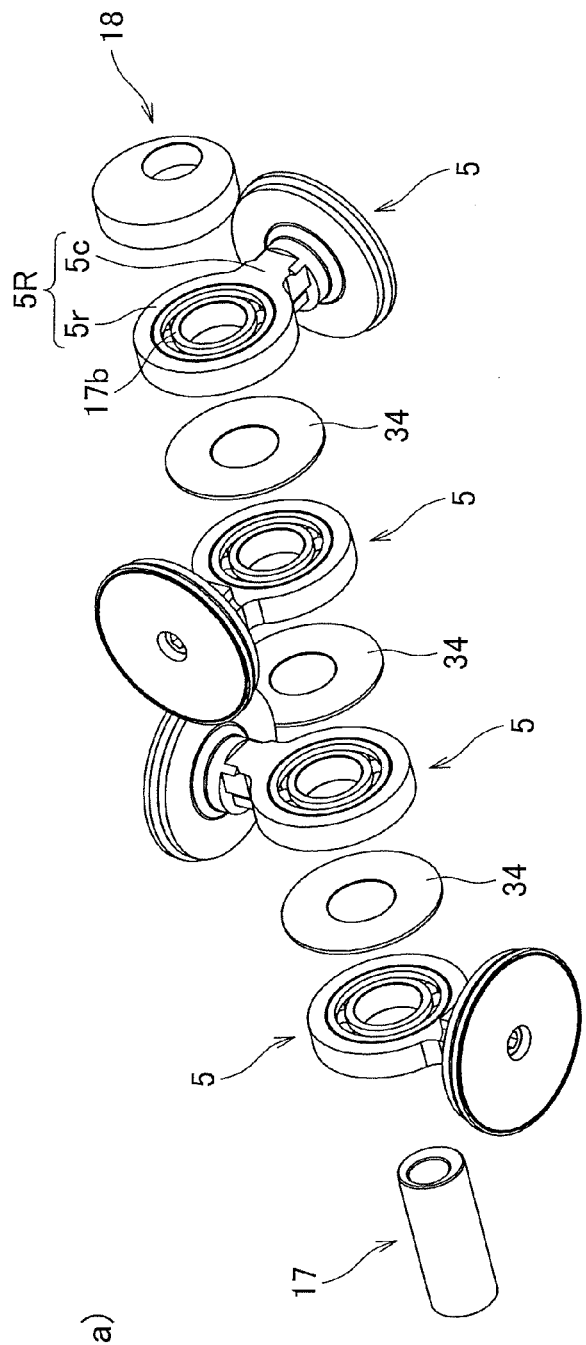
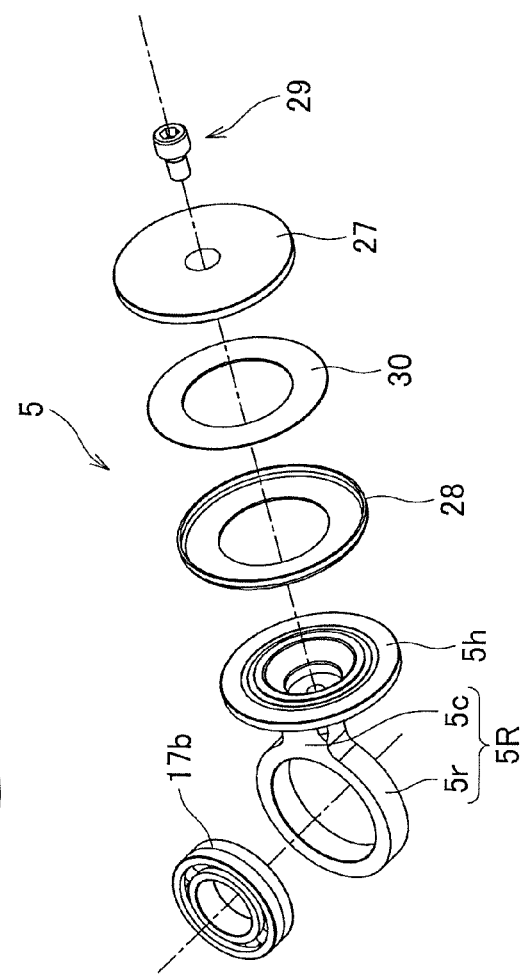
FIG.21 (a)
FIG.21 (b)

CROSS SECTIONAL VIEW
ALONG Q-Q LINE

CROSS SECTIONAL VIEW ALONG R-R LINE

CROSS SECTIONAL VIEW ALONG S-S LINE

RELATION AMONG ROTATION ANGLE, PV VALUE, AND
INCLINATION OF HEAD WHEN PISTON IS INCLINED AT 1.5 ANGLE

RECIPROCATING COMPRESSOR AND OXYGEN CONCENTRATOR

CROSS-REFERENCE TO RELATED APPLICATIONS

This U.S. National stage application claims priority under 35 U.S.C. §119(a) to Japanese Patent Application Nos. 2007-030471, filed in Japan on Feb. 9, 2007, 2007-030473, filed in Japan on Feb. 9, 2007, and 2007-192792, filed in Japan on Jul. 25, 2007, the entire contents of which are hereby incorporated herein by reference.

TECHNICAL FIELD

The present invention relates to a reciprocating compressor having four cylinders, and an oxygen concentrator incorporating the reciprocating compressor.

BACKGROUND ART

Japanese Unexamined Patent Publication No. 2004-211708 discloses an example of a compact piston pump utilized for a known oxygen concentrator or the like. The pump disclosed in Japanese Unexamined Patent Publication No. 2004-211708 is a two-headed reciprocating compressor having two cylinders. The pump includes: a motor having a drive shaft (motor shaft); two cylinders provided in a direction perpendicular to an axial direction of the drive shaft; and two pistons each having a piston head part and a rod part formed integrally, the piston head part fitting into a corresponding one of the two cylinders in a reciprocable fashion, and the rod part being rotatably installed to an eccentric shaft fixed to the motor shaft. In the two-headed reciprocating compressor, the piston head part of each of the two pistons makes intake-compression strokes in a compression chamber in the corresponding one of the cylinders, maintaining a 180-degree phase difference with each other.

SUMMARY OF THE INVENTION

Problems to be Solved by the Invention

In the two-headed reciprocating compressor of Japanese Unexamined Patent Publication No. 2004-211708, a small compressor without performance loss: specifically, a smaller piston rod 5P maintaining rotation speed and exhaust flow rate, would cause the following problem: Due to a larger angle of oscillation θ (see FIG. 28(a)), airtightness of a compression chamber is barely ensured. Further, a larger angle of oscillation of a piston leads to a larger sliding distance of the piston head part of the piston. This contributes to premature wear of a seal member attached to the piston head part, thus resulting in a shorter product life.

Thus, an object of the present invention is to provide a smaller and lighter reciprocating compressor with higher efficiency and longer life time, producing lower noise and less vibration, and an oxygen concentrator incorporating the reciprocating compressor.

SUMMARY OF THE INVENTION

The reciprocating compressor according to a first aspect of the present invention includes: a motor having a motor shaft; four cylinders provided in directions perpendicular to an axial direction of the motor shaft; four pistons each having a piston head part and a rod part formed integrally, the piston head part fitting into one of the cylinders in a reciprocable fashion, and the rod part being rotatably installed to an eccentric shaft fixed to the motor shaft.

In the reciprocating compressor, the number of cylinders is increased from two to four. This allows a shorter stroke while maintaining rotation speed of each piston and a total exhaust flow rate. Thus, an angle of oscillation of each piston is maintained despite a shorter piston rod. This realizes a compact compressor with airtightness of a compression chamber. Further, a smaller stroke leads to a shorter oscillation distance of the piston head part, thus ensuring sealing ability of a seal member for a long time, the seal member being provided to the piston head part. Further, the four cylinders greatly expand heat dissipating surfaces. This restrains a temperature rise in a compression chamber, thus greatly improving compression efficiency.

A reciprocating compressor according to a second aspect of the present invention is the reciprocating compressor according to the first aspect of the present invention, where the four cylinders consist of two cylinders provided on one straight line passing through a center of the motor shaft, and the other two cylinders provided on another straight line which is perpendicular to the one straight line and passes through the center of the motor shaft.

In plan view, the reciprocating compressor is provided with two cylinders on one straight line passing through the center of the motor shaft, and the other two cylinders on another straight line which is perpendicular to the one straight line and passes through the center of the motor shaft. This allows a smaller gap between two circumferentially adjacent cylinders. Further, interference is less likely caused between the piston head parts of two adjacent pistons. This allows an even shorter piston rod. Accordingly, an even smaller compressor is realized.

A reciprocating compressor according to a third aspect of the present invention is the reciprocating compressor according to the first or second aspect of the present invention, where the piston head parts of the four pistons make intake-compression strokes while maintaining a ninety-degree phase difference with each other.

In the reciprocating compressor, the four pistons each make intake-compression strokes while maintaining a ninety-degree phase difference with each other. This balances out force acting on the piston head part of each the four pistons, thus preventing fluctuations in running torque of the motor shaft. This greatly improves the compression efficiency. Further, intake-exhaust sounds generated from four compression chambers are balanced out, which results in lower noise and less vibration.

A reciprocating compressor according to a fourth aspect of the present invention is the reciprocating compressor according to any one of the first to third aspects of the present invention, where the number of eccentric shaft provided is one.

The reciprocating compressor is provided with one eccentric shaft to which the four pistons are installed. This allows smaller gaps between the rod parts of the pistons in the direction of the motor shaft. Further, a force generated when one piston shifts from a compression stroke to an intake stroke is efficiently transmitted as a force assisting a motion of another piston, thus exhibiting smaller loss in transmission of force. This further improves the compression efficiency.

A reciprocating compressor according to a fifth aspect of the present invention, which is the reciprocating compressor according to any one of the first to fourth aspects of the present invention, includes a casing which accommodates the motor shaft. The casing is provided with first positioning parts. The four cylinders are each provided with a second positioning part corresponding to one of the first positioning parts. The four cylinders are each positioned with respect to the casing by the second positioning part and corresponding one of the first positioning parts in such a way that the axial center of each of the four cylinders matches the axial center of the piston head part of the corresponding one of the four pistons.

In the reciprocating compressor, the casing is provided with the first positioning parts, and the four cylinders are each provided with a second positioning part corresponding to one of the first positioning parts. This allows positioning of the four cylinders with respect to the casing in such a way that the axial center of each of the four cylinders matches the axial center of the piston head part of the corresponding piston. Thus, lopsided wear of each seal member is prevented.

A reciprocating compressor according to a sixth aspect of the present invention, which is the reciprocating compressor according to any one of the first to fifth aspects of the present invention, includes adjust members each provided between neighboring ones of the piston rod parts of the four pistons in the axial direction of the motor shaft, in order to adjust positions of the pistons.

In the reciprocating compressor, the adjust members allow adjustment of positions of the rod parts, which adjust members are each provided between neighboring ones of the rod parts of the four pistons in the axial direction of the motor shaft. This allows an ensured match of the axial center of the cylinder and the axial center of the piston head part, thus preventing lopsided wear of the seal member.

A reciprocating compressor according to a seventh aspect of the present invention, is the reciprocating compressor according to any one of the first to sixth aspects of the present invention, where the four cylinders each include a cylindrical main body part and a sheet plane member. The cylindrical main body part is provided in an axial direction of the cylinder. The sheet plane member is fixed to an end of the main body part by a bolt. The main body part and the plane member have an elastic member provided therebetween.

In the reciprocating compressor, the main body part and the plane member of each of the four cylinders have an elastic member therebetween. This allows a smaller gap between the cylinder and the piston head part of each of the four pistons at a top dead center, merely with torque management of a bolt fastening the plane member to the main body part. This accordingly stabilizes performance of the compressor, thus further improving the compression efficiency.

The reciprocating compressor according to an eighth aspect of the present invention is the reciprocating compressor according to any one of the first to seventh aspects of the present invention, where each of the piston head parts and a retainer plate fixed to the piston head part by a bolt have an elastic spacer therebetween.

In the reciprocating compressor, the spacer provided between the piston head part and the retainer plate of each of the four pistons allows a smaller gap between the cylinder and the piston head part at a top dead center, merely with torque management of a bolt fastening the retainer plate to the piston head part. This stabilizes performance of the compressor, thus further improving the compression efficiency.

A reciprocating compressor according to a ninth aspect of the present invention, which is the reciprocating compressor according to any one of the first to eighth aspects of the present invention, includes: a casing which accommodates the motor shaft; a plurality of intake passages each connected to inside of one of the four cylinders, which intake passages each allow a fluid to pass therethrough; a plurality of exhaust passages each connected to inside of one of the four cylinders, which exhaust passages each allow a fluid to pass therethrough; and at least one of a shared intake passage and a shared exhaust passage, the shared intake passage uniting the intake passages, and the shared exhaust passage uniting the exhaust passages. At least one of the shared intake passage and the shared exhaust passage is provided overlapping at least one of an axial region extending in an axial direction of the motor shaft and a peripheral region thereof.

In the reciprocating compressor, passages between the cylinders are united with at least one of the shared intake passage and the shared exhaust passage. Further, at least one of the shared intake passage and the shared exhaust passage is provided overlapping at least one of the axial region extending in the axial direction of the motor shaft and the peripheral region thereof. This avoids a large compressor as a whole due to the shared passages. As a result, the passages between a plurality of cylinders are united while avoiding a large compressor.

To "overlap" here means that the shared intake passage or the shared exhaust passage is provided so as to fall within a region composed of the axial region and the peripheral region.

A reciprocating compressor according to a tenth aspect of the present invention is the reciprocating compressor according to the ninth aspect of the present invention, where at least one of the shared intake passage and the shared exhaust passage is an annular passage around the axial region.

A shared passage of the reciprocating compressor is annular. This allows a compact assembly of the passages, thus easily avoiding a large compressor. Particularly, the annular shared exhaust passage ensures a sufficient heat dissipating surface of the fluid, thus improving the compression efficiency.

A reciprocating compressor according to an eleventh aspect of the present invention is the reciprocating compressor according to the tenth aspect of the present invention, where the annular shared passage extends two-dimensionally along a plane perpendicular to the axial direction of the motor shaft.

The reciprocating compressor easily ensures a sufficient heat dissipating surface of the fluid while avoiding a large compressor.

A reciprocating compressor according to a twelfth aspect of the present invention, which is the reciprocating compressor according to the tenth or eleventh aspect of the present invention, includes a bearing support member provided to a shaft end portion of the motor shaft. The bearing support member is provided with at least one of the shared exhaust passage and the shared intake passage.

The reciprocating compressor efficiently utilizes the member for bearing support and a peripheral space thereof to unite the passages between the cylinders while efficiently avoiding a large compressor.

A reciprocating compressor according to a thirteenth aspect of the present invention is the reciprocating compressor according to any one of the ninth to twelfth aspects of the present invention, where the exhaust passages each include a first parallel portion extending in the axial direction of the motor shaft.

The exhaust passages each include a part extending in the axial direction of the motor shaft. This allows an efficient arrangement of the exhaust passages in the reciprocating compressor.

A reciprocating compressor according to a fourteenth aspect of the present invention is the reciprocating compressor according to the thirteenth aspect of the present invention, where the first parallel portions are formed inside the casing.

Due to the first parallel portions formed inside the casing, the reciprocating compressor requires fewer or no additional members such as a pipe for passage formation. This decreases the number of members and thus achieves a more efficient arrangement of the exhaust passages, while avoiding a large compressor. Further, the casing itself serves as a heat dissipating member. This greatly expands the heat dissipating surface, thus further improving the compression efficiency.

Note that passages are normally formed inside a reinforce portion serving as a frame of the casing. This allows efficient utilization of the casing while ensuring a function of the casing.

A reciprocating compressor according to a fifteenth aspect of the present invention, which is the reciprocating compressor according to any one of the ninth to eleventh aspects of the present invention, where the motor includes a main body part, and the shared intake passage and the shared exhaust passage are each provided to sandwich the four cylinders. One of the shared intake passage and the shared exhaust passage is provided to a shaft end portion side of the motor shaft, and the other to a main body side of the motor shaft.

In the reciprocating compressor, the shared intake passage and the shared exhaust passage are both arranged efficiently, while avoiding a large compressor. Further, the shared intake passage and the shared exhaust passage are separated. This prevents heat transfer between the shared intake passage and the shared exhaust passage, thus further improving the compression efficiency.

A reciprocating compressor according to a sixteenth aspect of the present invention is the reciprocating compressor according to any one of the ninth to fifteenth aspects of the present invention, where the intake passages each include a second parallel portion extending in the axial direction of the motor shaft.

The intake passages each include apart extending in the axial direction of the motor shaft. This allows an efficient arrangement of the intake passages in the reciprocating compressor.

A reciprocating compressor according to a seventeenth aspect of the present invention is the reciprocating compressor according to any one of the reciprocating compressor according to the ninth to sixteenth aspects of the present invention, where the casing includes a first member and a second member. The exhaust passages pass through inside the first member, and the intake passages pass through inside the second member. The first member and the second member are separate members. The first member has higher thermal conductivity than the second member.

The intake passages and the exhaust passages are respectively provided to the second member and the first member. Further, the first member and the second member have different thermal conductivities. This prevents heat of the exhaust passages from transferring to the intake passages, thus further increasing the compression efficiency.

A reciprocating compressor according to an eighteenth aspect of the present invention is the reciprocating compressor according to any one of the ninth to sixteenth aspects of the present invention, where the exhaust passages each include a first parallel portion extending in the axial direction of the motor shaft, and the intake passages each include a second parallel portion extending in the axial direction of the motor shaft. The casing is provided with a pair of first parallel portions and a pair of second parallel portions therein. The pair of first parallel portions are provided facing each other across the motor shaft, and the pair of second parallel portions are provided facing each other across the motor shaft.

The reciprocating compressor has both the first parallel portions of the exhaust passages and the second parallel portions of the intake passages inside the casing. This facilitates efficient utilization of the casing, thus more efficiently avoiding a large compressor while uniting the passages between the cylinders.

A reciprocating compressor according to a nineteenth aspect of the present invention is the reciprocating compressor according to any one of the ninth to eighteenth aspects of the present invention, where the exhaust passages each include a divergence passage in the direction of gravity, and the exhaust passages are each provided with an adhesive.

The reciprocating compressor has a divergence passage in the direction of gravity in each of the exhaust passages, and an adhesive is applied to each of the exhaust passage. This prevents emission of wear particles of the seal member.

A reciprocating compressor according to a twentieth aspect of the present invention, which is the reciprocating compressor according to any one of the first to nineteenth aspects of the present invention, includes a seal member attached to the piston head part. When a piston is at a bottom dead center, a seal plane along the seal member is out of square with respect to a reference plane including a center of the motor shaft and a center of the eccentric shaft.

In the reciprocating compressor, the seal plane along the seal member is out of square with respect to a reference plane including a center of a rotation shaft and the center of the eccentric shaft. Thus, compared to during an intake stroke or the like where a PV value is small and thus a low load is imposed on the seal member, an absolute value of a slope of the seal member with respect to a plane perpendicular to the reference plane is small during a compression stroke or the like where a PV value is large and thus a high load is imposed on the seal member.

Thus, when a high load is imposed on the seal member, the seal member uniformly contacts an inner surface of the cylinder. This prevents localized wear of the seal member and thus achieves a longer life time. Further, a gap between the cylinder and the seal member is reduced, which prevents air leakage thus improves the compression efficiency.

A reciprocating compressor according to a twenty-first aspect of the present invention is the reciprocating compressor according to the twentieth aspect of the present invention, where the sealing surface of the piston head part of each of the four pistons; i.e., the seal plane of the seal member is out of square with respect to the reference plane, when the piston is at the bottom dead center.

In the reciprocating compressor, the ceiling surface of the piston head part of each of the pistons serves as the seal plane of the seal member. Thus, compared to during an intake stroke or the like where a low load is imposed on the seal member, an angle of slope of the ceiling surface of the piston head part of each of the pistons is small during a compression stroke or the like where a PV is large and thus a high load is imposed on the seal member.

Thus, the seal member uniformly contacts an inner surface of the cylinder. This prevents localized wear of the seal member and thus achieves a longer life time. Further, a gap between the cylinder and the seal member is reduced, which prevents air leakage thus improves the compression efficiency.

A reciprocating compressor according to a twenty-second aspect of the present invention is the reciprocating compressor according to the twentieth or twenty-first aspect of the present invention, where an angle formed by the seal plane and the reference plane is acute at an opposite side to a travel direction of the center of the eccentric shaft with respect to the reference plane, when a piston is at the bottom dead center.

In the reciprocating compressor, an absolute value of a slope of the seal member with respect to a plane perpendicular to the reference plane is small during a compression stroke or the like where a PV value is large and thus a high load is imposed on the seal member, compared to during an intake stroke or the like where a PV value is small and thus a low load is imposed on the seal member.

Hence, localized wear of the seal member is prevented, thus achieving a longer life time of the seal member. Further, a gap between the cylinder and the seal member is reduced, which prevents air leakage thus improves the compression efficiency.

A reciprocating compressor according to a twenty-third aspect of the present invention is the reciprocating compressor according to the twenty-first aspect of the present invention, where the sealing surface of the piston head part of each of the four pistons and a retainer plate sandwich and fix a part of the seal member therebetween.

In the reciprocating compressor, the seal member is attached to the ceiling surface of the piston head part of the piston by the retainer plate. Thus, adjustment of an angle of slope of the ceiling surface of the piston allows the slope of the seal plane to be easily set.

A reciprocating compressor according to a twenty-fourth aspect of the present invention is the reciprocating compressor according to the twenty-first or the twenty-third aspect of the present invention, where the sealing surface of the piston head portion of each of the four pistons is substantially parallel to the sealing surface of the compression chamber of the corresponding one of the four cylinders, when the piston is at the top dead center.

In the reciprocating compressor, when the piston is at the top dead center, the ceiling surface of the piston head part of the piston is substantially parallel to the ceiling surface of the compression chamber of the cylinder. This reduces a dead space between the ceiling surface of the piston head part of the piston and the ceiling surface of the compression chamber of the cylinder. The compression efficiency is thus improved.

A reciprocating compressor according to a twenty-fifth aspect of the present invention is the reciprocating compressor according to any one of the twentieth to the twenty-fourth aspects of the present invention, where an absolute value of an angle of slope of the seal plane with respect to a plane perpendicular to the reference plane is smaller during a compression stroke than an intake stroke.

In the reciprocating compressor, the absolute value of the angle of slope of the seal plane with respect to the plane perpendicular to the reference plane is smaller during a compression stroke than during an intake stroke. This causes the seal member to substantially uniformly contact an inner surface of the cylinder when a high load is imposed on the seal member. Therefore, lopsided wear of the seal member is prevented and thus a long-life seal member is realized. Further, a gap between the cylinder and the seal member is reduced, which prevents air leakage thus improves the compression efficiency.

A reciprocating compressor according to a twenty-sixth aspect of the present invention is the reciprocating compressor according to any one of the twentieth to the twenty-fifth aspects of the present invention, where the seal plane is perpendicular to the reference plane when the angle of rotation of the motor shaft is at around an angle with which a PV value of the seal member is maximized.

In the reciprocating compressor, the seal plane is perpendicular to the reference plane when an angle of rotation of the rotation shaft is at around an angle with which a PV value of the seal member is maximized. This prevents localized wear of the seal member, and thus realizes a long-life seal member. Further, this prevents air leakage, thus improves the compression efficiency.

A reciprocating compressor according to a twenty-seventh aspect of the present invention, which is the reciprocating compressor according to any one of the first to the twenty-sixth aspects of the present invention, includes: a casing which accommodates the motor shaft; an exhaust gas passage provided to at least one of the casing and the four cylinders; a cooling inlet which admits a cooling medium inside the exhaust gas passage; a cooling vent which exhausts the cooling medium from the exhaust gas passage.

In the reciprocating compressor, the cooling medium is led to the inside of the reciprocating compressor through the exhaust gas passage and the cooling inlet, and exhausted outside of the reciprocating compressor through the cooling vent. This allows cooling of the seal member, the bearing, or the like of the reciprocating compressor while maintaining the sealed structure of the reciprocating compressor. Durability of the seal member or the bearing of the reciprocating compressor is thus improved, and temperature increase in the compression chamber is prevented. Therefore, the compression efficiency is improved.

An oxygen concentrator according to a twenty-eighth aspect of the present invention includes: the reciprocating compressor according to the twenty-seventh aspect of the present invention; an adsorption container; a condensed oxygen gas extraction unit; an oxygen tank; and a gas exhaust unit. Air compressed by the reciprocating compressor is supplied to the adsorption container which stores therein an adsorbent which selectively adsorbs nitrogen from the air supplied. The condensed oxygen gas extraction unit extracts condensed oxygen gas from the adsorption container. The oxygen tank stores the condensed oxygen gas from the adsorption container through the condensed oxygen gas extraction unit. By reducing pressure inside the adsorption container, nitrogen is desorbed from the adsorbent. The gas exhaust unit exhausts a gas which contains the desorbed nitrogen. The cooling medium is the nitrogen-containing gas exhausted from the adsorption container by the gas exhaust unit.

In the oxygen concentrator, a nitrogen-containing gas exhausted from the adsorption container by the gas exhaust unit is led to inside a sealed container of the reciprocating compressor through the exhaust gas passage, and is exhausted outside of the reciprocating compressor thereafter. This allows cooling of the seal member or the bearing inside the sealed container of the reciprocating compressor while maintaining the sealing structure of the reciprocating compressor. Durability of the seal member or the bearing of the reciprocating compressor is thus improved. Further, down-sizing and reduction of rotation speed of the cooling fan contribute to power saving and noise suppression of the compressor. Thus further improves the compression efficiency, and prevents decrease in oxygen concentration in condensed oxygen gas.

Further, the nitrogen-containing gas exhausted from the adsorption container is led to the eccentric shaft and the piston head parts through the exhaust gas passage, and is exhausted outside thereafter. This cools the eccentric shaft and the piston head parts in the sealed container of the reciprocating compressor. Durability of the bearing of the eccentric shaft and the seal member attached to the piston head part is thus improved, which bearing and seal member generate particularly high heat.

EFFECT OF THE INVENTION

As described above, the present invention achieves the following effects.

According to the first to eighth aspects of the present invention, the number of cylinders is increased from two to four. This allows a smaller stroke of each piston while maintaining rotation speed of each piston and a total exhaust flow rate. Thus, an angle of oscillation of each piston is maintained despite a shorter piston rod. This realizes a smaller compressor while ensuring airtightness of the compression chamber. Further, a smaller stroke leads to a shorter oscillation distance of the piston head part. Thus, a sealing characteristic of the seal member provided to the piston head part is ensured for a long period of time. Further, the four cylinders greatly expand heat dissipating surface. This prevents a temperature increase in the compression chambers, thus greatly improving the compression efficiency. Further, the pistons make intake-compression strokes while the four compression chambers maintain a ninety-degree phase difference with each other. This balances out a force acting on the motor shaft and thus restrains fluctuations in running torque. The compression efficiency is thus improved. Further, intake-exhaust sounds are balanced out as well, which realizes lower noise and less vibration.

In the ninth to nineteenth aspects of the present invention, the passages between the cylinders are united due to at least one of the shared intake passage and the shared exhaust passage. Further, at least one of the shared intake passage and the shared exhaust passage is provided overlapping at least one of the axial region extending in the axial direction of the motor shaft and the peripheral region thereof. This avoids a large compressor due to the shared passage(s). As a result, the passages between the cylinders are shared while avoiding a large compressor.

In the twentieth to twenty-sixth aspects of the present invention, the seal plane along the seal member is out of square with respect to the reference plane including the center of the rotation shaft and the center of the eccentric shaft when the piston is at the bottom dead center. Thus, compared to during an intake stroke or the like where a PV value is small thus a low load is imposed on the seal member, an absolute value of an inclination of the seal plane with respect to the plane perpendicular to the reference plane is small during a compression stroke or the like where a PV value is high and thus a high load is imposed on the seal member. This causes the seal member to substantially uniformly contact an inner surface of the cylinder when a high load is imposed on the seal member. Therefore, localized wear of the seal member is prevented and thus a long-life seal member is realized. Further, a gap between the cylinder and the seal member is reduced, which prevents air leakage thus improves the compression efficiency.

In the twenty-seventh and twenty-eighth aspects of the present invention, the cooling medium is led inside the reciprocating compressor through the exhaust gas passage and the cooling inlet, and is exhausted outside through the cooling vent thereafter. This cools the seal member or the bearing of the reciprocating compressor while maintaining the sealing structure of the reciprocating compressor. Durability of the seal member or the bearing of the reciprocating compressor is thus improved. This improves the compression efficiency. Further, down-sizing and reduction speed of the cooling fan contribute to power saving and noise suppression of the compressor, thus preventing decrease in oxygen concentration in the condensed oxygen gas.

BRIEF DESCRIPTION OF THE DRAWINGS

FIG. 15 is a schematic view of the bearing support member in FIG. 14, where (a) is a schematic bottom view, (b) is a schematic cross-sectional view taken along the N-N line, and (c) is a schematic cross-sectional view taken along the M-M line.

FIG. 16 is a schematic view of the bearing support member in FIG. 14, where (a) is an overhead schematic view, and (b) is a schematic cross-sectional view taken along the O-O line.

FIG. 17 is a schematic view of the cylinder in FIG. 1, where (a) is a schematic side view on the X arrow in (b), (b) is a schematic front view, and (c) is a schematic cross-sectional view taken along the K-K line.

FIG. 21 is an exploded explanatory view of a piston provided inside the reciprocating compressor in FIG. 1, where (a) is an explanatory view of four pistons, and (b) is an explanatory view of a piston.

FIG. 32(a) is a longitudinal cross-sectional view illustrating a cooling inlet, and FIG. 32(b) is a longitudinal cross-sectional view illustrating a cooling vent.

DETAILED DESCRIPTION OF THE INVENTION (First Embodiment)

The following describes a preferred embodiment of the present invention with reference to the figures.

Figure 1:
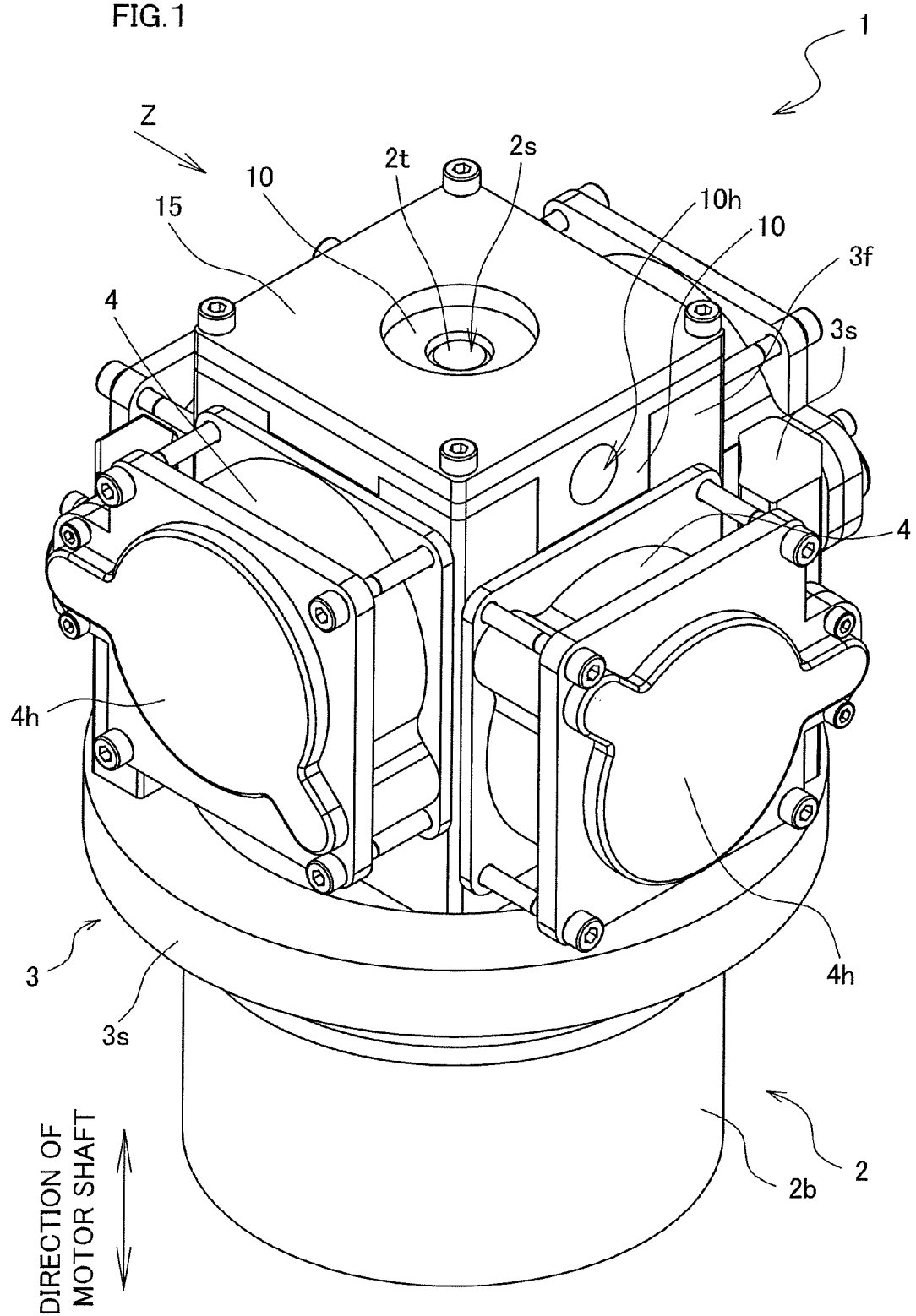
FIG. 1 is a schematic perspective view of a reciprocating compressor according to a first embodiment of the present invention.

FIG. 1 is a schematic perspective view of a reciprocating compressor according to the first embodiment of the present invention.

Figure 2:
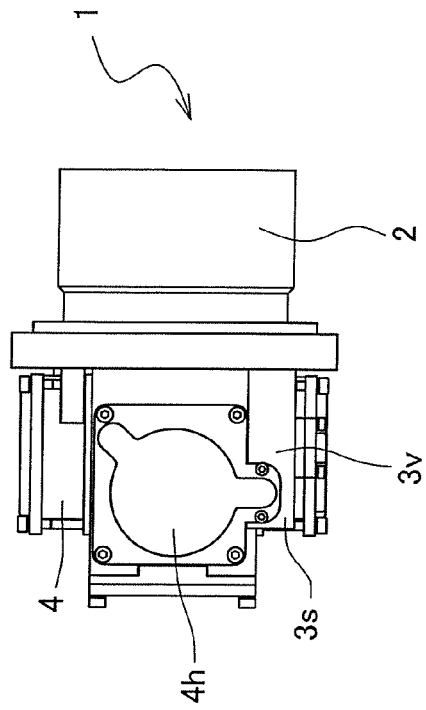
FIG. 2 is a schematic view of the reciprocating compressor of FIG. 1, where (a) is an overhead schematic view, (b) is a schematic side view on the X arrow, and (c) is a schematic side view on the Y arrow.
Figure 2:
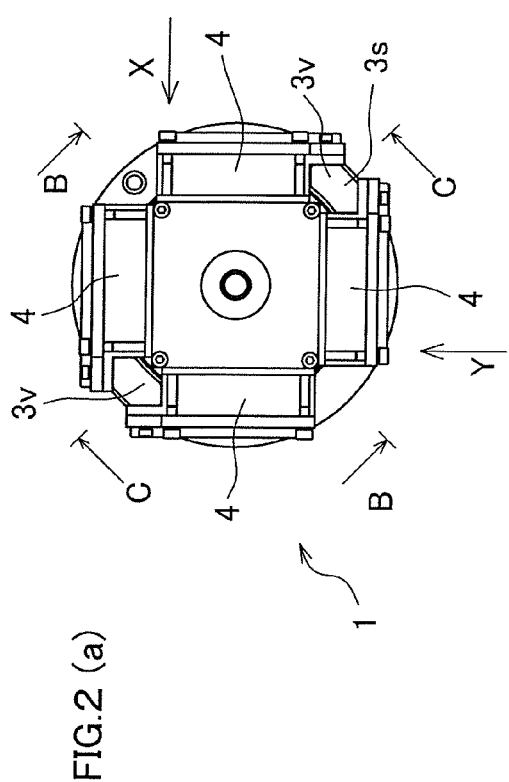
Figure 2:
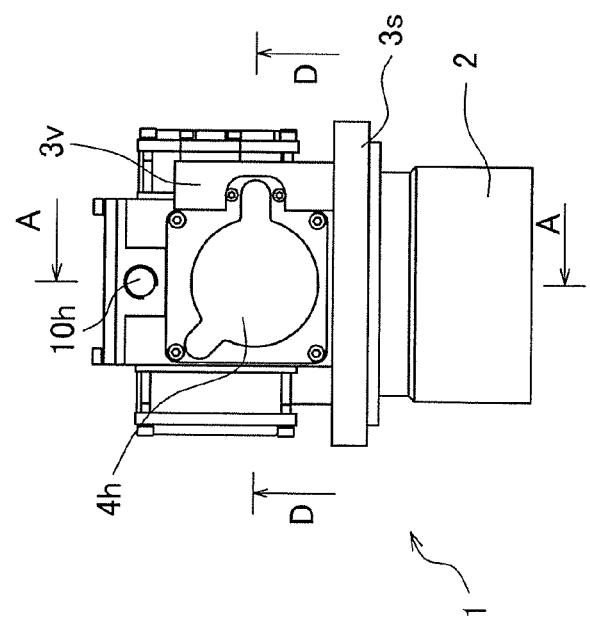

FIG. 2 is a schematic view of the reciprocating compressor in FIG. 1, where (a) is an overhead schematic view, (b) is a schematic side view on the X arrow, and (c) is a schematic side view on the Y arrow.

Figure 3:
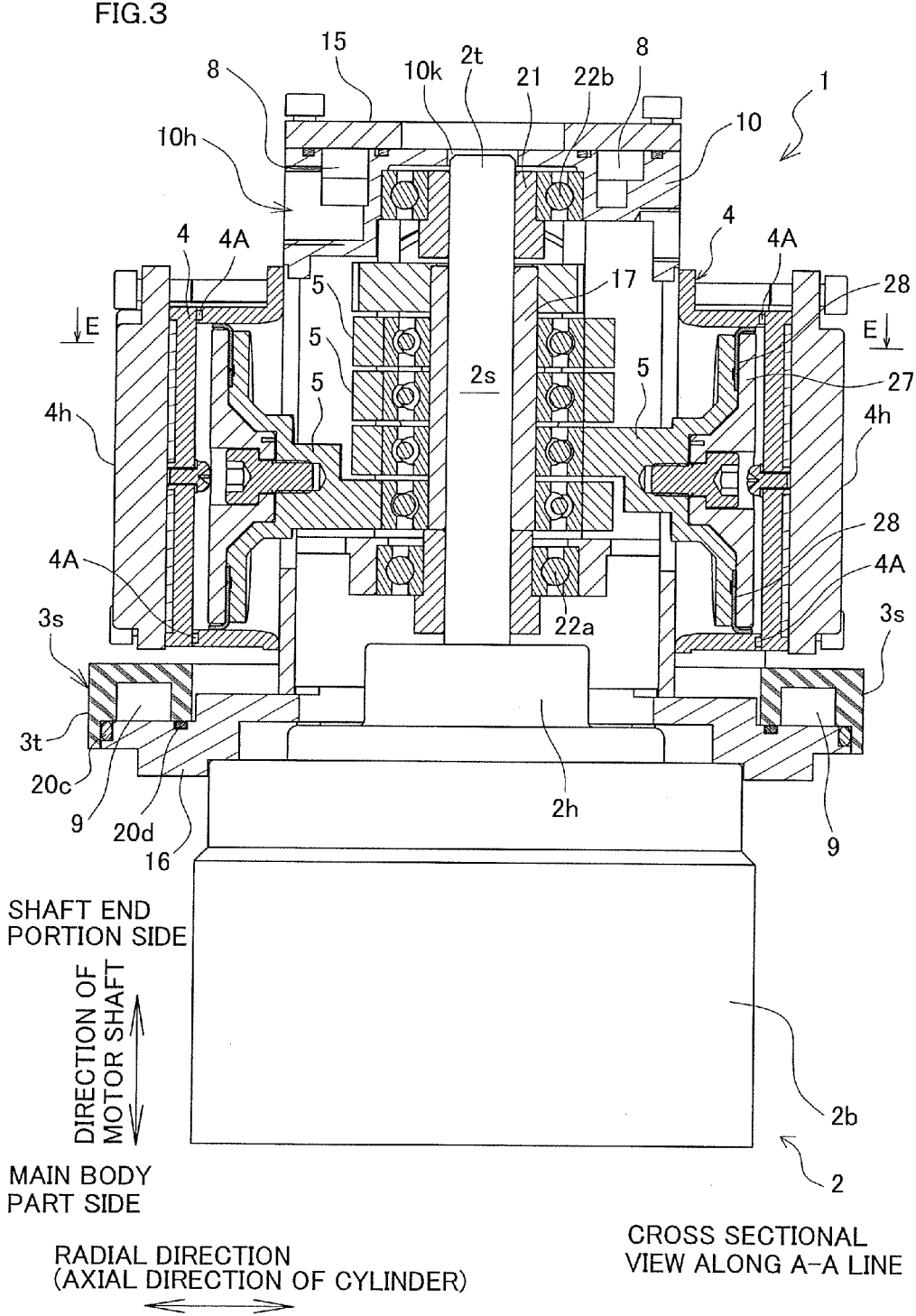
FIG. 3 is a schematic cross-sectional view taken along the A-A line in FIG. 2(c).

FIG. 3 is a schematic cross-sectional view taken along the A-A line in FIG. 2(c).

Figure 4:
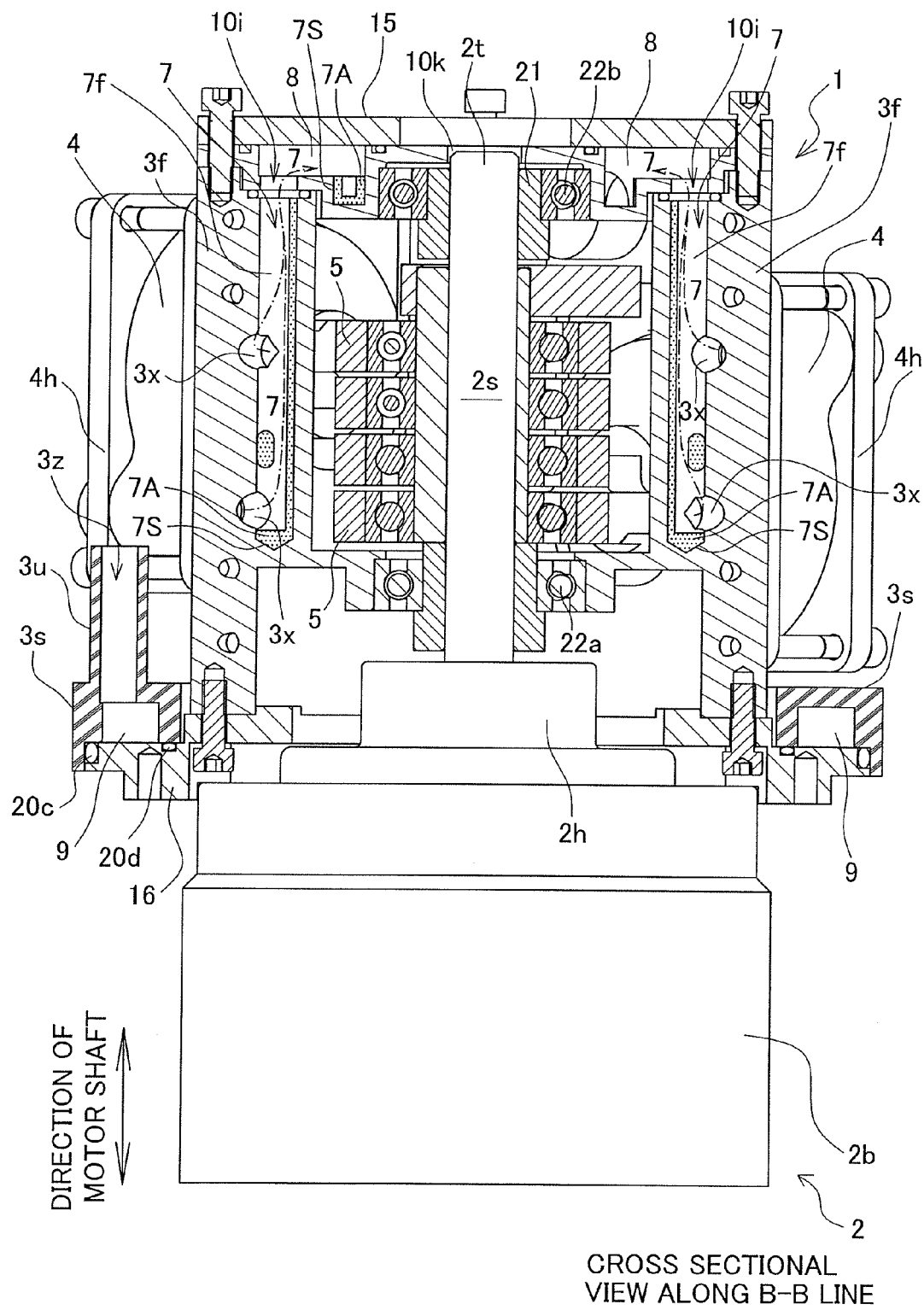
FIG. 4 is a schematic cross-sectional view taken along the B-B line in FIG. 2(a).

FIG. 4 is a schematic cross-sectional view taken along the B-B line in FIG. 2(a).

Figure 5:
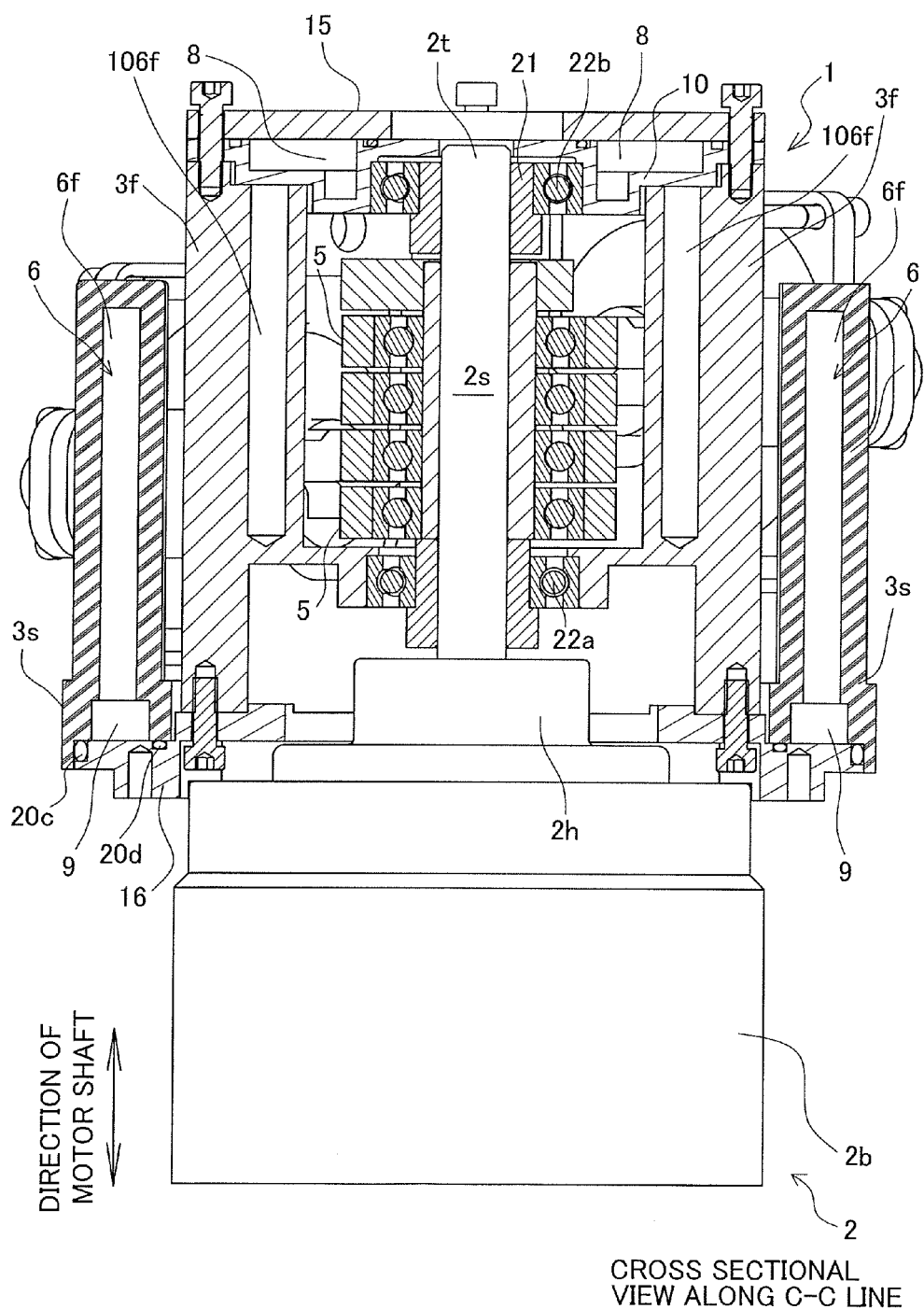
FIG. 5 is a schematic cross-sectional view taken along the C-C line in FIG. 2(a).

FIG. 5 is a schematic cross-sectional view taken along the C-C line in FIG. 2(a).

Figure 6:
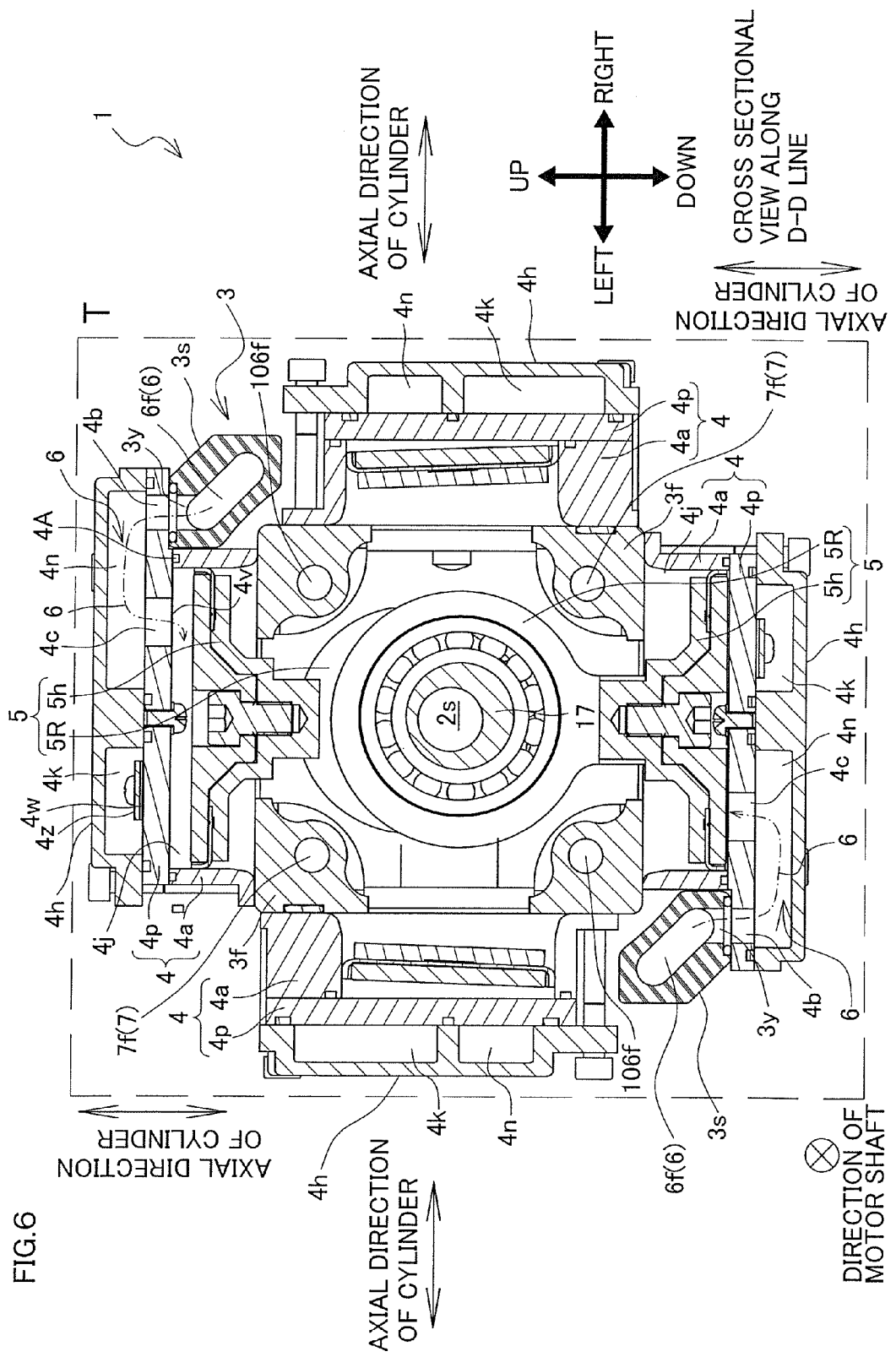
FIG. 6 is a schematic cross-sectional view taken along the D-D line in FIG. 2(c).

FIG. 6 is a schematic cross-sectional view taken along the D-D line in FIG. 2(c).

Figure 7:
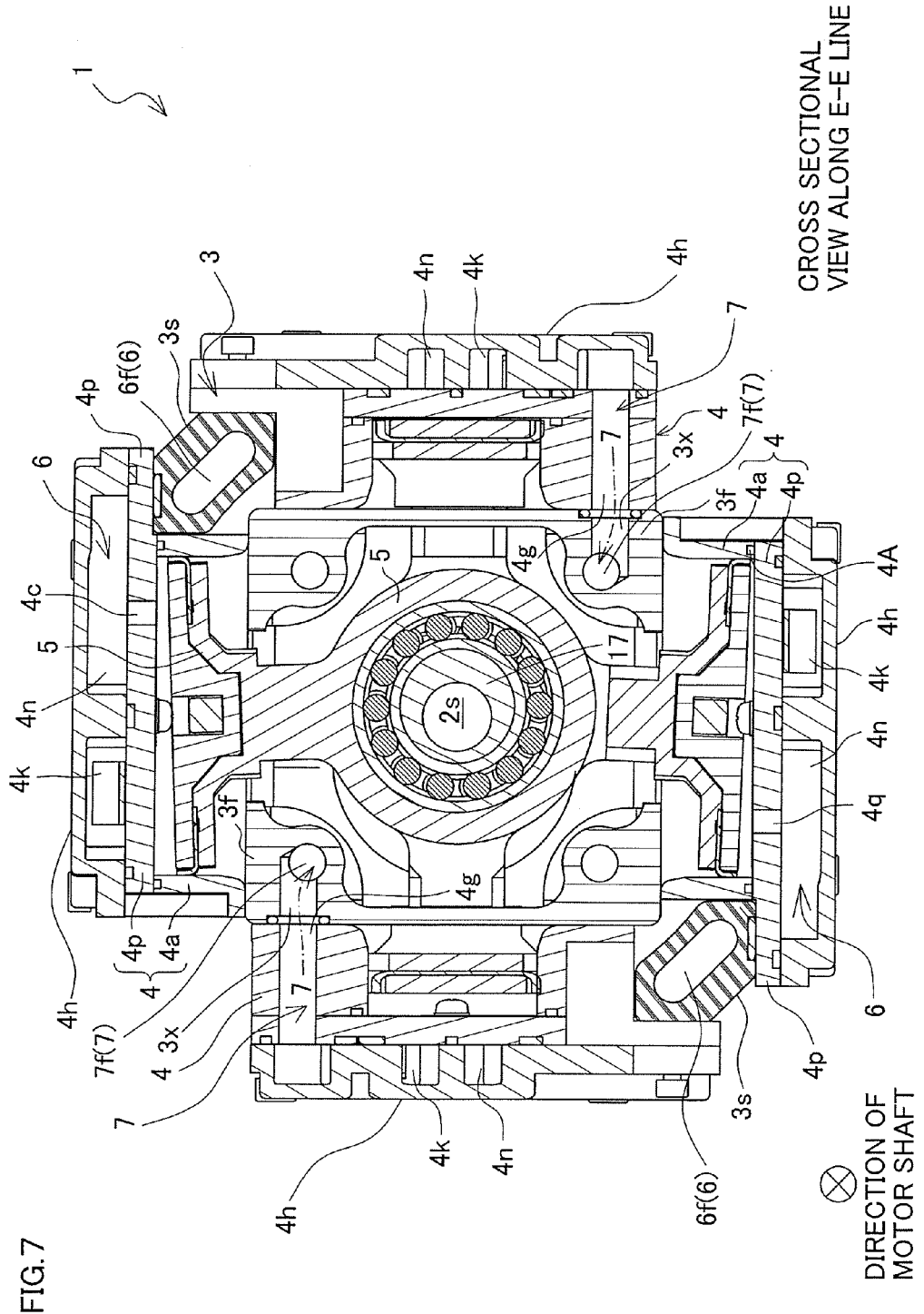
FIG. 7 is a schematic cross-sectional view taken along the E-E line in FIG. 3.

FIG. 7 is a schematic cross-sectional view taken along the E-E line in FIG. 3.

Figure 8:
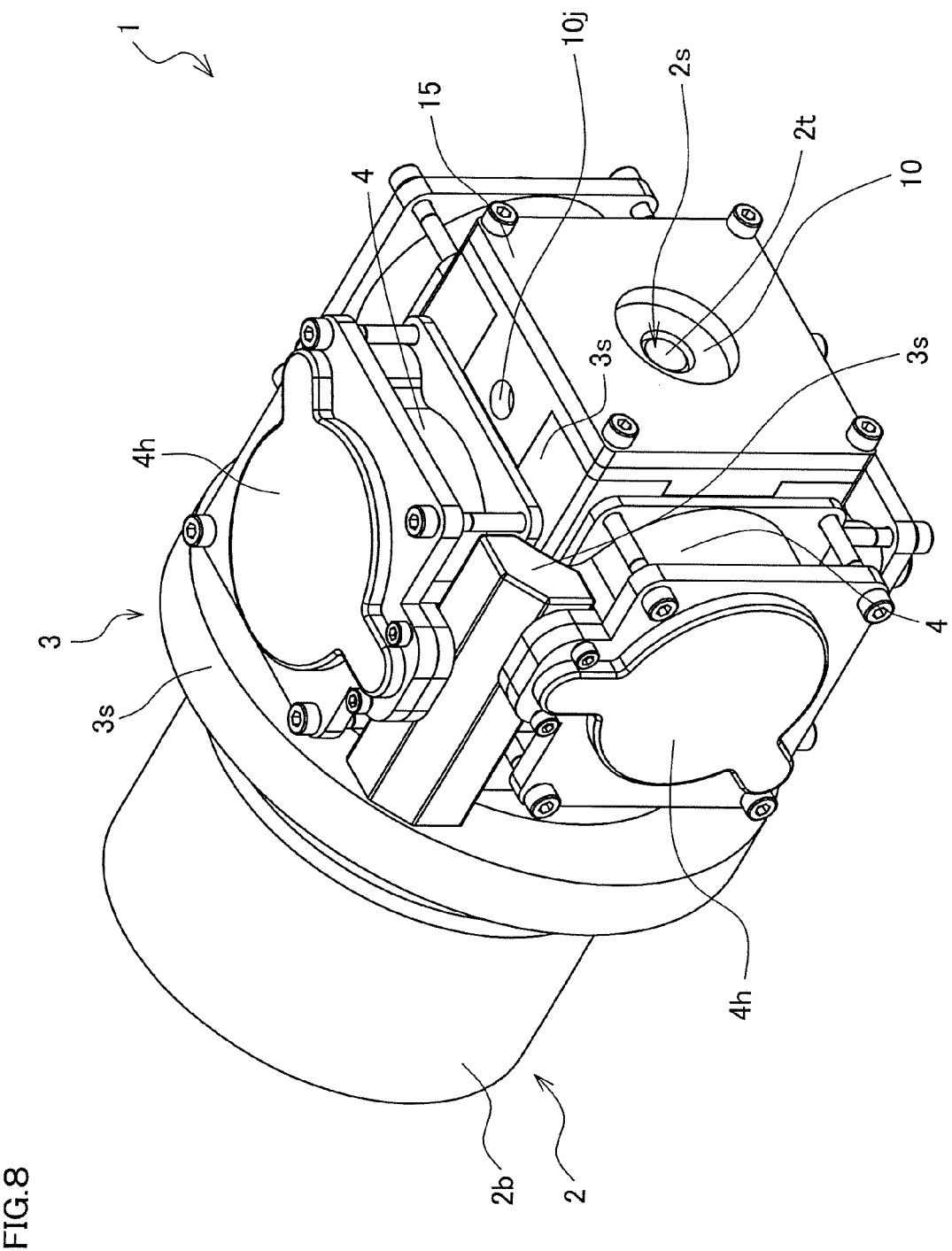
FIG. 8 is a schematic perspective view of the reciprocating compressor taken along the Z-Z line in FIG. 1.

FIG. 8 is a schematic perspective view of the reciprocating compressor taken along the Z-Z line in FIG. 1.

Figure 9:
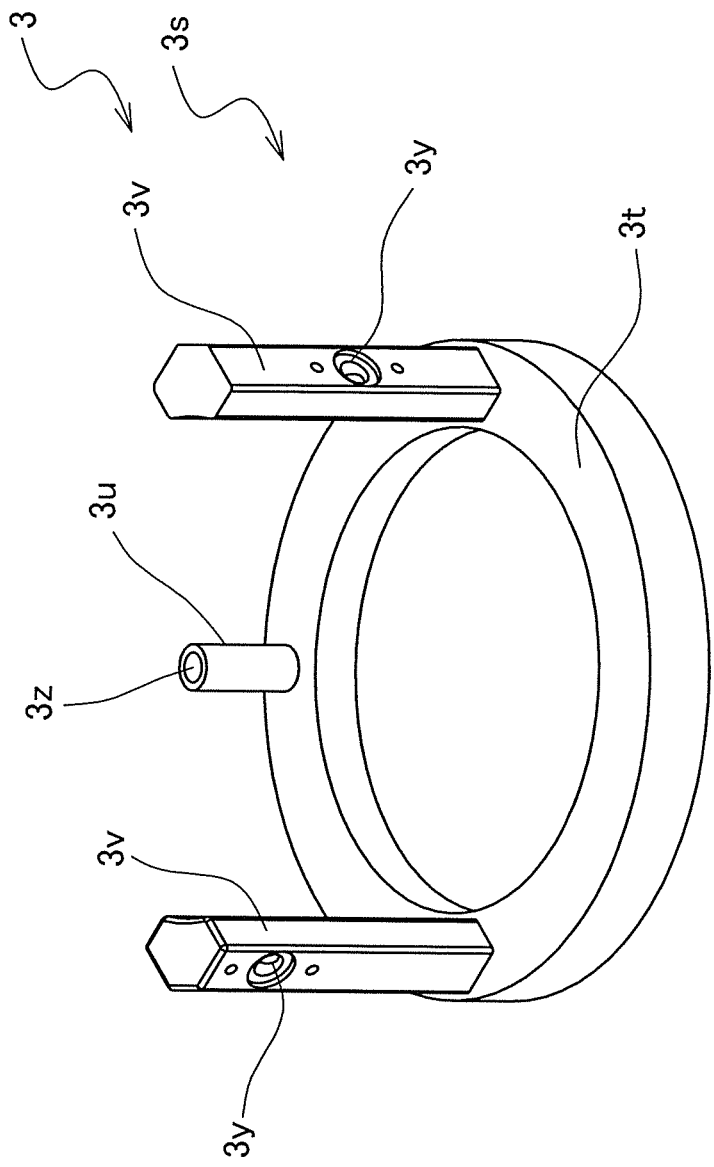
FIG. 9 is a schematic perspective view of a second member in the casing in FIG. 1.

FIG. 9 is a schematic perspective view of a second member in the casing in FIG. 1.

Figure 10:
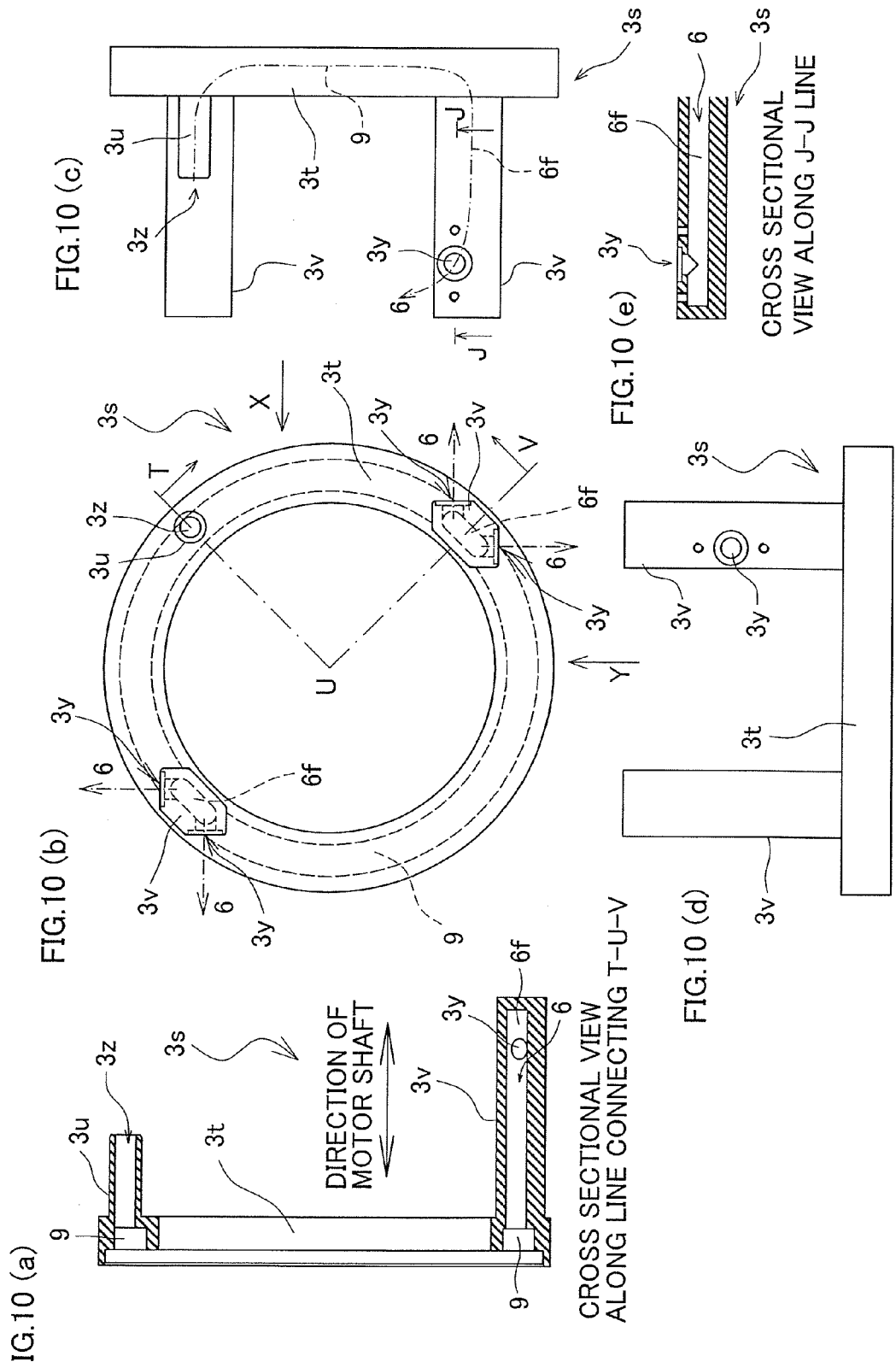
FIG. 10 is a schematic view of the second member in FIG. 9, where (a) is a cross sectional view taken along a line connecting the T, U, and V, (b) is an overhead schematic view, (c) is a schematic side view on the X arrow, (d) is a schematic side view on the Y arrow, and (e) is a cross-sectional view taken along the J-J line.

FIG. 10 is a schematic view of the second member in FIG. 9, where (a) is a cross sectional view taken along a line connecting the T, U, and V, (b) is an overhead schematic view, (c) is a schematic side view on the X arrow, (d) is a schematic side view on the Y arrow, and (e) is a cross-sectional view taken along the J-J line.

Figure 11:
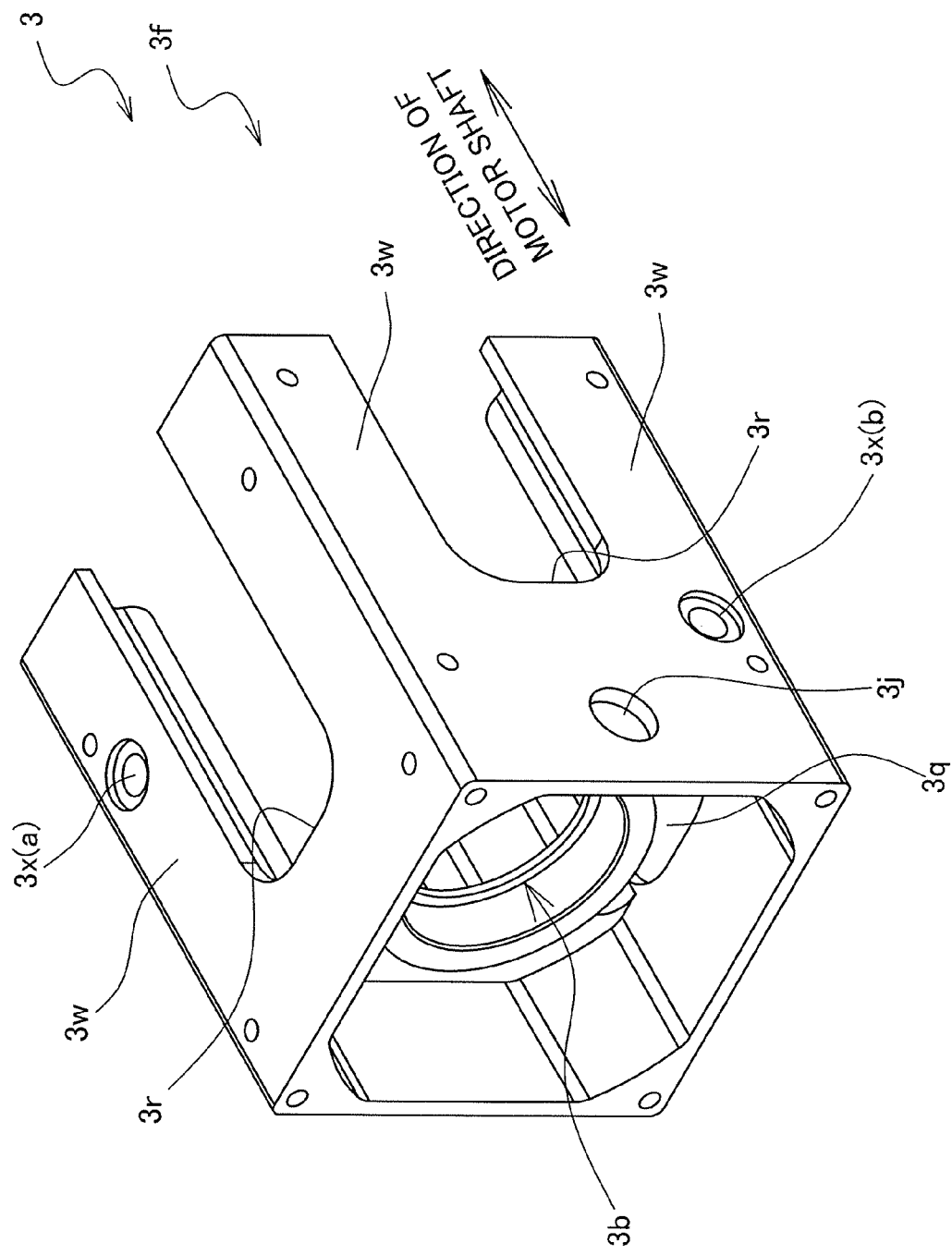
FIG. 11 is a schematic perspective view of the first member of the casing of FIG. 1.

FIG. 11 is a schematic perspective view of the first member of the casing of FIG. 1.

Figure 12:
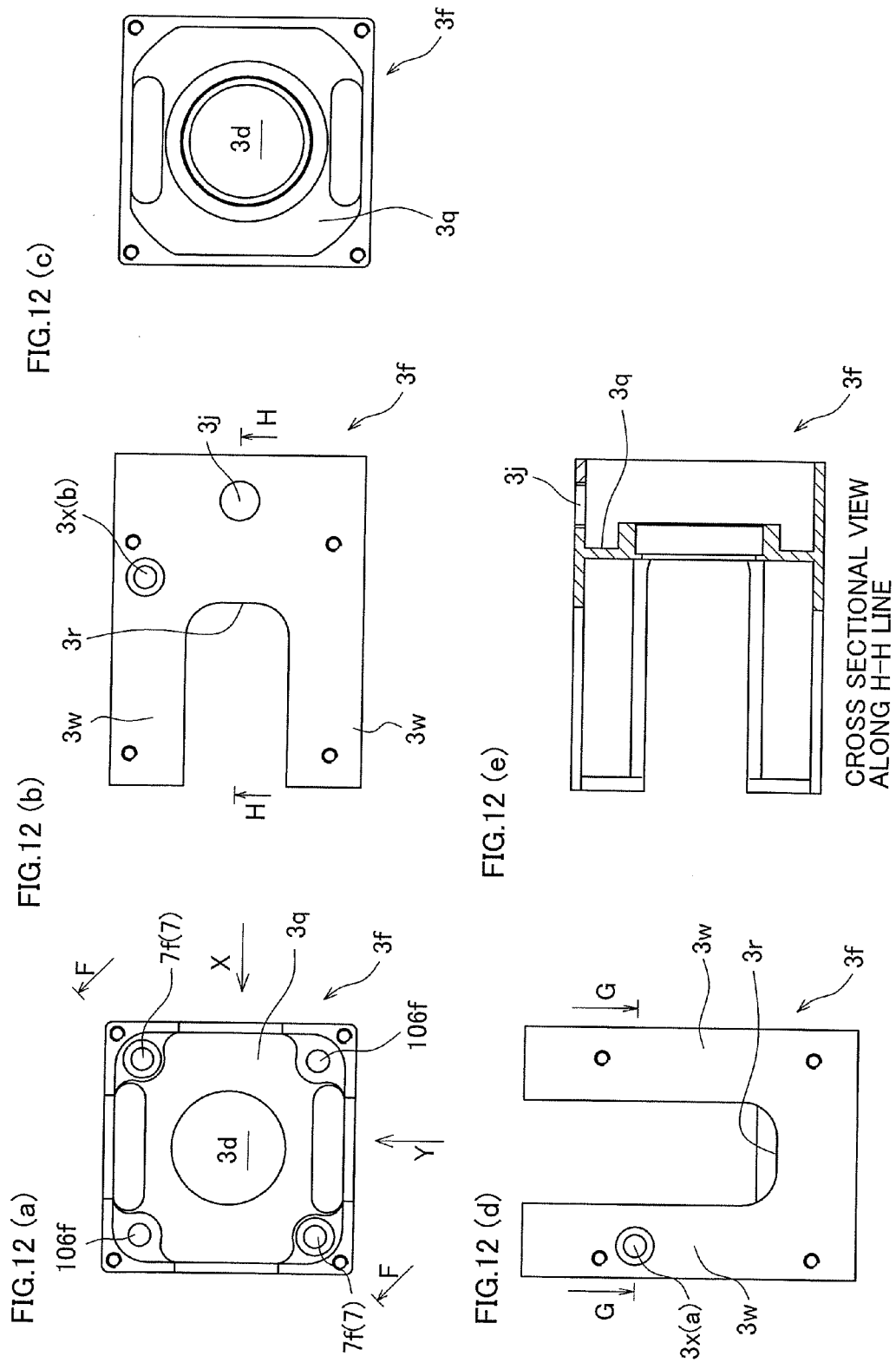
FIG. 12 is a schematic view of the first member in FIG. 11, where (a) is an overhead schematic view, (b) is a schematic view on the X arrow, (c) is a schematic bottom view, (d) is a schematic side view on the Y arrow, and (e) is a cross-sectional view taken along the H-H line.

FIG. 12 is a schematic view of the first member in FIG. 11, where (a) is an overhead schematic view, (b) is a schematic view on the X arrow, (c) is a schematic bottom view, (d) is a schematic side view on the Y arrow, and (e) is a cross-sectional view taken along the H-H line.

Figure 13:
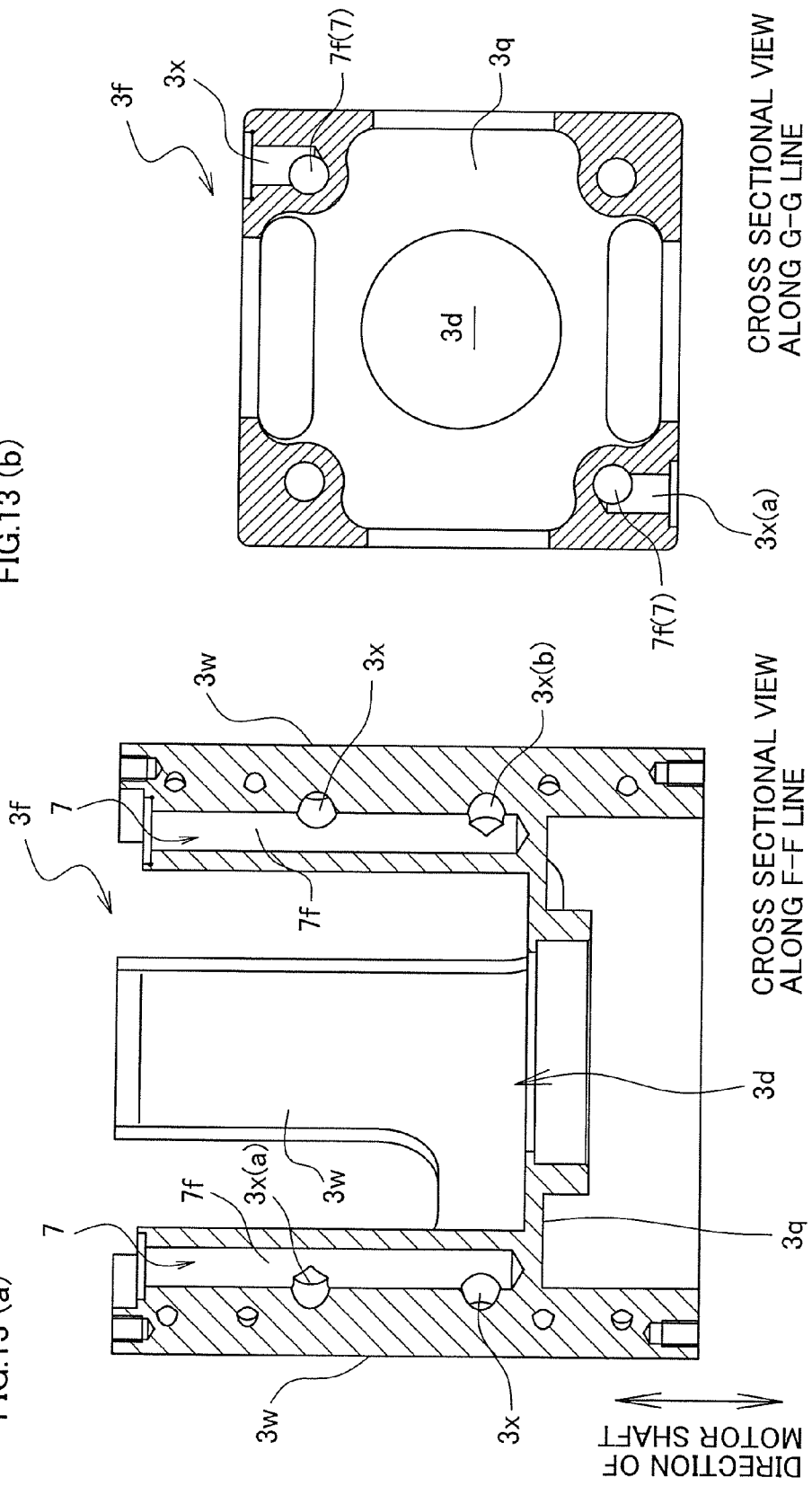
FIG. 13 is a cross-sectional view of the first member in FIG. 11, where (a) is a schematic cross sectional view taken along the F-F line in FIG. 12, and (b) is a schematic cross-sectional view taken along the G-G line in FIG. 12.

FIG. 13 is a cross-sectional view of the first member in FIG. 11, where (a) is a schematic cross sectional view taken along the F-F line in FIG. 12, and (b) is a schematic cross-sectional view taken along the G-G line in FIG. 12.

Figure 14:
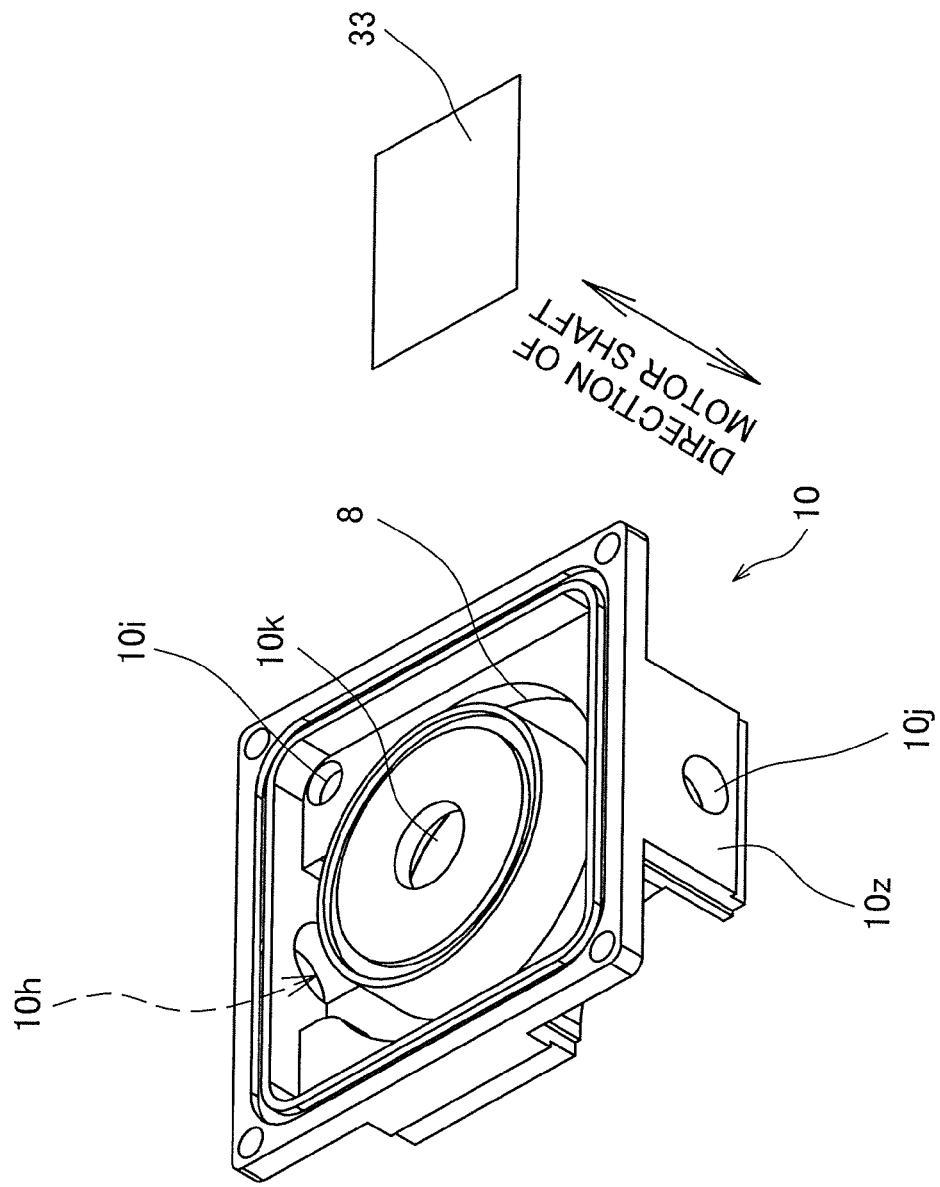
FIG. 14 is a schematic perspective view of the bearing support member in FIG. 1.

FIG. 14 is a schematic perspective view of the bearing support member in FIG. 1.

FIG. 15 is a schematic view of the bearing support member in FIG. 14, where (a) is a schematic bottom view, (b) is a schematic cross-sectional view taken along the N-N line, and (c) is a schematic cross-sectional view taken along the M-M line.

FIG. 16 is a schematic view of the bearing support member in FIG. 14, where (a) is an overhead schematic view, and (b) is a schematic cross-sectional view taken along the O-O line.

FIG. 17 is a schematic view of the cylinder in FIG. 1, where (a) is a schematic side view on the X arrow in (b), (b) is a schematic front view, and (c) is a schematic cross-sectional view taken along the K-K line.

Figure 18:
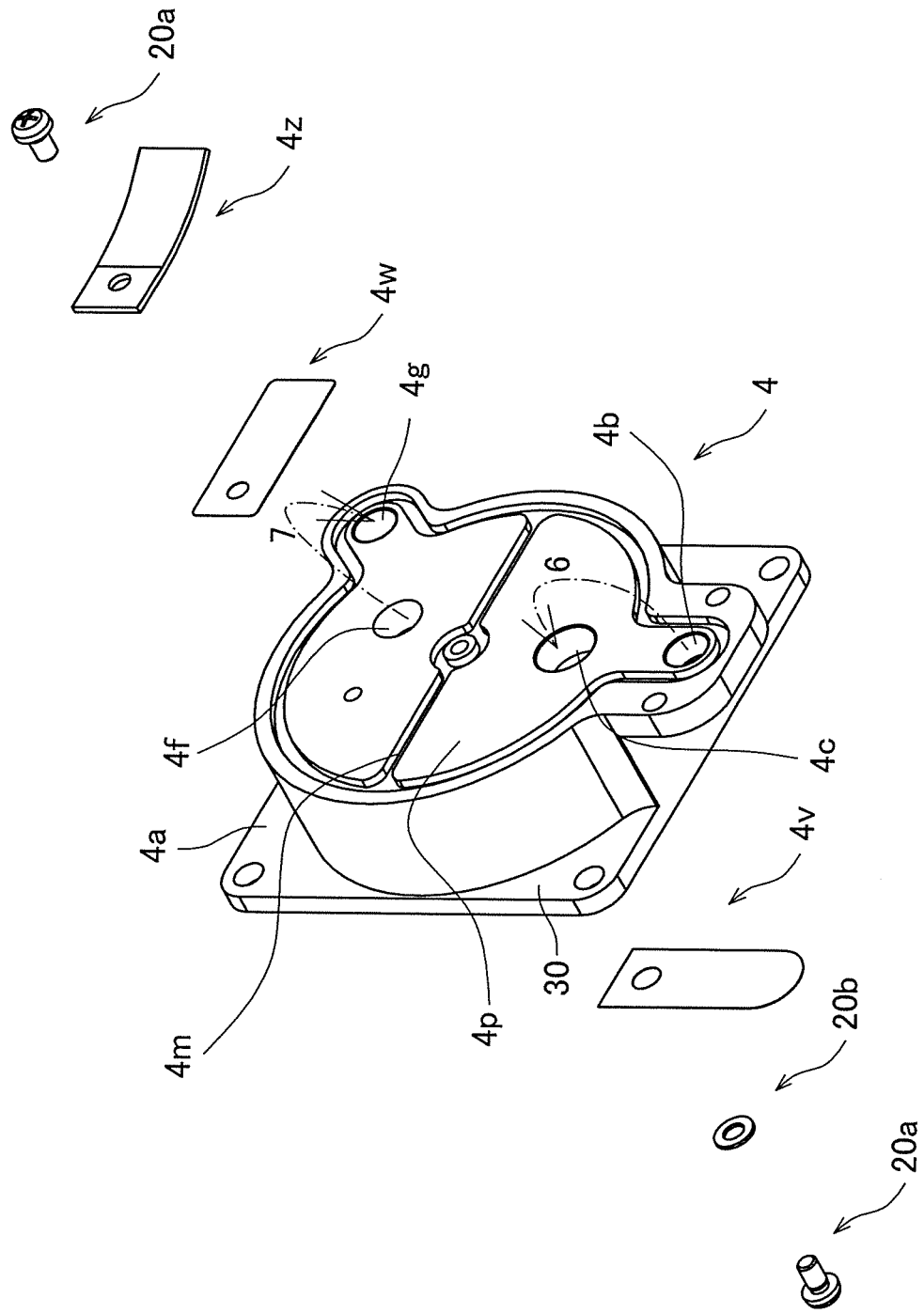
FIG. 18 is an explanatory perspective view of a member installed to the cylinder in FIG. 1 and the cylinder.

FIG. 18 is an explanatory perspective view of a member installed to the cylinder in FIG. 1 and the cylinder.

Figure 19:
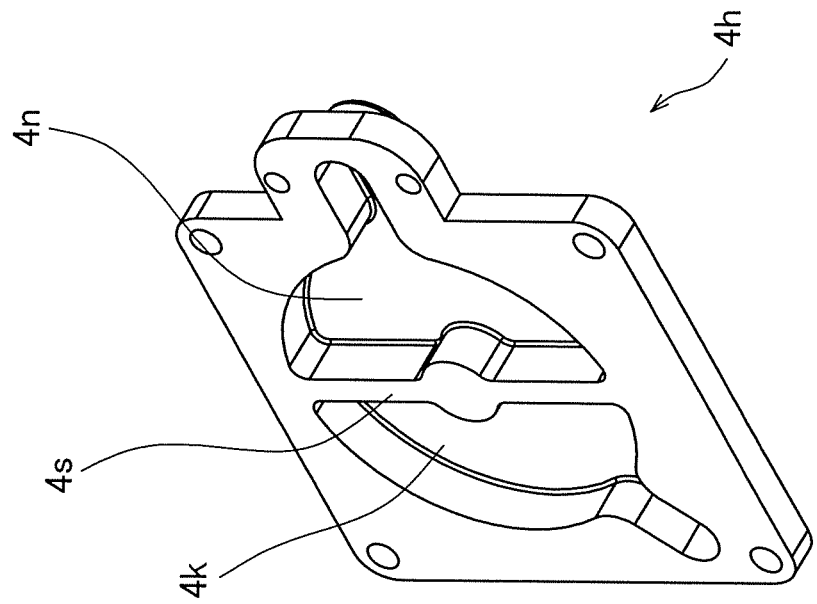
FIG. 19 is a schematic perspective view of the head cover in FIG. 1.

FIG. 19 is a schematic perspective view of the head cover in FIG. 1.

Figure 20:
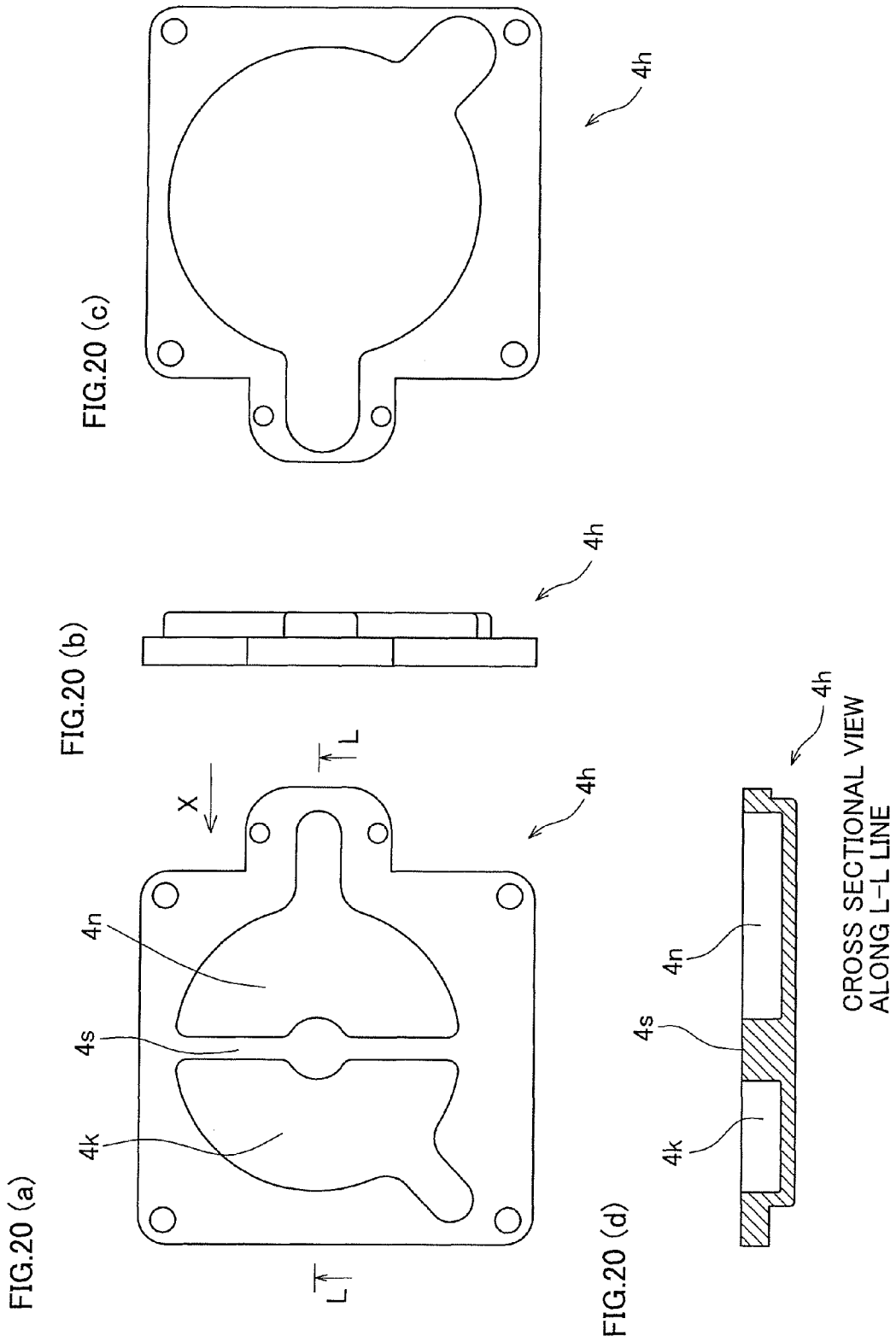
FIG. 20 is a schematic view of the head cover in FIG. 19, where (a) is a schematic interior view, (b) is a schematic side view on the X arrow, (c) is a schematic exterior view, and (d) is a schematic cross-sectional view taken along the L-L line.

FIG. 20 is a schematic view of the head cover in FIG. 19, where (a) is a schematic interior view, (b) is a schematic side view on the X arrow, (c) is a schematic exterior view, and (d) is a schematic cross-sectional view taken along the L-L line.

FIG. 21 is an exploded explanatory view of a piston provided inside the reciprocating compressor in FIG. 1, where (a) is an explanatory view of four pistons, and (b) is an explanatory view of a piston.

Figure 22:
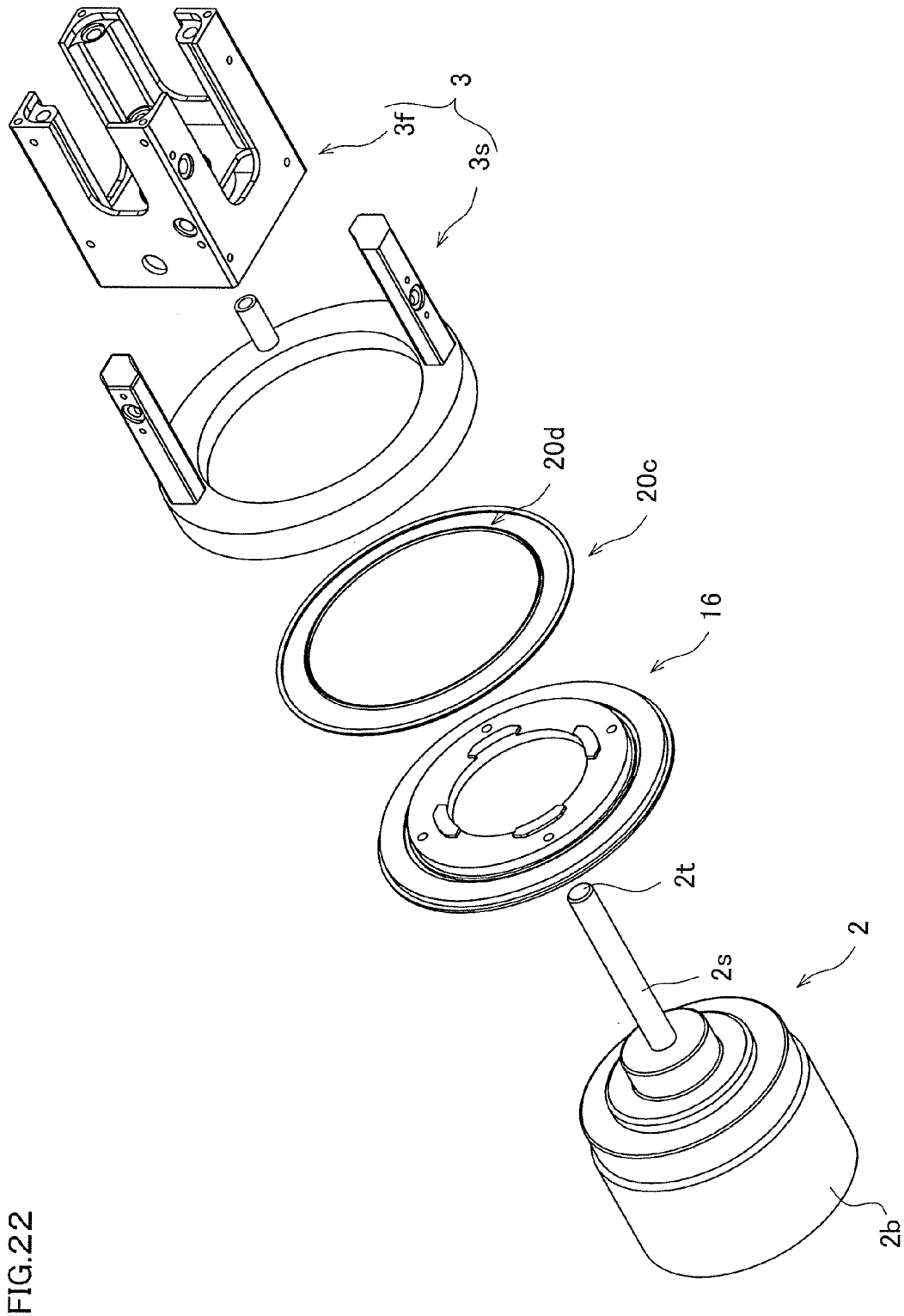
FIG. 22 is a schematic perspective view illustrating installation of a casing in assembly of the reciprocating compressor in FIG. 1.

FIG. 22 is a schematic perspective view illustrating installation of a casing in assembly of the reciprocating compressor in FIG. 1.

Figure 23:
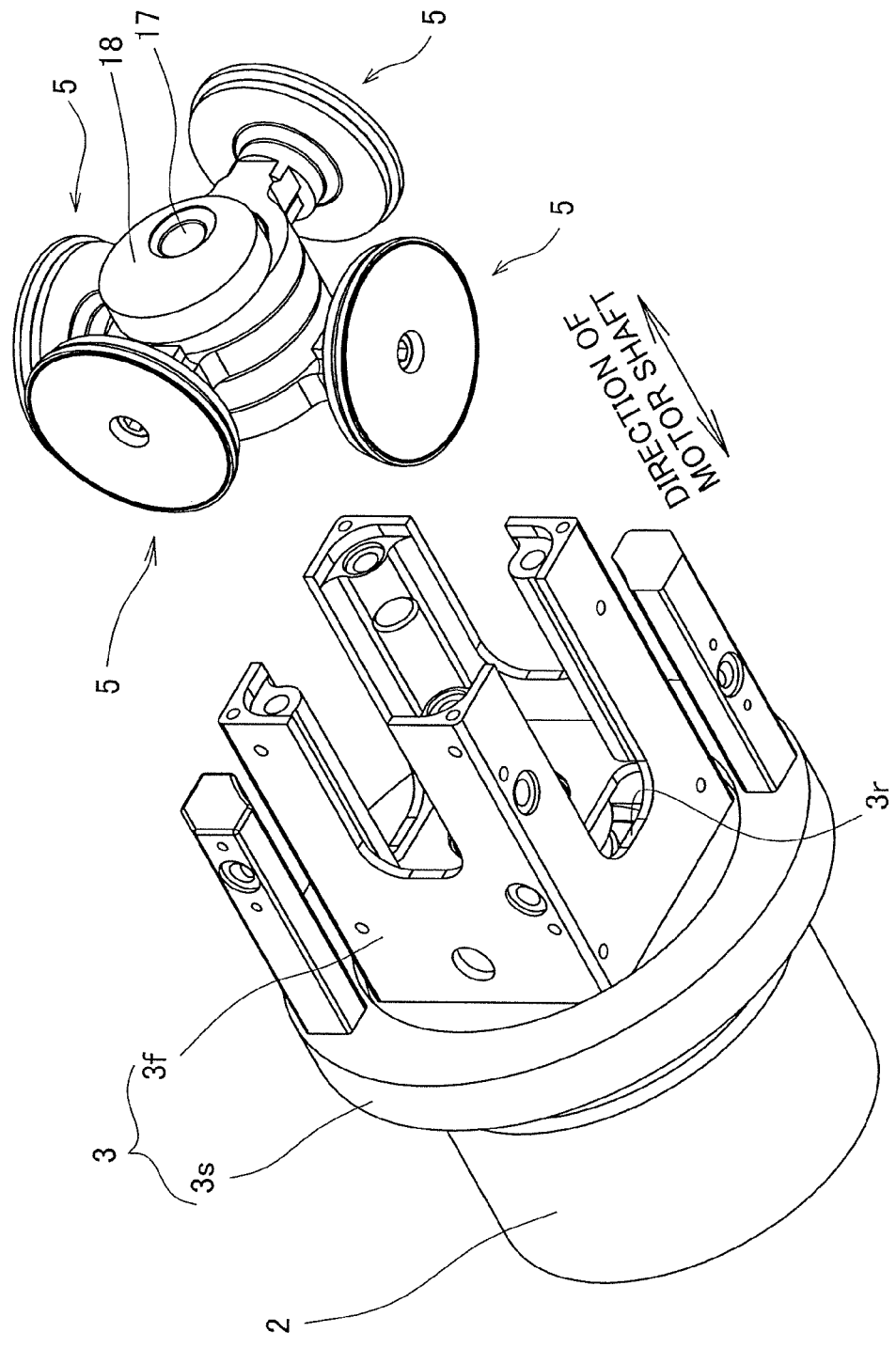
FIG. 23 is an explanatory perspective view illustrating installation of pistons in assembly of the reciprocating compressor in FIG. 1.

FIG. 23 is an explanatory perspective view illustrating installation of pistons in assembly of the reciprocating compressor in FIG. 1.

Figure 24:
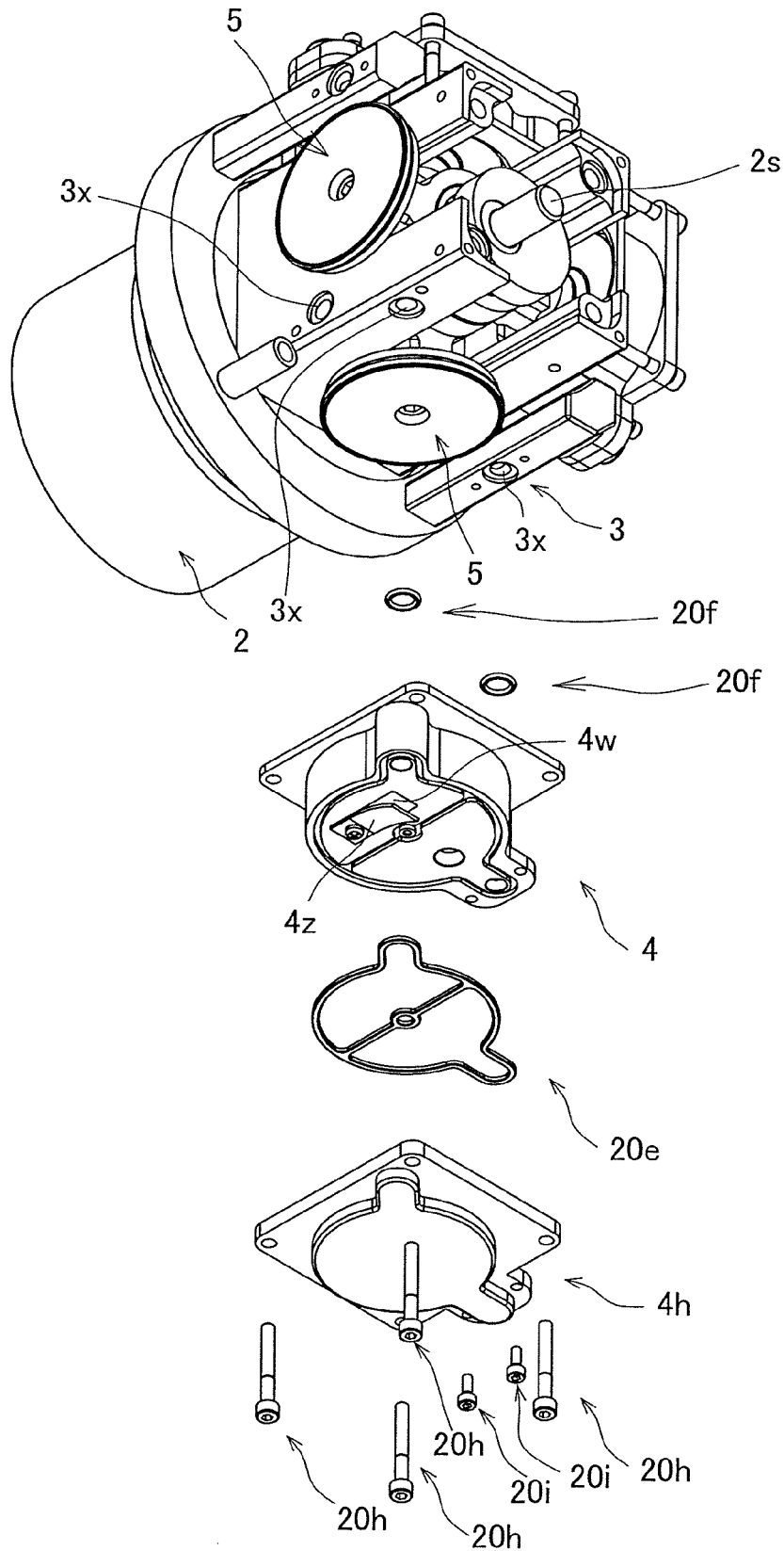
FIG. 24 is an explanatory perspective view illustrating installation of a cylinder and the like in assembly of the reciprocating compressor in FIG. 1.

FIG. 24 is an explanatory perspective view illustrating installation of a cylinder and the like in assembly of the reciprocating compressor in FIG. 1.

Figure 25:
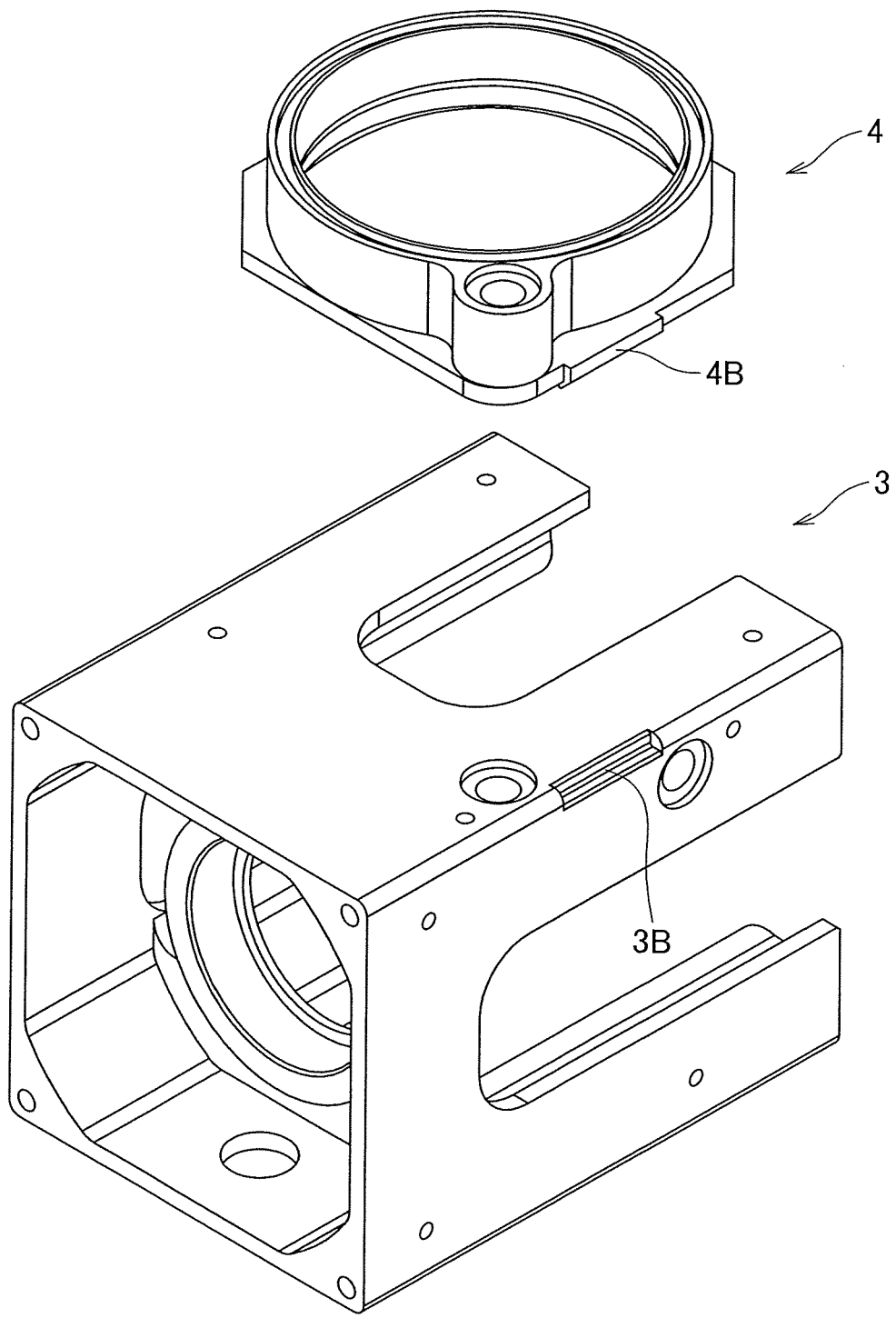
FIG. 25 is an explanatory perspective view illustrating positioning of a cylinder with respect to a casing in assembly of the reciprocating compressor in FIG. 1.

FIG. 25 is an explanatory perspective view illustrating positioning of a cylinder with respect to a casing in assembly of the reciprocating compressor in FIG. 1.

Figure 26:
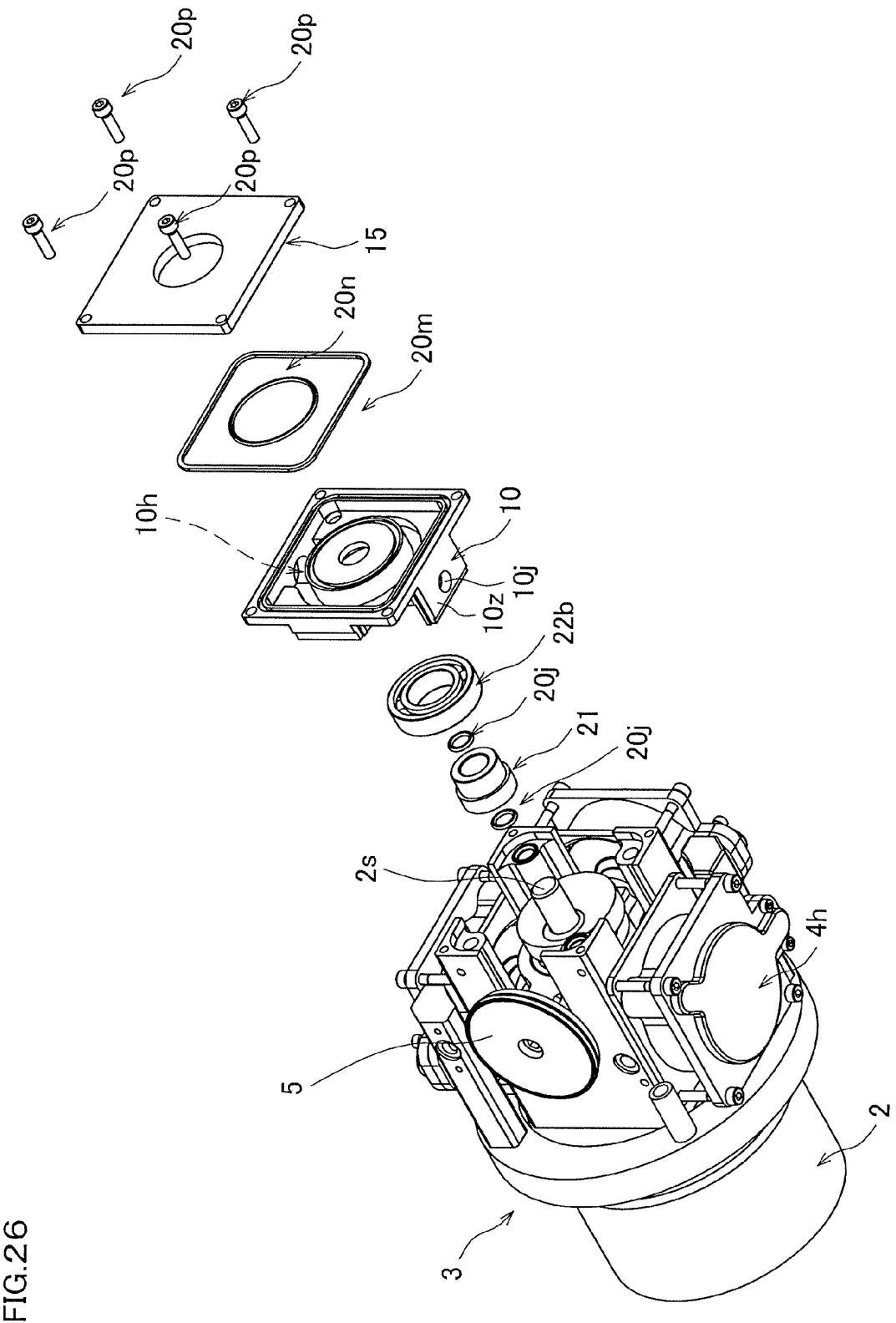
FIG. 26 is an explanatory perspective view illustrating installation of a bearing support member, a casing cover, and the like in assembly of the reciprocating compressor in FIG. 1.

FIG. 26 is an explanatory perspective view illustrating installation of a bearing support member, a casing cover, and the like in assembly of the reciprocating compressor in FIG. 1.

Figure 27:
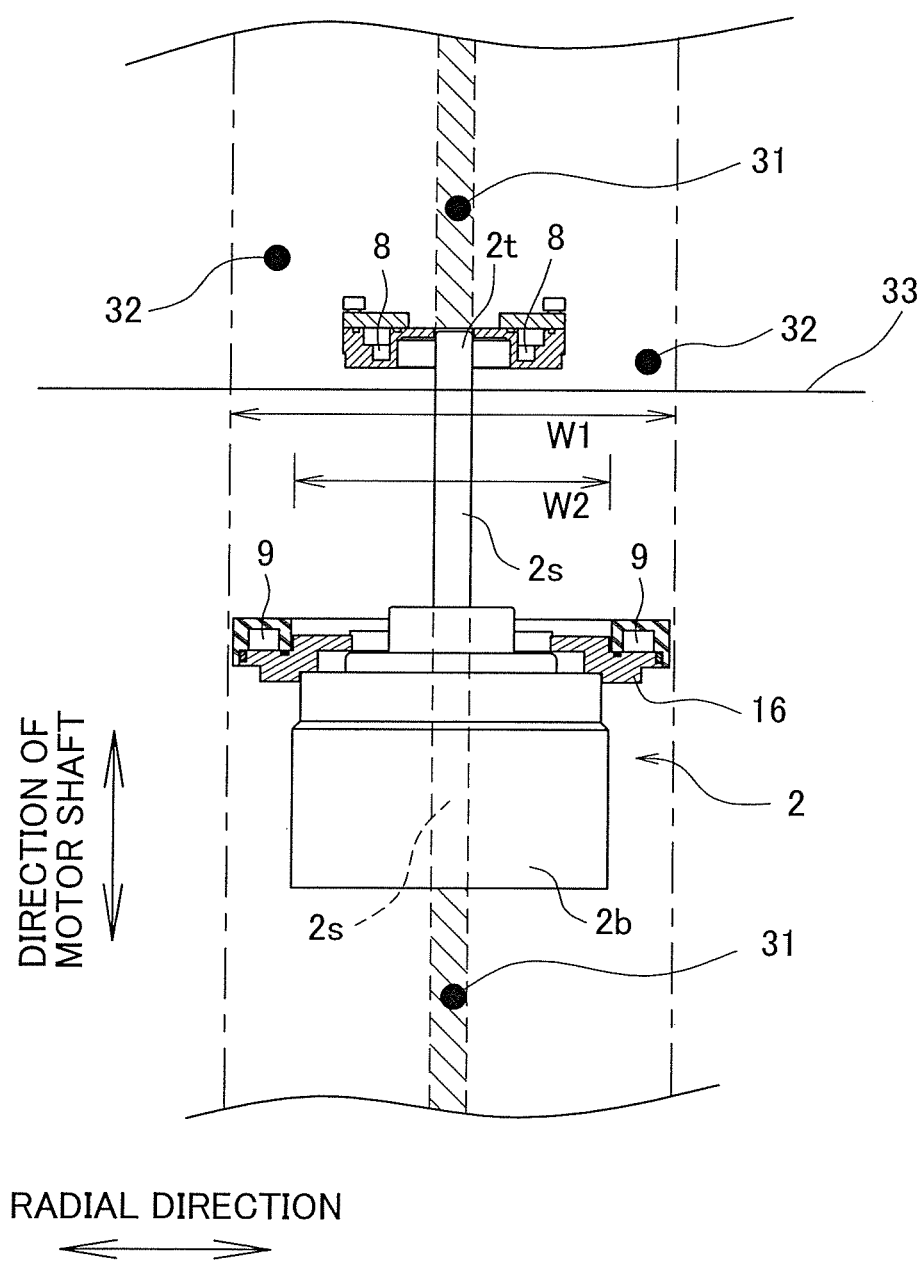
FIG. 27 is a schematic explanatory view illustrating an axial region and peripheral region thereof in the reciprocating compressor in FIG. 1.

FIG. 27 is a schematic explanatory view illustrating an axial region and peripheral region thereof of the reciprocating compressor in FIG. 1.

Figure 28:
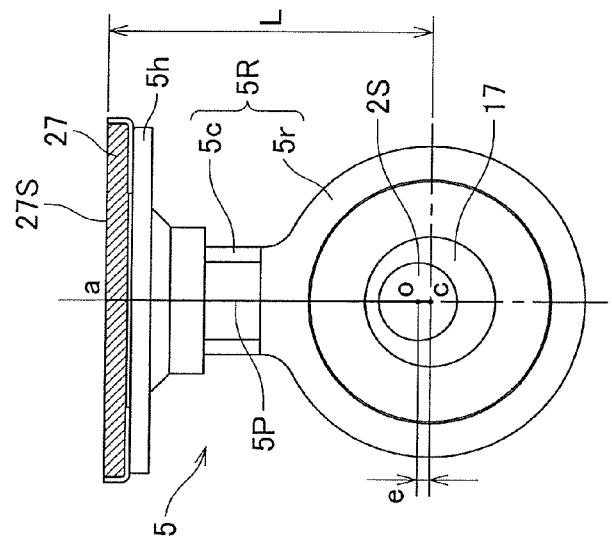
FIG. 28 is an explanatory view of a piston rod, where (a) is an overhead schematic view of a reciprocating compressor, and (b) is an overhead schematic view of a piston.
Figure 28:
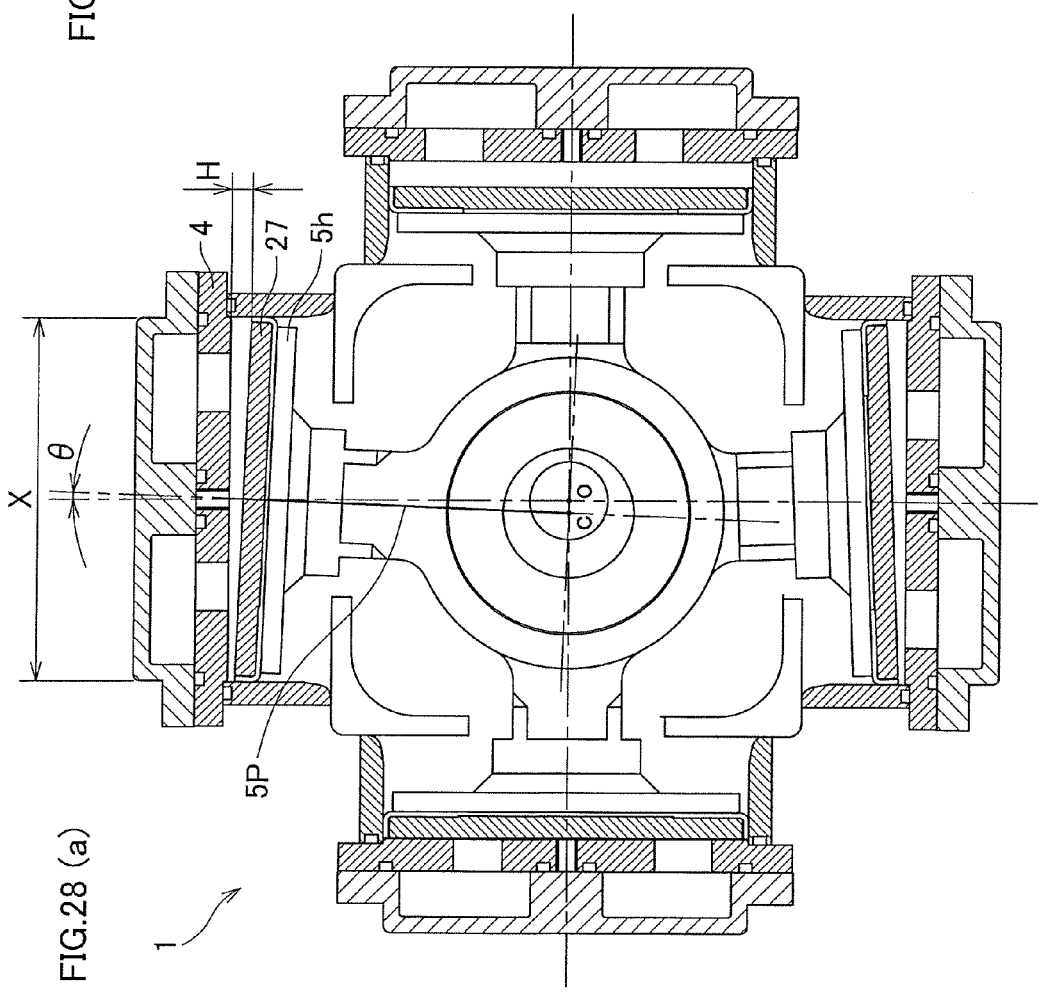

FIG. 28 is an explanatory view of a piston rod, where (a) is an overhead schematic view of a reciprocating compressor, (b) is an overhead schematic view of a piston.

Figure 29:
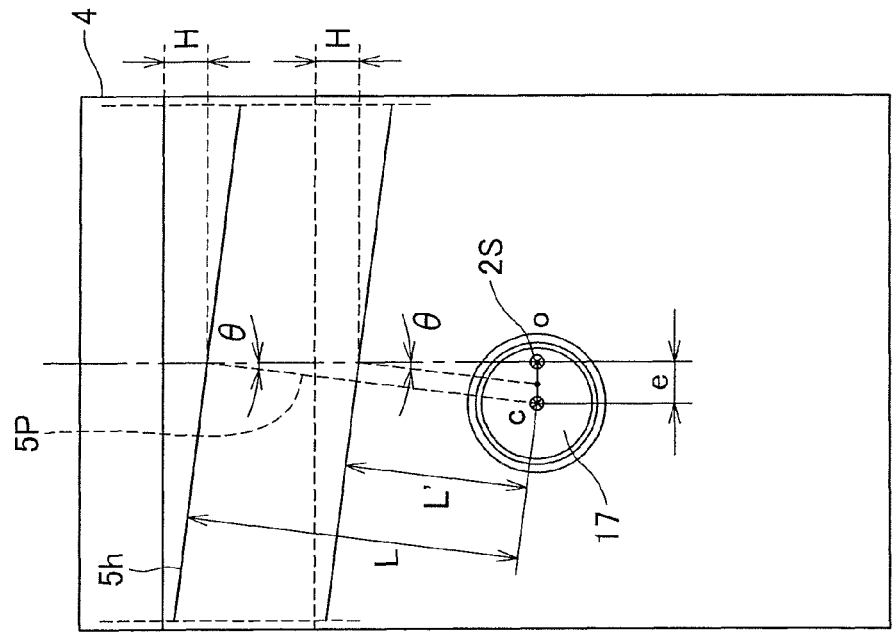
FIG. 29 is an explanatory view of an angle of oscillation and a sliding distance of a piston, where (a) is a model diagram illustrating a case where an eccentric distance is constant, and (b) is a model diagram illustrating a case where the eccentric distance is not constant.
Figure 29:
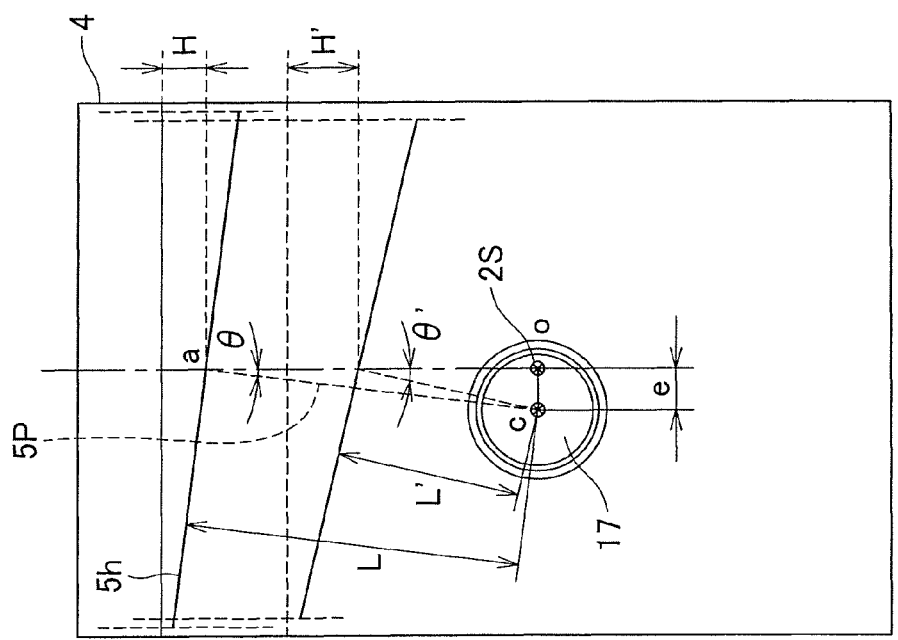

FIG. 29 is an explanatory view of an angle of oscillation and a sliding distance of a piston, where (a) is a model diagram illustrating a case where an eccentric distance is constant, and (b) is a model diagram illustrating a case where the eccentric distance is not constant.

Figure 30:
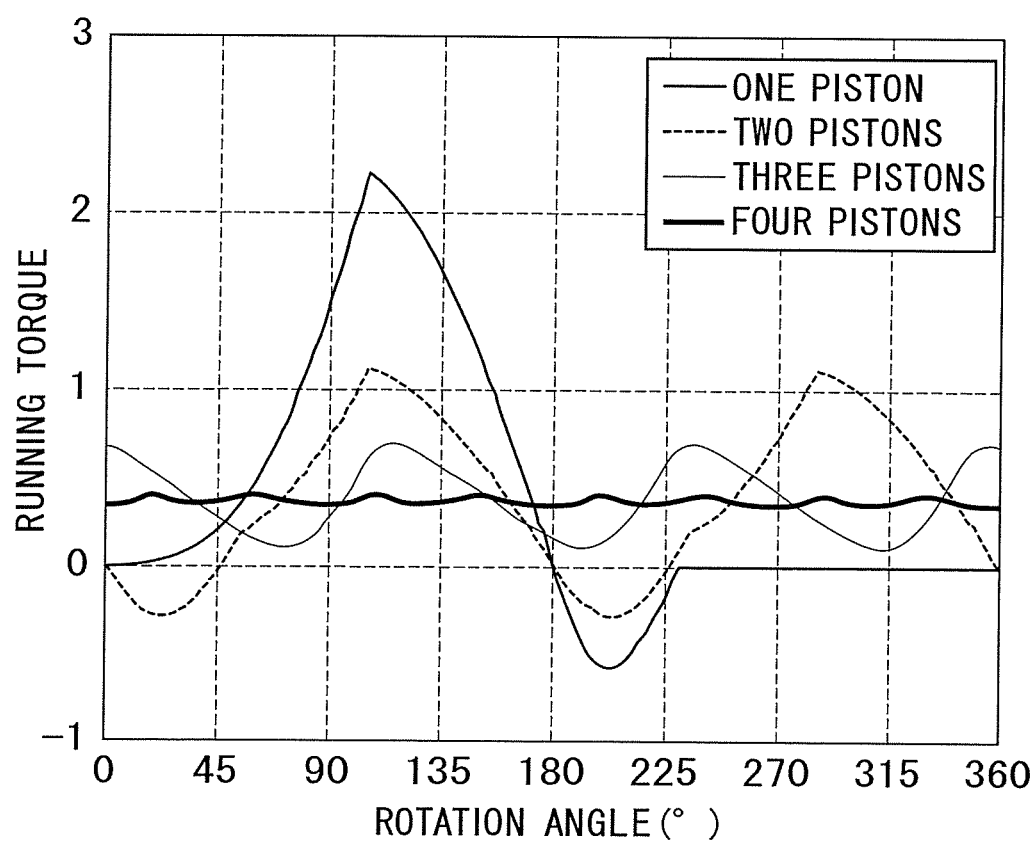
FIG. 30 is an explanatory view illustrating fluctuations in running torque of a motor shaft when the number of cylinders is changed.

FIG. 30 is an explanatory view illustrating fluctuations in running torque of a motor shaft when the number of cylinders is changed.

Figure 31:
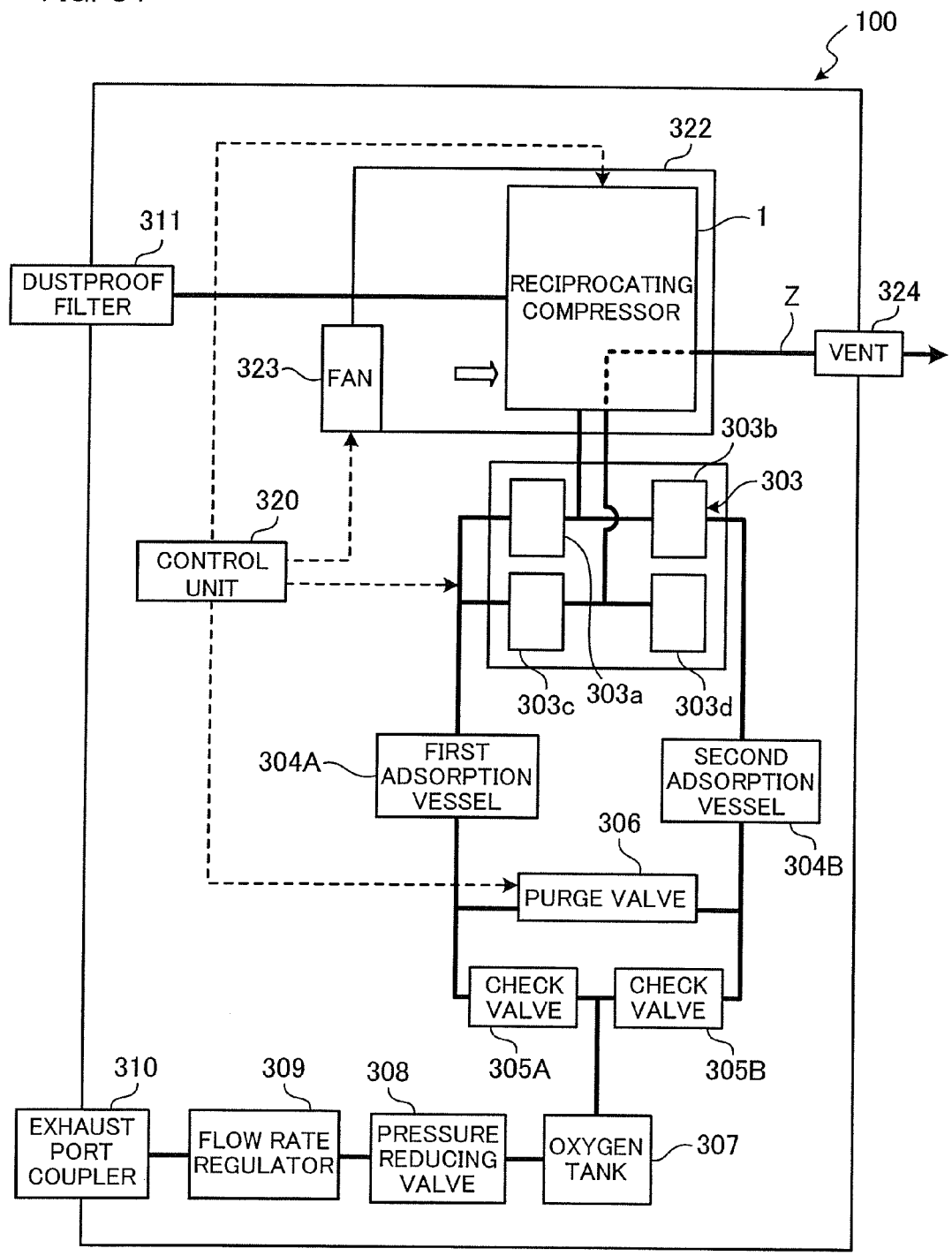
FIG. 31 is a block diagram of an oxygen concentrator having the reciprocating compressor of FIG. 1.

FIG. 31 is a block diagram of an oxygen concentrator having the reciprocating compressor of FIG. 1.

Figure 32:
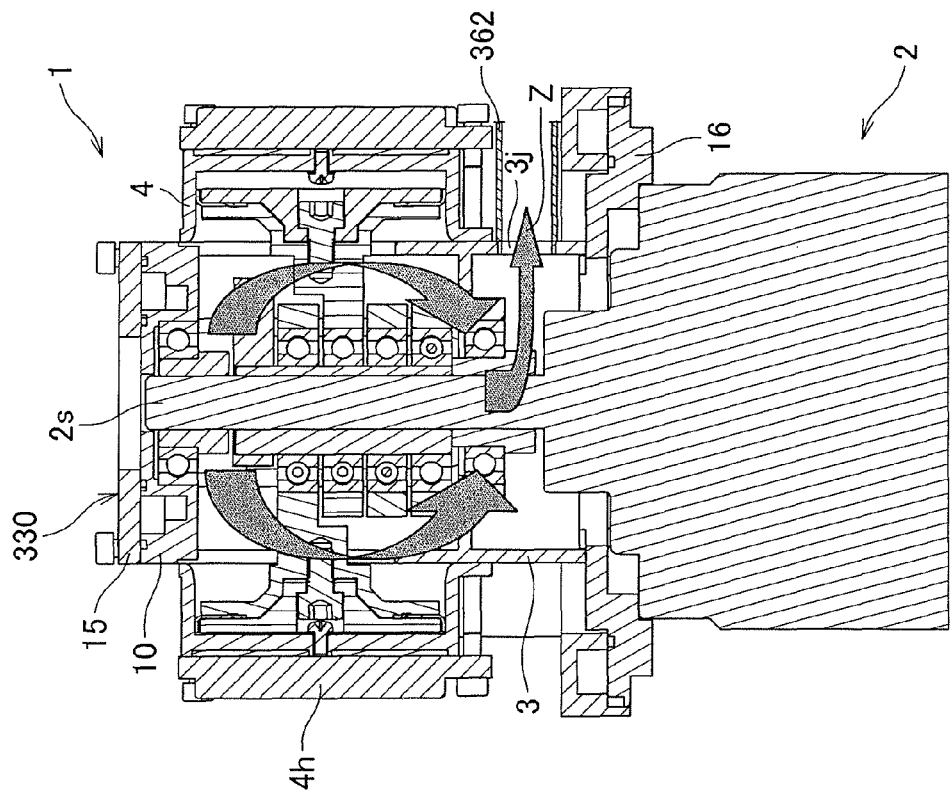
FIG. 32 is an explanatory view illustrating air circulation in the reciprocating compressor in FIG. 1, where
Figure 32:
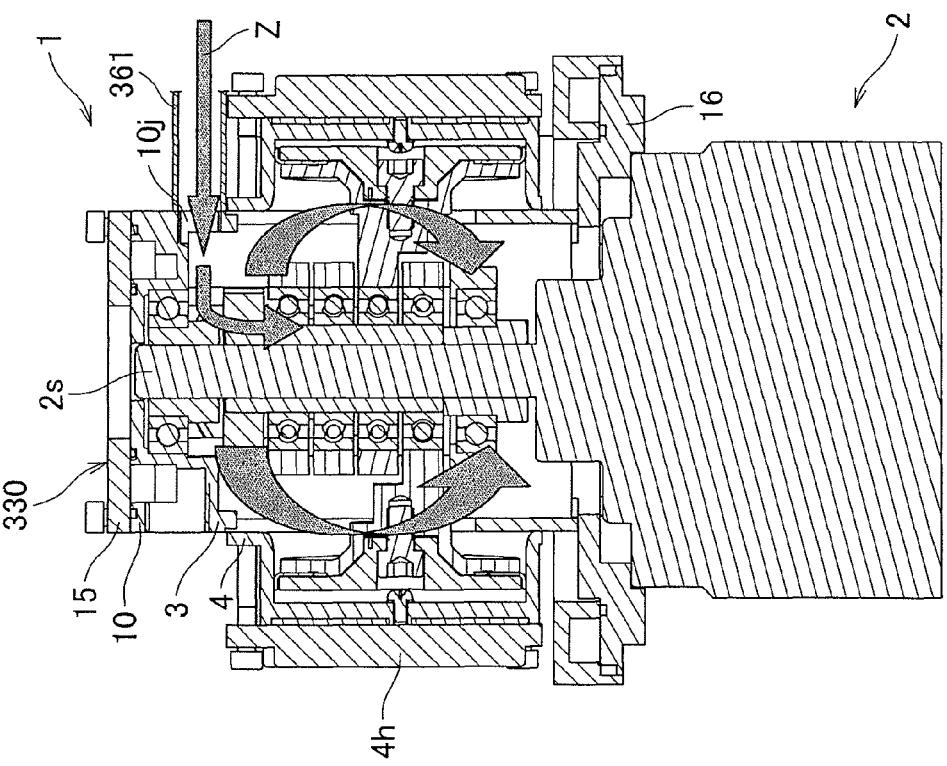

FIG. 32 is an explanatory view illustrating air circulation in the reciprocating compressor in FIG. 1, where FIG. 32($a$) is a longitudinal cross-sectional view illustrating a cooling inlet, and FIG. 32($b$) is a longitudinal cross-sectional view illustrating a cooling vent.

Note that FIGS. 3 to 5 each illustrate a side view of a motor, and a cross-sectional view of parts other than the motor.

(Whole Structure)

The following first describes a whole structure of a reciprocating compressor 1 according to the present embodiment. In the present embodiment, the reciprocating compressor 1 is employed as a compressor which admits and compresses a gas fluid (air) in an oxygen concentrator or the like for generating highly-concentrated oxygen. Although an illustration is omitted, the oxygen concentrator compresses admitted air with the reciprocating compressor 1, causes the compressed air to contact synthetic zeolite having nitrogen adsorbability, and exhausts highly-concentrated oxygen.

The reciprocating compressor 1 includes: a motor 2; a casing 3; four cylinders 4; four pistons 5; a plurality of intake passages 6; a plurality of exhaust passages 7; a shared intake passage 9; a shared exhaust passage 8; and a bearing support member 10. The air admitted flows through the shared intake passage 9 and the intake passages 6 to the four cylinders 4. After the air is compressed in the cylinders 4, the air flows through the exhaust passages 7 and the shared exhaust passage 8, and is eventually exhausted outside the reciprocating compressor 1. The following describes a structure of each part.

(Motor)

The motor 2 includes a motor shaft 2$s$ and a main body part 2$b$ (see FIG. 3). The reciprocating compressor 1 has one motor, and the one motor 2 drives the four pistons 5 (described later in detail). The motor shaft 2$s$ is an output shaft of the motor 2, and is supported by a shaft holder 2$h$ as illustrated in FIG. 3. The motor shaft 2$s$ is rotatably supported by a bearing 22$a$ and a bearing 22$b$, the bearing 22$a$ being provided inside the casing 3, and the bearing 22$b$ being provided to an shaft end portion 2$t$ of the motor shaft 2$s$ and supported by a bearing support plate 10. Further, installed to the motor 2 is a later-described first member 3$f$ of the casing 3, which first member 3$f$ accommodates the motor shaft 2$s$.

(Casing)

The casing 3 is for accommodating the motor shaft 2$s$ and the like. The motor 2 is attached to one end of the casing 3 via a flange 16. The casing 3 includes a first member 3$f$ and a second member 3$s$ (see FIGS. 22 and 23). The first member 3$f$ and the second member 3$s$ are separately formed. The first member 3$f$ has higher thermal conductivity than the second member 3$s$. Specifically, the first member 3$f$ is made of metal, and the second member 3$s$ is made of resin. Note that the materials of the first member 3$f$ and the second member 3$s$ are not limited to these. For example, the second member 3$s$ may be a metal member having lower thermal conductivity than the first member 3$f$. Alternatively, the first member 3$f$ and the second member 3$s$ may be made of the same material. Further, the second member 3$s$ may have higher thermal conductivity than the first member 3$f$. The following describes the first member 3$f$ and the second member 3$s$.

(First Member)

The first member 3$f$ functions as a typical casing. The first member 3$f$ is metallic, as described above, and functions as a frame member surrounding the motor shaft 2$s$ in the reciprocating compressor 1. Further, the first member 3$f$ has four reinforce portions 3$w$. The reinforce portions 3$w$ each extend in a motor shaft direction (see FIGS. 11 to 13). More specifically, the first member 3$f$ has four groove portions 3$r$ respectively on four walls of a rectangular tube extending in the motor shaft direction when attached to the motor 2. As a result, each wall of the first member 3$f$ has a U-shape in front view. Further, each of the four corner portions of the first member 3$f$ is provided with a reinforce portion 3$w$ extending in the motor shaft direction. A connecting part 5$c$ of each of the four pistons 5 (see FIG. 21) fits into one of the four groove portions 3$r$ formed between the four reinforce portions 3$w$. Later-described protrusions 10$z$ and 10$w$ each fit into one of the four groove portions 3$r$ (see FIGS. 15 and 16). Further, a motor through hole 3$d$ is provided to a center portion in plan view of a bottom plate portion 3$q$ of the first member 3$f$ (FIG. 12($a$) and ($c$)). The motor through hole 3$d$ is for the motor shaft 2$s$ and the like of the motor 2 to penetrate therethrough. Further, inside the first member 3$f$ is a part of the exhaust passages 7 provided (described later in detail). The bearing 22$a$ is attached to the first member 3$f$.

The exhaust passages 7 each have a first parallel portion 7$f$ extending in the axial direction of the motor shaft 2$s$ (see FIGS. 13, 4, and 6). The first parallel portions 7$f$ are provided inside the casing 3. Further, the first member 3$f$ is provided with a total of four exhaust entrances 3$x$ respectively corresponding to the four cylinders 4. The four exhaust entrances 3$x$ are each connected to the inside of the corresponding one of the cylinders 4 (see FIGS. 4 and 7). Further, there are two parallel portions 7$f$ provided to the first member 3$f$. One parallel portion 7$f$ is provided to one corner portion of the first member 3$f$, and the other parallel portion 7$f$ is provided to another corner portion nonadjacent to the one corner portion of the first member 3$f$. The two corner portions face one another across the motor shaft 2$s$ (see FIG. 6). The first parallel portions 7$f$ are each provided with two exhaust entrances 3$x$. In other words, the first parallel portions 7$f$ each serve as a common passage of air exhausted from two corresponding cylinders 4. Specifically as illustrated in FIG. 6, the upper left first parallel portion 7$f$ is connected to the inside of the upper and left cylinders 4. The lower right parallel portion 7$f$ is connected to the inside of lower and right cylinders 4.

The two first parallel portions 7f are respectively provided to the upper left and lower right corner portions among the four corner portions of the first member 3 in FIG. 6. The upper right and lower left corner portions among the four corner portions of the first member 3f are respectively provided with two passages 106 (see FIG. 5); however, the passages 106 are not utilized in the present embodiment. Note that two of the exhaust entrances 3x among the total of four exhaust entrances 3x are respectively denoted by 3x(a) and 3x(b) in FIGS. 11 to 13 in order to clarify correspondence between each figure.

Air compressed and exhausted in the cylinders 4 is supplied to the first parallel portions 7f through the exhaust entrances 3x respectively corresponding to the cylinders 4 (see FIG. 4). Each of the passages is provided to the inside of a reinforce portion 3w serving as a frame of the casing 3 in the present embodiment. This ensures a reinforcing function of the casing while avoiding a large casing, thus efficiently utilizing the casing. Further, the four exhaust entrances 3x respectively corresponding to the four cylinders 4 are provided to a pair of diagonally opposing corner portions, as illustrated in FIG. 4. Thus, when heat of the head is to be dissipated with an external cooling device such as a blower or a fan, the four cylinders 4 do not have to be individually cooled. Thus, this allows efficient cooling.

Further, a side portion of the first member 3f is provided with a cooling vent 3j (see FIGS. 11 and 12). The cooling vent 3j is for exhausting a cooling medium from a later-described exhaust gas passage Z (see FIG. 32).

(Second Member)

The second member 3s is made of resin, as described above. The second member 3s includes: an annular part 3t; two column members 3v attached to the annular part 3t; and an intake protrusion 3u (see FIGS. 9 and 10). The two column members 3v and the intake protrusion 3u extend in the axial direction of the motor shaft 2s when the second member 3s is attached to the motor 2 (see FIG. 10(a)). Inside each of the two column members 3v is a part of the intake passages 6 (described later in detail). Inside the annular part 3t is a shared intake passage 9 (see FIGS. 10(a) and (b), FIG. 3, and the like). The intake protrusion 3u is provided with an inlet 3z. Air flown in through the inlet 3z is supplied to the shared intake passage 9 (see FIGS. 4, 10(c), and the like).

Further, the intake passages 6 each include a second parallel portion 6f extending in the axial direction of the motor shaft 2s (see FIG. 10, and FIGS. 5 to 7). Further, the second member 3s is provided with a total of four intake exits 3y respectively corresponding to the four cylinders 4. Each of the intake exits 3y is connected to the inside of the corresponding cylinder 4 (see FIGS. 6, 10(b), and the like). Further, there are two second parallel portions 6f provided to the second member 3s. The second parallel portions 6f are disposed facing one another across the motor shaft 2s (see FIGS. 6, 10(b), and the like). The second parallel portions 6f are each provided with two of the intake exits 3y. In other words, the second parallel portions 6f each serve as a common passage of air supplied to two corresponding cylinders 4 (see dashed line in FIG. 10(b) illustrating an intake passage 6). Specifically as illustrated in FIG. 6, the upper right second parallel portion 6f is connected to the inside of the upper and right cylinders 4. The lower left second parallel portion 6f is connected to the inside of the lower and left cylinders 4. Further, each of the two second parallel portions 6f is provided so as to face a corner portion of the first member 3f; however, the corner portions of the first member 3f facing the two second parallel portions 6f (upper right and lower left corner portions in FIG. 6) are different from the corner portions where the first parallel portions 7f are provided (upper left and lower right corners in FIG. 6). Thus, the intake passages 6 and the exhaust passages 7 are separated. This prevents heat of the exhaust passages 7 from transferring to the intake passages 6.

Further, in the reciprocating compressor 1, the column members 3v of the second member 3s are each provided between neighboring ones of the four cylinders 4 (i.e. provided at respective corner portions in FIG. 6). The four cylinders 4 are disposed at ninety-degree intervals in plan view relative to a circumferential direction of the motor shaft 2s (see FIGS. 6 and 7). Further, a maximum distance between a center of the motor shaft 2s and a column member 3v is substantially equal to a maximum distance between the center of the motor shaft and a head cover 4h. The column members 3v fall within a quadrangle formed with straight lines along outer surfaces of the four head covers 4h in plan view (see T in FIG. 6). This allows efficient utilization of spaces between the cylinders 4, thus avoiding a large casing.

(Shared Intake Passage)

The shared intake passage 9 provided to the inside of the annular member 3t is for uniting the intake passages 6. The shared intake passage 9 is an annular passage around an axial region 31 which extends in the axial direction of the motor shaft 2s (see FIG. 27). The shared intake passage 9 is provided overlapping a peripheral region 32 of the axial region 31 which extends in the axial direction of the motor shaft 2s (see FIG. 27). This arrangement is described later in detail. Further, the shared intake passage 9 is a space enclosed by a combination of the second member 3s and the later-described flange 16 (see FIGS. 3 to 5). Further, the shared intake passage is not required to be an annular passage, but may be a massive form, for example. Further in the present embodiment, a center of the circle of the shared passage 9 matches the center of the motor shaft 2s. This allows a balanced arrangement around the motor shaft 2s from a size-reducing perspective. When the shared intake passage is annular, however, the center of the circle of the shared intake passage does not necessarily match the center of the motor shaft, but the centers may be offset.

(Cylinder)

There are four cylinders 4 provided in the present embodiment. The four cylinders 4 are each provided so that axial directions of the cylinders (directions indicated by arrows in FIG. 6) are perpendicular to the axial direction of the motor shaft 2s. Further in plan view, two of the cylinders 4 are provided on one straight line passing through the center of the motor shaft 2s, and the other two of the cylinders 4 are provided on another straight line which is perpendicular to the one straight line and passes through the center of the motor shaft 2s (see FIGS. 6, 28, and the like). The four cylinders 4 each have a compression chamber 4j (cylinder interior) (see FIG. 17 and the like). The cylinders 4 each include: a main body part 4a extending in the axial direction of the cylinder; and a sheet plane member 4p fixed to one end of the main body part 4a. Part of the plane member 4p serves as part of a wall facing the compression chamber 4j (see FIG. 17(c)). The main body part 4a and the plane member 4p are fixed together by six bolts, which bolts are for attaching the later-described head cover 4h to the cylinder 4. The main body part 4a and the plane member 4p have an elastic member 4A therebetween (see FIG. 3). The annular elastic member 4A is not required between the main body part 4a and the plane member 4p. Further, the elastic member 4A is not required to be annular. The plane member 4p has four through holes 4b, 4c, 4f, and 4g formed thereon. The plane member 4p further has a groove portion 4m formed thereon (see FIG. 17). The main body part 4a has an inner diameter (bore diameter) X (see FIG. 28(a)).

To each of the cylinders 4 are attached members such as those illustrated in FIG. 18. Specifically, an exhaust valve 4w, an exhaust valve gland 4z, and an intake valve 4v, are attached to the cylinder 4 by fixing screws 20a and a washers 20b. The intake valve 4v is provided to a compression chamber 4j side inside the cylinder 4. The exhaust valve 4w and the exhaust valve gland 4z are provided to exterior of the cylinder 4 (see FIGS. 18 and 6). The intake valve 4v is normally closed, but deforms and opens when pressure of air passing through the through hole 4c becomes a predetermined magnitude or more. Further, the exhaust valve 4w is normally closed, but deforms and opens when pressure of air passing through the through hole 4f becomes a predetermined magnitude or more (while the exhaust valve gland 4z limits an maximum angle of deformation).

Further, a head cover 4h is attached to each of the cylinders 4 by the six bolts (see FIGS. 19 and 20). The head cover 4h has an internal space and a partition part 4s. The internal space of the head cover 4h is divided into a first room 4n and a second room 4k by the partition part 4s. Here, the first room 4n is a space where air before supplied to the compression chamber 4j flows through. The second room 4k is a space where air exhausted from the compression chamber 4j flows through. Further, the head cover 4h is attached to the cylinder 4 at a leading end portion of the partition part 4s with a cylinder packing 20e therebetween, the cylinder packing 20e fitting into a groove portion 4m of the cylinder 4 (see FIG. 24). When the head cover 4h is attached to the cylinder 4, the partition part 4s and the groove portion 4m are hermetically sealed by the cylinder packing 20e, and the first room 4n and the second room 4k become closed spaces by the head cover 4h and the plane member 4p inside the head cover 4h (except when the exhaust valve 4w or the intake valve 4v is open) (see FIG. 7).

The following describes a state where the head cover 4h is attached to the cylinder 4. The through hole 4b is connected to the corresponding intake exit 3y of the second member 3s. The air flown through a corresponding one of the second parallel portions 6f is supplied to the first room 4n through the through hole 4b (see FIG. 6). The through hole 4c is for air introduced through the through hole 4b to flow therethrough. The air in the first room 4n is supplied to the compression chamber 4j through the through hole 4c (see FIG. 6). Further, the through hole 4f is for compressed air exhausted from the compression chamber 4j to flow therethrough. The compressed air flows through the through hole 4f, and on the inside of the second room 4k, the compressed air is supplied to the through hole 4g (see FIG. 18). The through hole 4g is connected to a corresponding one of the exhaust entrances 3x of the first member 3f. The compressed air exhausted is sent to the first parallel portion 7f through the through hole 4g and the corresponding exhaust entrance 3x (see FIG. 7). Further, the internal space of the head cover 4h (exterior of the plane member 4p) constitutes part of the corresponding one of the intake passages 6 and part of the corresponding one of the exhaust passages 7. Thus, air circulation in the intake passage 6 and the exhaust passage 7 in the internal space of the head cover 4h (exterior of the plane member 4p) is as indicated by dashed lines in FIG. 18. Thus, air intake, compression, and exhaust are performed inside the cylinder 4 constituted as described above.

(Piston)

The four pistons 5 are respectively provided to the inside of the four cylinders 4 (see FIGS. 3 to 7 and the like). The reciprocating compressor 1 according to the present embodiment is provided with four pistons 5 corresponding to the four cylinders 4. The pistons 5 each have a piston head part 5h and a rod part 5R formed integrally, as illustrated in FIG. 21(a).

The piston head part 5h reciprocally fits into the cylinder 4. The rod part 5R is rotatably installed to an eccentric shaft 17 fixed to the motor shaft 2s. The rod part 5R is composed of a connecting part 5c and a ring part 5r. A seal member 28 and a retainer plate 27 provided to the piston head part 5h have a spacer 30 therebetween as illustrated in FIG. 21(b). The seal member 28, the retainer plate 27, and the spacer 30 are fixed to the piston head part 5h with one bolt 29. Note that the eccentric shaft 17 is provided with a bearing 17b disposed inside the rod part 5R.

In each of the four pistons 5, a piston rod 5P has a length L which is a distance between an end surface 27s of the retainer plate 27 and a center of the ring part 5r of the piston 5, as illustrated in FIGS. 28(a) and 28(b), the piston rod 5P being on a straight line corresponding to a central axis of the piston head part 5h. An angle of oscillation of each piston 5 is indicated by an angle of slope θ of the piston rod 5P with respect to a cylinder axis in plan view, as illustrated in FIG. 28(a). In the present embodiment, the angle of oscillation of each piston 5 is maximum when the motor shaft 2s rotates by ninety degrees. The four pistons 5 each slide inside the cylinder 4 to make intake and compression strokes, while maintaining a ninety-degree phase difference with each other.

Each of the four pistons 5 is assembled as illustrated in FIG. 23. Specifically as illustrated in FIG. 21(a), the ring parts 5r of the four pistons 5 are sequentially installed. The balance weight 18 is also installed to the eccentric shaft 17. At this time, each of three adjust members 34 is provided between neighboring ones of the ring parts 5r of the four pistons 5 in the axial direction of the motor shaft 2s, in order to adjust positions of the pistons 5.

(Bearing Support Member)

The bearing support member 10 illustrated in FIGS. 14 to 16 is provided to the shaft end portion 2t of the motor shaft 2s (see FIGS. 3 to 5, and FIG. 26). The bearing support member 10 is for rotatably supporting the motor shaft 2s via the bearing 22b. The bearing support member 10 is provided with a shared exhaust passage 8 (see FIGS. 14 to 16). The bearing support member 10 has a bearing hole 10k formed at its center portion. The shaft end portion 2t of the motor shaft 2s fits into the bearing hole 10k (see FIG. 3). A protruding part 10w is provided to one side portion of the bearing support member 10. A protruding part 10z is provided to another side portion facing the one side portion of the bearing support member 10. The protruding parts 10w and 10z each extend in the axial direction of the motor shaft 2s (when assembled into the reciprocating compressor 1). The protruding parts 10w and 10z respectively have a vent 10h and a cooling inlet 10j (see FIGS. 14 to 16). Compressed air gathering in the shared exhaust passage 8 is eventually exhausted through the vent 10h (see FIG. 16(a)). The cooling inlet 10j is for admitting the cooling medium into the later-described exhaust gas passage Z (see FIG. 32). Corner portions of the bearing support member 10 are each provided with one of two exhaust inlets 10i. The exhaust inlets 10i each constitute part of an exhaust passage 7. The two exhaust inlets 10i are each connected to the shared exhaust passage 8. Each of the exhaust passages 7 continues to the shared exhaust passage 8 through a corresponding one of the exhaust inlets 10i (see FIGS. 4, 16, and the like).

(Shared Exhaust Passage)

The shared exhaust passage 8 formed inside the bearing support member 10 is for uniting the exhaust passages 7. The shared exhaust passage 8 is an annular passage around the axial region 31 extending in the axial direction of the motor shaft 2s (see FIG. 27). The shared exhaust passage 8 is provided so as to overlap the peripheral region 32 of the axial region 31 which extends in the axial direction of the motor shaft 2s. This arrangement is described later in detail. Further, the shared exhaust passage 8, which is an annular passage, extends two-dimensionally along a plane 33 perpendicular to the axial direction of the motor shaft 2s (see FIGS. 14 and 27). Further, the shared exhaust passage 8 is a space enclosed by a combination of the bearing support member 10 and the casing cover 15 (see FIGS. 3 to 5). Note that the shared exhaust passage is not required to be an annular passage. Further in the present embodiment, a center of the circle of the shared exhaust passage 8 matches the center of the motor shaft 2s. This achieves a balanced arrangement around the motor shaft 2s from a size-reducing perspective. The center of the circle of the shared intake passage, however, does not necessarily match the center of the motor shaft when the shared exhaust passage is annular: The centers may be offset. Further in the present embodiment, the shared exhaust passage 8, which is an annular passage, two-dimensionally extends along the plane 33 perpendicular to the axial direction of the motor shaft 2s. The shared exhaust passage 8, however, is not limited to this: The shared exhaust passage 8 may two-dimensionally extend along a plane inclined with respect to the plane 33. Alternatively, the shared exhaust passage 8 may not two-dimensionally extend but axially extend, for example. Further, the shared exhaust passage is not necessarily provided to the bearing support member: An additional member for the shared exhaust passage may be provided aside from a member such as the bearing support member. Providing the shared exhaust passage 8 to the bearing support member 10 as in the present embodiment can prevent an increase in the number of members.

The bearing support member 10 is provided only with the shared exhaust passage 8 in the present embodiment; however, at least one of the shared exhaust passage and the shared intake passage may be provided to the bearing support member. Thus, the structure is not limited thereto. For instance, only the shared intake passage may be provided to the bearing support member. Alternatively, both the shared exhaust passage and the shared intake passage may be provided to the bearing support member.

(Positional Relation between Shared Intake Passage and Shared Exhaust Passage)

The following describes a positional relation between the shared intake passage 9 and the shared exhaust passage 8 with reference to FIG. 27 and the like. First, the shared intake passage 9 and the shared exhaust passage 8 are provided to sandwich the four cylinders 4 therebetween in the axial direction of the motor shaft (see FIGS. 3 to 5). The shared exhaust passage 8 is provided to the shaft end portion 2t side of the motor shaft 2s. The shared intake passage 9 is provided to the main body part 2b side of the motor shaft 2s.

Further, each of the shared intake passage 9 and the shared exhaust passage 8 is annular, and the center of the circle of each of these passages matches a center of circle of the motor shaft 2s. Further, both the shared intake passage 9 and the shared exhaust passage 8 are provided so as to overlap at least one of the axial region 31 extending in the axial direction of the motor shaft, and the peripheral region 32 thereof. To "overlap" here means that the shared intake passage 9 or the shared exhaust passage 8 is provided so as to fall within a region composed of the axial region 31 and the peripheral region 32, as illustrated in FIG. 27. The shared intake passage 9 and the shared exhaust passage 8 fall within a width of the region composed of the axial region 31 and the peripheral region 32 (see width W1 in FIG. 27) with respect to a radial direction. In the present embodiment, the width W1 is substantially equal to a diameter of the flange 16. Further, the shared intake passage and the shared exhaust passage preferably fall within a width of the main body part 2b of the motor 2 (see width W2 in FIG. 27). The shared exhaust passage 8 according to the present embodiment falls within the width. This avoids a compressor large in the radial direction perpendicular to the axial direction. Further, each of the shared intake passage 9 and the shared exhaust passage 8 has a part overlapping the motor shaft 2s with respect to the axial direction of the motor shaft 2s. This avoids a compressor large in the axial direction as well.

In the present embodiment, the shared exhaust passage 8 is provided to the shaft end portion 2t side of the motor shaft 2s, while the shared intake passage 9 is provided to the main body part 2b side. However, the arrangement may be reversed, as long as the shared exhaust passage 8 and the shared intake passage 9 are provided to the respective sides of the motor shaft 2s. Further, the shared exhaust passage and the shared intake passage are not required to be provided to sandwich of the cylinders 4. The shared exhaust passage and the shared intake passage may be provided to the same side with respect to the cylinders 4 relative to the axial direction of the motor shaft 2s.

Both the shared intake passage 9 and the shared exhaust passage 8 are provided inside the peripheral region 32 in the present invention. However, it is required that only one of the shared exhaust passage and the shared intake passage is provided overlapping at least one of the axial region 31 extending in the axial direction of the motor shaft and the peripheral region 32. Thus, only one of the shared exhaust passage and the shared intake passage may fall within a region composed of the axial region 31 and the peripheral region 32 (radial region within the width W1), and the other may be formed protruding from the region composed of the axial region 31 and the peripheral region 32. Further, an non-annular shared exhaust passage or an non-annular shared intake passage may be formed not overlapping the motor shaft 2s with respect to the motor shaft direction, but overlapping with the axial region 31 and the peripheral region 32 (to fall within the region of the width W1 in the radial direction).

(Intake Passage)

The following describes the intake passages 6. As described above, the intake passages 6 pass through the inside of the second member 3s. The intake passages 6 each allow a fluid to circulate therethrough. Further, the intake passages 6 are respectively connected to the inside of the cylinders 4 (compression chambers 4j) (see the dashed lines in FIG. 6 indicating the intake passages 6).

First, air flows inside the second member 3s through the inlet 3z of the second member 3s, then flows into the shared intake passage 9 (see FIGS. 4 and 10). The following describes each of the intake passages 6; i.e., passage to the inside of each of the cylinders 4 (compression chamber 4j). The interior of the second member 3s is structured so that the shared intake passage 9 continues to the two second parallel portions 6f. Air inside the shared intake passage 9 is supplied to the two second parallel portions 6f (see FIGS. 5 and 10). The air flown through each of the second parallel portions 6f is then supplied through the intake exit 3y and the through hole 4b into the first room 4n (see FIGS. 6, 10, and the like). Then, the air in the first room 4n is supplied to the compression chamber 4j through the through hole 4c. Each of the intake passages 6 is constituted as described above.

(Exhaust Passage)

The following describes the exhaust passages 7. As described above, the exhaust passages 7 pass through the inside of the first member 3f. The exhaust passages 7 each allow a fluid (air in the present embodiment) to circulate therethrough. Further, the exhaust passages 7 are respectively connected to the inside of the four cylinders 4 (compression chamber 4j) (see dashed lines in FIG. 4 indicating the exhaust passages 7).

The following describes each of the exhaust passages 7; i.e., a passage from inside of a cylinder 4 (compression chamber 4j) to the vent 10h. First, air compressed in the compression chamber 4j inside the cylinder 4 flows through the through hole 4f and inside the second room 4k into the through hole 4g (see. FIG. 18). The compressed air flown through the through hole 4g is then sent to the exhaust entrance 3x of the first member 3f, then supplied to a corresponding one of the first parallel portions 7f (see FIG. 7). The compressed air then flows through the first parallel portion 7f and flows into the exhaust inlet 10i of the bearing support member 10 (see FIG. 4). Each of the exhaust passages 7 is constituted as described above. The compressed air flown from the (four) exhaust passages 7 then flows through the exhaust inlet 10i into the shared exhaust passage 8 (see FIG. 16), and is eventually exhausted through the vent 10h.

Note that in the present embodiment, the reciprocating compressor 1 includes four exhaust passages 7 and four intake passages 6. Here, each of the first parallel portions 7f is a passage common to two exhaust passages 7 among the four exhaust passages 7, and each of the second parallel portions 6f is a passage common to two intake passages 6 among the four intake passages 6. Despite the partial common passages the exhaust passages 7 and the intake passages 6 have, it is considered that there are four exhaust passages 7 and four intake passages 6.

Further, the four exhaust passages 7 each include a divergence passage 7s provided in the direction of gravity (see FIG. 4). The divergence passages 7s each have an adhesive 7A provided thereto. Thus, wear particles of the seal member 28 produced by oscillation of the pistons 5 adhere to the adhesive 7A. This prevents emission of the wear particles to outside of the reciprocating compressor 1. Note that in the present embodiment, each of the first parallel portions 7f is provided in the direction of gravity as each of the divergence passages 7s is. Thus, the adhesive 7A (see FIG. 4) is able to prevent emission of wear particles to outside of the reciprocating compressor 1.

(Assembly of Reciprocating Compressor)

The following describes assembly of the reciprocating compressor 1. First, the flange 16 and the casing 3 (the first member 3f and the second member 3s) are attached to the motor 2 (see FIG. 22). Here, the flange 16 and the second member 3s have rubber O-rings 20c and 20d therebetween (see FIGS. 22 and 3 to 5) in order to ensure airtightness. Note that the flange 16 is for mounting the casing 3 to the motor 2. The flange 16 also serves as a fix support member when attaching the reciprocating compressor 1 to a housing of an oxygen concentrator. In the present embodiment, the annular part 3t of the second member 3s is formed to fit the size of the flange 16. This ensures a size of the flange 16 necessary to function as a fix support member, while avoiding a large compressor.

Then, the four pistons 5 are installed (see FIG. 23). Here, the four pistons 5 are installed to the eccentric shaft 17 with the balance weight 18 and the adjust members 34, as illustrated in FIG. 21(a). The adjust members 34 are able to adjust a position of the rod part 5R of each of the four pistons 5, to easily match an axial center of each of the cylinders 4 and an axial center of the piston head part 5h of the corresponding piston 5. This prevents lopsided wear of the seal member 28.

Next, the four cylinders 4 are installed (see FIG. 24). Specifically, the cylinders 4 are each installed so as to cover a piston 5. A head cover 4 is attached to each of the cylinders 4. The cylinders 4 here each have an intake valve 4v and an exhaust valve 4w described in FIG. 18 attached thereto. The cylinder 4 and the head cover 4h have the cylinder packing 20e therebetween in order to ensure airtightness. Further, the head cover 4h is attached to the cylinder 4 with a plurality of fixing bolts 20h and 20i. Further, an O-ring 20f for ensuring airtightness is attached to each of the exhaust entrances 3x. Note that FIG. 24 illustrates only one cylinder 4.

Here, as illustrated in FIG. 25, when the casing 3 has first positioning parts 3B formed thereon, and the four cylinders 4 each have a second positioning part 4B formed thereon corresponding to a first positioning part 3B, the cylinders 4 are each positioned with respect to the casing 3 by the second positioning part 4B and a corresponding one of the first positioning parts 3B in such a way that the axial center of each of the four cylinders 4 matches the axial center of the piston head part 5h of the corresponding one of the four pistons 5.

The bearing support member 10, the casing cover 15, and the like are installed next (see FIG. 26). Specifically, the motor shaft 2s is inserted into a shaft holder 21, and the shaft holder 21 is inserted into the bearing 22b. Then the bearing support member 10 and the casing cover 15 are attached to the first member 3f with a plurality of fixing bolts 20p. Here, each of the first parallel portions 7f of the first member 3f and the corresponding exhaust inlet 10i of the bearing support member 10 have an O-ring 20j therebetween in order to ensure airtightness. The bearing support member 10 and the casing cover 15 have the packing 20m and an O-ring 20n therebetween in order to ensure airtightness. Note that FIG. 26 illustrates three installed cylinders 4 and another cylinder 4 to be installed. The reciprocating compressor 1 illustrated in FIG. 1 is assembled as described above.

(Relation between Angle of Oscillation of Piston and Length of Piston Rod)

When an eccentric distance between a center C of the eccentric shaft 17 and a center O of the motor shaft 2s is constant, and the length L of the piston rod 5P is shortened to a length L', an angle of oscillation of the piston; i.e., an angle of slope θ of the piston rod 5P increases to θ', as illustrated in FIG. 29(a). Thus, a decrease in the length L of the piston rod 5P leads to a steeper slope of the piston head part 5h with respect to the cylinder 4, thus increasing a gap between the piston head part 5h and the cylinder 4.

On the other hand, when the eccentric distance e between the center C of the eccentric shaft 17 and the center O of the motor shaft 2s is shortened, and the length L of the piston rod 5P is shortened to the length L', substantially the same angle of slope θ of the piston rod 5P is maintained, as illustrated in FIG. 29(b). Thus, despite a decrease in the length L of the piston rod 5P, the slope of the piston head part 5h with respect to the cylinder 4 remains substantially the same. Thus, the gap between the piston head part 5h and the cylinder 4 is maintained. This achieves a compact compressor 1 while ensuring airtightness of the compression chamber 4j in the cylinder 4.

(Relation between Sliding Distance of Piston and Length of Piston Rod)

As illustrated in FIG. 29(a), when the eccentric distance e between the center C of the eccentric shaft 17 and the center O of the motor shaft 2s is constant, and the length L of the piston rod 5P is shortened to the length L', the angle of slope θ increases to θ', as described above. This causes a slide distance of the piston 5; i.e., a distance H between a center a of the piston head part 5h and the cylinder 4 to be increased to a distance H', as illustrated in FIG. 29(a).

On the other hand, when the eccentric distance e between the center C of the eccentric shaft 17 and the center O of the motor shaft 2s is shortened, and the length L of the piston rod 5P is shortened to the length L', the angle of slope θ of the piston rod 5P remains substantially the same, as described above. This causes the sliding distance of the piston 5; i.e., the distance H between the center a of the piston head part 5h and the cylinder 4 to be maintained at the distance H, as illustrated in FIG. 29(b). Thus, the sliding distance of the piston 5 is maintained constant regardless of a shorter length L of the piston rod 5P. This ensures sealing ability of the seal member 28 for a long period of time, the seal member 28 being provided to the piston 5.

(Running Torque of Motor Shaft)

When the rotation speed of a piston, pressure, and stroke are fixed in the reciprocating compressor 1 having a plurality of cylinders, an inner diameter (bore diameter) X of a piston is changed in order to maintain the same total exhaust flow rate. When the number of cylinders is one, two, or three, running torque of the motor shaft 2s fluctuates as the motor shaft 2s rotates so as to draw wave as illustrated in FIG. 30. The running torque reaches the maximum value when the angle of rotation is substantially 100 degrees, and reaches the minimum value when the angle of rotation is substantially 200 degrees. Meanwhile in the present embodiment where four cylinders are provided, the four pistons 5 each make intake-compression strokes maintaining a ninety-degree phase difference with each other. This balances out a force acting on the piston head part 5h during a compression stroke of the piston 5. Therefore, the running torque of the motor shaft 2s barely fluctuates as the motor shaft 2s rotates, and thus draws a substantial straight line. Thus, a reciprocating compressor having four cylinders is capable of greatly restraining fluctuations in the running torque compared to a reciprocating compressor having one, two, or three cylinders.

(Oxygen Concentrator)

The following describes an oxygen concentrator according to the present embodiment incorporating the reciprocating compressor. The oxygen concentrator is utilized in home oxygen therapy where highly-concentrated oxygen is provided to a patient with respiratory disorders. Note that in the oxygen concentrator according to the present embodiment incorporating the reciprocating compressor, a sealed container 330 includes the casing 3, the cylinders 4 installed to the casing 3, the head covers 4h each covering a cylinder 4, the bearing support member 10 provided to an upper end of the casing 3, and the casing cover 15 attached to the bearing support member 10.

As illustrated in FIG. 31, the oxygen concentrator 100 is provided with an exhaust gas passage Z, as illustrated in FIG. 31. A nitrogen-containing gas (cooling medium) exhausted from adsorption containers 304A and 304B by gas exhaust members 303c and 303d, is introduced to the sealed container 330 of the reciprocating compressor 1 and is exhausted to outside through the exhaust gas passage Z.

Specifically, the oxygen concentrator 100 includes: a dustproof filter 311; the reciprocating compressor 1; a control valve 303; a first adsorption vessel 304A; a second adsorption vessel 304B; a check valve 305A; a check valve 305B; a purge valve 306; an oxygen tank 307; a pressure-reducing valve 308; a flow rate regulator 309; and an exhaust port coupler 310. The dustproof filter 311 is for removing dust from air admitted from outside. The reciprocating compressor 1 compresses the air admitted through the dustproof filter 311. The control valve 303 is provided to a side of a gas passage, towards which side the compressed air in the reciprocating compressor 1 is exhausted. The first adsorption vessel 304A is an example of an adsorption container which stores an adsorbent which adsorbs nitrogen contained in the compressed air. The second adsorption vessel 304B is an example of an adsorption container which stores an adsorbent which adsorbs nitrogen from the air supplied from the reciprocating compressor 1 through the control valve 303. The check valve 305A is provided to a gas passage downstream of the first adsorption vessel 304A. The check valve 305B is provided to a gas passage downstream of the second adsorption vessel 304B. The purge valve 306 is provided between the gas passages downstream of the first adsorption vessel 304A and the second adsorption vessel 304B. The oxygen tank 307 is connected to the first adsorption vessel 304A and the second adsorption vessel 304B respectively through the check valves 305A and 305B. The pressure-reducing valve 308 depressurizes condensed oxygen gas from the oxygen tank 307. The flow rate regulator 309 is for adjusting flow rate of the condensed oxygen gas supplied from the oxygen tank 307 through the pressure-reducing valve 308. The exhaust port coupler 310 is connected to a not-illustrated cannula for providing a person with the condensed oxygen gas whose flow rate is adjusted by the flow rate regulator 309.

The reciprocating compressor 1 is provided inside a soundproof box 322. A side surface of the soundproof box 322 has a cooling fan 323 mounted thereon. The cooling fan 323 cools the reciprocating compressor 1 in the soundproof box 322. The oxygen concentrator 100 further includes a control unit 320 which controls the control valve 303, the purge valve 306, cooling fan 323, and the like. The control unit 320 drives the motor 2 in the reciprocating compressor 1 (see FIG. 3).

Further, the control valve 303 includes a first port 303a, a second port 303b, a third port 303c, and a fourth port 303d. One end of the first port 303a is connected to a compressed air passage of the reciprocating compressor 1, and the other end to the first adsorption vessel 304A. One end of the second port 303b is connected to the compressed air passage of the reciprocating compressor 1, and the other end to the second adsorption vessel 304B. One end of the third port 303c is connected to the exhaust gas passage Z of the reciprocating compressor 1 and the other end to the first adsorption vessel 304A. One end of the fourth port 303d is connected to the exhaust gas passage Z of the reciprocating compressor 1, and the other end to the second adsorption vessel 304B.

The control unit 320 is composed of a microcomputer, an input/output circuit, or the like, and controls the purge valve 306 and the fan 323. The control unit 320 has a function of a switch control unit which controls a first switch member and a second switch member.

In the oxygen concentrator 100, the control unit 320 operates the reciprocating compressor 1 by causing the first port 303a and the fourth port 303d of the control valve 303 to open, and the second port 303b and the third port 303c to close (pressurization process of the first adsorption vessel 304A, and pressure reduction process of the second adsorption vessel 304B). Then, the reciprocating compressor 1 compresses air admitted through the dustproof filter 311. The air compressed by the reciprocating compressor 1 flows through the first port 303a of the control valve 303 to the first adsorption vessel 304A, where the air is pressurized, and nitrogen in the air is adsorbed by the adsorbent. Highly-concentrated oxygen is thus generated. The highly-concentrated oxygen generated in the first adsorption vessel 304A is stored in the oxygen tank 307 through the check valve 305A. Then, the condensed oxygen gas stored in the oxygen tank 307 is depressurized by the pressure-reducing valve 308. Afterwards, a flow rate of the air is adjusted by the flow rate regulator 309, and the air is then exhausted through the exhaust port coupler 310.

At this time, the second adsorption vessel 304B depressurizes the air to desorb the nitrogen from the adsorbent, and exhausts a gas which contains desorbed nitrogen to outside through the fourth port 303d of the control valve 303 and the reciprocating compressor 1.

During the pressurization process of the first adsorption vessel 304A, the highly-concentrated oxygen generated in the first adsorption vessel 304A is partly supplied to the second adsorption vessel 304B through the purge valve 306. With the pressure in the second adsorption vessel 304B a little higher, the control unit 320 causes the second port 303b and the third port 303c of the control valve 303 to open, and the first port 303a and the fourth port 303d of the control valve 303 to close. Thus, the process is switched to a pressurization process of the second adsorption vessel 304B. Thus, cycles of alternating adsorption and desorption of nitrogen using the adsorbent in the first adsorption vessel 304A and the second adsorption vessel 304B are repeated.

Here, one end of a tube 361 perpendicular to the motor shaft 2s is connected to the reciprocating compressor 1 so as to allow a nitrogen-containing gas to flow into the cooling inlet 10j provided to a side portion of the bearing support member 10 (right side of FIG. 32(a)). An exhaust tube 362 connects a vent 324 and the cooling vent 3j provided to a side portion of the casing 3 (right side of FIG. 32(b)), as illustrated in FIG. 32(b). Note that in the present embodiment, the side portion of the bearing support member 10 where the cooling inlet 10j is provided is circumferentially adjacent to the side portion of the casing 3 where the cooling vent 3j is provided, with respect to the motor shaft 2s.

The tube 361 and the bearing support member 10, and the exhaust tube 362 and the casing 3 constitute the exhaust gas passage Z. The exhaust gas passage Z introduces a nitrogen-containing gas into the sealed container 330 of the reciprocating compressor 1 via the third port 303c and the fourth port 303d of the control valve 303 and exhausts the gas outside thereafter, the nitrogen-containing gas having been exhausted from the first adsorption vessel 304A and the second adsorption vessel 304B of the oxygen concentrator 100 illustrated in FIG. 31. Here, the exhaust gas passage Z is provided to the inside of at least one of the casing 3 and the four cylinders 4.

In the oxygen concentrator 100 having the above structure, due to the exhaust gas passage Z, the nitrogen-containing gas exhausted from the first adsorption vessel 304A and the second adsorption vessel 304B flows into the sealed container 330 of the reciprocating compressor 1 via the tube 361, cools members such as the bearing 17b of the eccentric shaft 17, the bearings 22a and 22b, and the pistons 5, and exits outside thereafter. As illustrated in FIG. 32, the exhaust gas passage Z is formed to extend upward in the sealed container 330 of the reciprocating compressor 1 in the present embodiment. Further, the exhaust gas passage Z is formed through gaps between the four cylinders 4, a gap between the eccentric shaft 17 and the bearing 17b, and a gap between each member provided inside the sealed member 330.

Features of the Present Invention

The reciprocating compressor 1 according to the present embodiment has the following features.

In the reciprocating compressor 1 of the present embodiment, the number of cylinders is increased from two to four. This achieves a shorter stroke while maintaining rotation speed of each piston 5 and a total exhaust flow rate. Thus, the angle of oscillation θ of each of the pistons 5 is maintained in spite of a shortened piston rod 5P. This realizes a compact compressor with airtightness of the compression chambers 4j. Further, a short stroke results in a shorter oscillation distance of the piston head part 5h, thus ensuring the sealing ability of the seal member 28 provided to the piston head part 5h for a long period of time. Further, the four cylinders 4 greatly expand heat dissipating surfaces. This restrains a temperature rise in the compression chambers 4j, thus greatly improving compression efficiency.

Further, two of the cylinders 4 are provided on one straight line passing through the center of the motor shaft 2s, and the other two of the cylinders 4 are provided on another straight line which is perpendicular to the one straight line and passes through the center of the motor shaft 2s. This achieves a smaller gap between each pair of the circumferentially adjacent cylinders 4. Further, interference is less likely caused between the piston head parts 5h of the two adjacent pistons 5. This allows an even shorter piston rod 5P. Accordingly, an even smaller compressor is realized.

Further, the four pistons 5 each make intake-compression strokes maintaining a ninety-degree phase difference with each other. This balances out force acting on the piston head part 5h of each of the four pistons 5, thus fluctuations in running torque of the motor shaft are prevented. This greatly improves the compression efficiency. Further, intake-exhaust sounds generated from the four compression chambers are balanced out, which results in lower noise and less vibration.

Further, one eccentric shaft 17 is employed to which the four pistons 5 are installed. This allows smaller gaps between the rod parts 5R of the pistons 5 in the direction of the motor shaft 2s. Further, a force generated when one piston 5 shifts from a compression stroke to an intake stroke is efficiently transmitted as a force assisting a motion of another piston 5, thus exhibiting smaller loss in transmission of force. This further improves the compression efficiency.

Further, the casing 3 is provided with the first positioning parts 3B, and the four cylinders 4 are each provided with a second positioning part 4B corresponding to a first positioning part 3B. This allows positioning of the four cylinders 4 with respect to the casing 3 in such a way that the axial center of each of the four cylinders 4 matches the axial center of the piston head part 5h of the corresponding piston 5. Thus, lopsided wear of the seal member 28 is prevented.

The adjust members 34 are each provided between neighboring ones of the piston rod parts 5R of the four pistons 5, in order to adjust the positions of the rod parts. This achieves an ensured match of the axial center of the cylinder 4 and the axial center of the piston head part 5h, thus preventing lopsided wear of the seal member 28.

Further, the main body part 4a and the plane member 4p of each of the four cylinders 4 have an elastic member 4A therebetween. This allows a smaller gap between the cylinder 4 and the piston head part 5h of the corresponding one of the four pistons 5 at a top dead center, merely with torque management of a bolt fastening the main body part 4a and the plane member 4p. This stabilizes performance of the compressor, thus further improving the compression efficiency.

Further, the piston head part 5h of each of the four pistons 5 and the retainer plate 27 have a spacer 30 therebetween. This allows a smaller gap between the cylinder 4 and the piston head part 5h at a top dead center, only with torque management of a bolt fastening the piston head part 5h and the retainer plate 27. This stabilizes performance of the compressor, thus further improving the compression efficiency.

Further, passages between the plurality of cylinders are united by at least one of the shared intake passage 9 and the shared exhaust passage 8. Further, at least one of the shared intake passage 9 and the shared exhaust passage 8 is provided so as to overlap at least one of the axial region 31 extending in the axial direction of the motor shaft 2s and the peripheral region 32 thereof. This prevents a large compressor as a whole due to the shared passage (s). As a result, the passages between a plurality of cylinders are united while avoiding a large compressor.

Further, the present embodiment is provided with the four cylinders 4, the four pistons 4, the four intake passages 6, and the four exhaust passages 7; however, the number of each member is not limited to four as long as it is more than one.

Further, each of the shared intake passage 9 and the shared exhaust passage 8 is an annular passage around the axial region 31. These annular passages are compactly structured, thus easily avoiding a large compressor. Particularly, the annular shared exhaust passage 8 ensures sufficient heat dissipating surface of the fluid, thus improving the compression efficiency.

Further, the annular shared exhaust passage 8 extends two-dimensionally along a plane perpendicular to the axial direction of the motor shaft 2s. This avoids a large compressor due to the shared exhaust passage 8, thus easily ensures a sufficient heat dissipating surface of the fluid in order to improve the compression efficiency.

Further, the bearing support member 10 is provided to the shaft end portion 2t of the motor shaft 2s. The bearing support member 10 has the shared exhaust passage 8 formed therein. This efficient utilization of the member forbearing support and a space surrounding the bearing support allows the passages between among the cylinders to be united, while efficiently avoiding a large compressor.

Further, the four exhaust passages 7 each include a first parallel portion 7f extending in the axial direction of the motor shaft 2s. Thus, the portion in the axial direction of the motor shaft 2s of each of the exhaust passages 7 allows an efficient arrangement of the exhaust passages 7.

Further, the first parallel portions 7f are formed inside the casing 3. Thus, due to the first parallel portions 7f of the exhaust passages 7 provided inside the casing 3, fewer or no additional members such as pipes are necessary for passage formation. This decreases the number of members, and thus a more efficient arrangement of the exhaust passages, while avoiding a large compressor. Further, the casing 3 itself serves as a heat dissipating member. This greatly expands the heat dissipating surface, thus further improving the compression efficiency.

Further, the motor 2 includes the main body part 2b. The shared intake passage 9 and the shared exhaust passage 8 are provided to sandwich the four cylinders 4 with respect to the axial direction of the motor shaft 2s. The shared exhaust passage 8 is provided to the shaft end portion 2t side of the motor shaft 2s. The shared intake passage 9 is provided to the main body part 2b side of the motor shaft 2s. This allows an efficient arrangement of both of the shared intake passage 9a and the shared exhaust passage 8, while avoiding a large compressor. Further, the shared intake passage 9 and the shared exhaust passage 8 are separated. This prevents heat transfer between the shared intake passage 9 and the shared exhaust passage 8, thus further improving the compression efficiency.

Further, the intake passages 6 each include a second parallel portion 6f extending in the axial direction of the motor shaft 2s. This allows an efficient arrangement of the intake passages 6 in the reciprocating compressor 1.

Further, the casing 3 includes the first member 3f and the second member 3s. The exhaust passages 7 each pass through inside the first member 3f. The intake passages 6 each pass through inside the second member 3s. The first member 3f and the second member 3s are separate members. Further, the first member 3f has higher thermal conductivity than the second member 3s. Thus, the intake passages 6 and the exhaust passage 7 are respectively provided inside the second member 3s and the first member 3f. The first member 3f and the second member 3s have different thermal conductivities, which prevents heat of the exhaust passages 7 from transferring to the intake passages 6, thus further improving the compression efficiency. Further in the present embodiment, the first member 3f is made of metal and has high thermal conductivity. This allows efficient dissipation of heat of the fluid, thus further improving the compression efficiency.

Further, the four pistons 5 are provided so that the piston head parts 5h are arranged at ninety-degree intervals. The four pistons 5 are sequentially installed to the one motor shaft 2s, in the motor shaft direction. Thus, the cylinder 4 closest to the main body part 2b of the motor 2 (corresponding to the main body part side piston 5) is farther from a wall composed of the casing 3, the bearing support 10, and the casing cover 15 with respect to the shaft end portion 2t of the motor shaft 2s than the cylinder 4 farthest from the main body part 2b (corresponding to the shaft end portion side piston 5) is from the wall. Thus, the vent 10h in the reciprocating compressor 1 is formed in this space (see FIGS. 1, 2, and 3). Thus, without an additional member, the vent 10h is formed to an appropriate position close to the shared exhaust passage 8 inside the bearing support member 10, where the vent 10h is inconspicuously provided without contributing to enlargement of the size of the compressor.

Further, the exhaust passages are each provided with a divergence passage 7s extending in the direction of gravity, and an adhesive 7A is applied to the exhaust passage. This prevents emission of wear particles of the seal member.

Further, according to the oxygen concentrator 100 of the present embodiment, durability of the reciprocating compressor 1 is improved by cooling inside of the sealed reciprocating compressor 1. The down-sizing and reduction of rotation speed of the cooling fan 323 facilitate power saving and noise suppression of the compressor. Further, a lower internal temperature of the reciprocating compressor 1 restrains a temperature increase in compressed air supplied to the first adsorption vessel 304A and the second adsorption vessel 304B. This prevents lower adsorption efficiency of nitrogen to the adsorbent in the first adsorption vessel 304A and the second adsorption vessel 304B, thus restraining a decrease in oxygen concentration in the condensed oxygen gas.

Further, the nitrogen-containing gas exhausted from the first adsorption vessel 304A and the second adsorption vessel 304B forms the exhaust gas passage X. This improves durability of the seal member 28 of the piston head part 5h which particularly generates high heat.

(Second Embodiment)

The following describes a second embodiment of the reciprocating compressor according to the present invention. Note that the same parts as in the above embodiment will be denoted by the same reference numerals in figures, without descriptions thereof.

Figure 33:
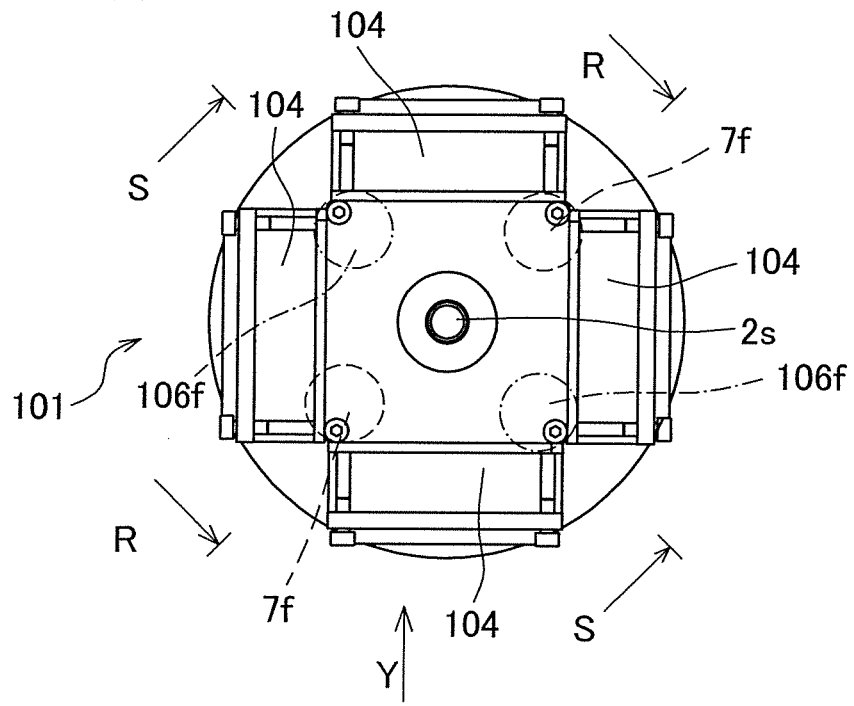
FIG. 33 is a schematic view of a reciprocating compressor according to the second embodiment of the present invention, where (a) is an overhead schematic view, and (b) is a schematic side view on the Y arrow.
Figure 33:
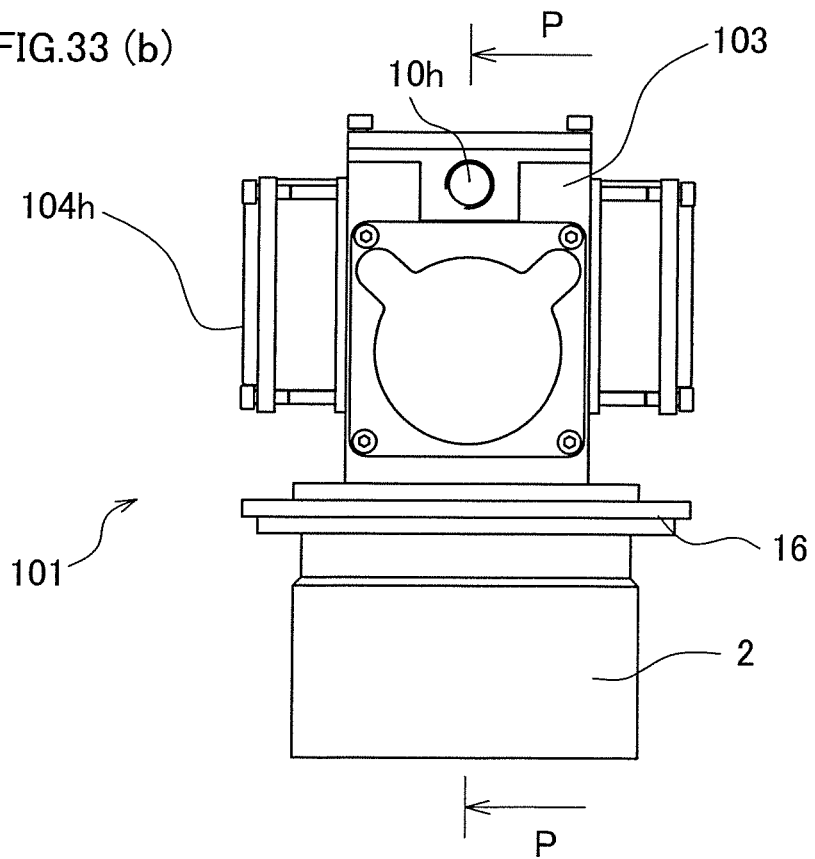

FIG. 33 is a schematic view of a reciprocating compressor according to the second embodiment of the present invention, where (a) is an overhead schematic view, and (b) is a schematic side view on the Y arrow.

Figure 34:
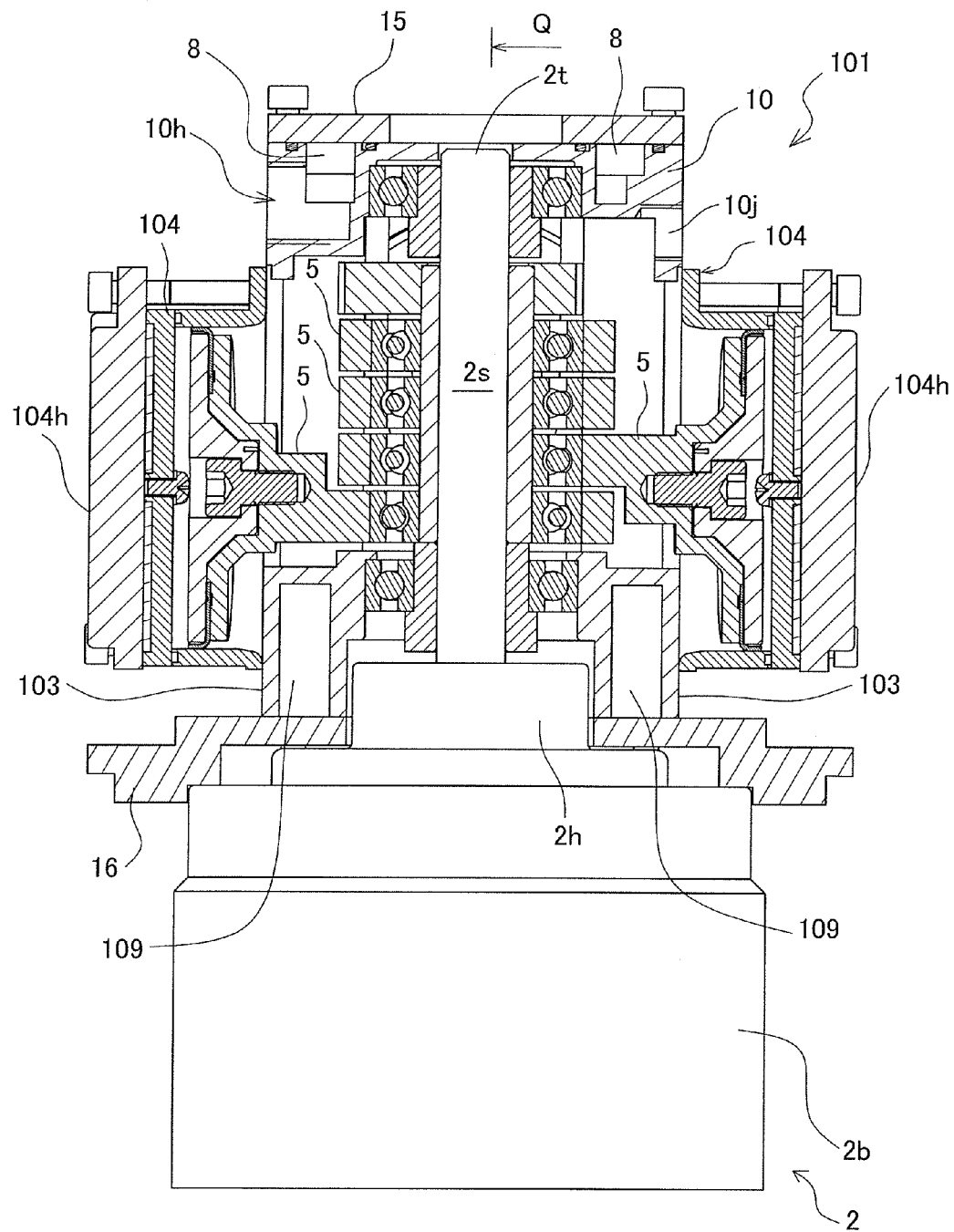
FIG. 34 is a schematic cross-sectional view taken along the P-P line in FIG. 33(b).

FIG. 34 is a schematic cross-sectional view taken along the P-P line in FIG. 33(b).

Figure 35:
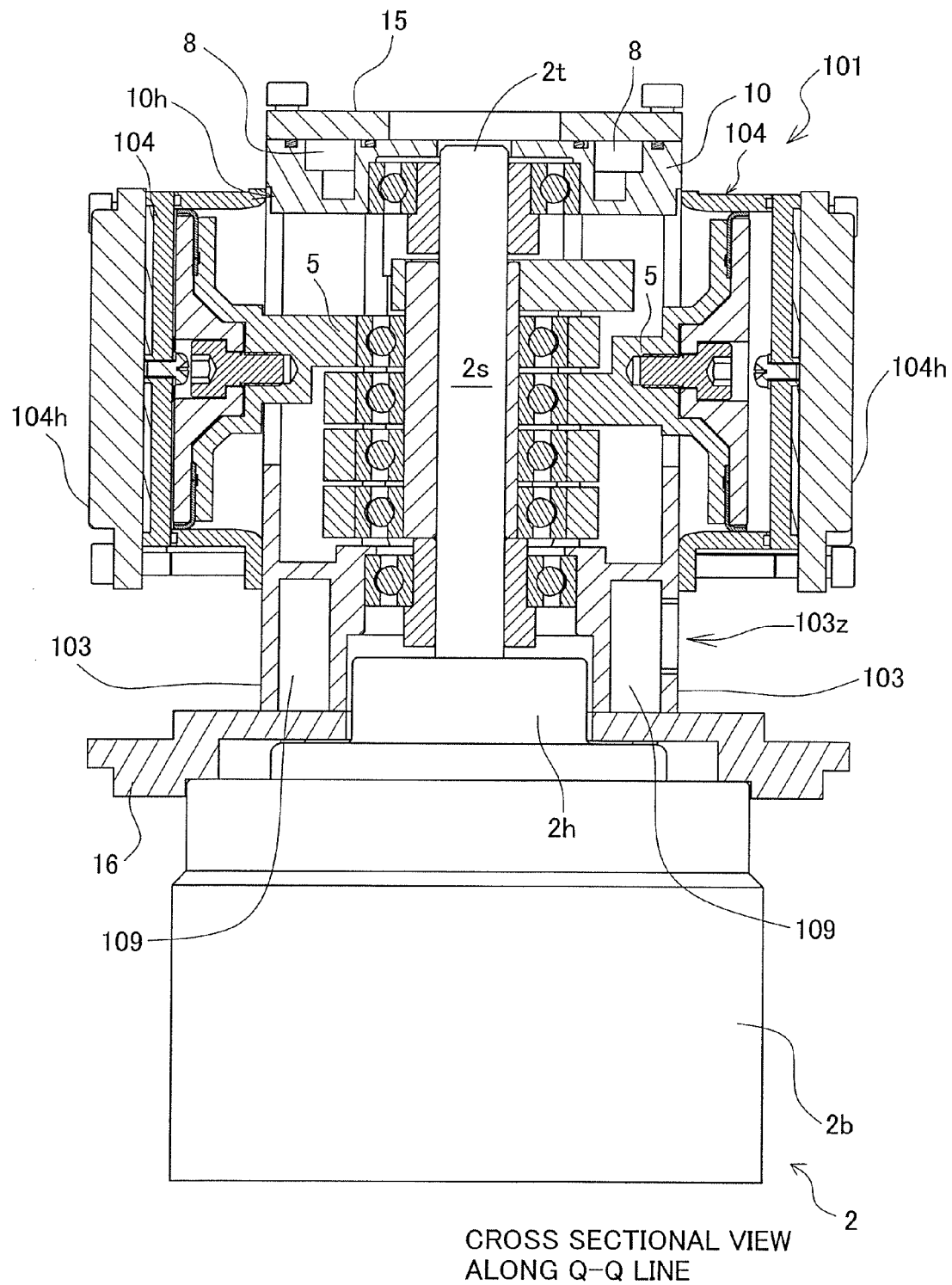
FIG. 35 is a schematic cross-sectional view taken along the Q-Q line in FIG. 34.

FIG. 35 is a schematic cross-sectional view taken along the Q-Q line in FIG. 34.

Figure 36:
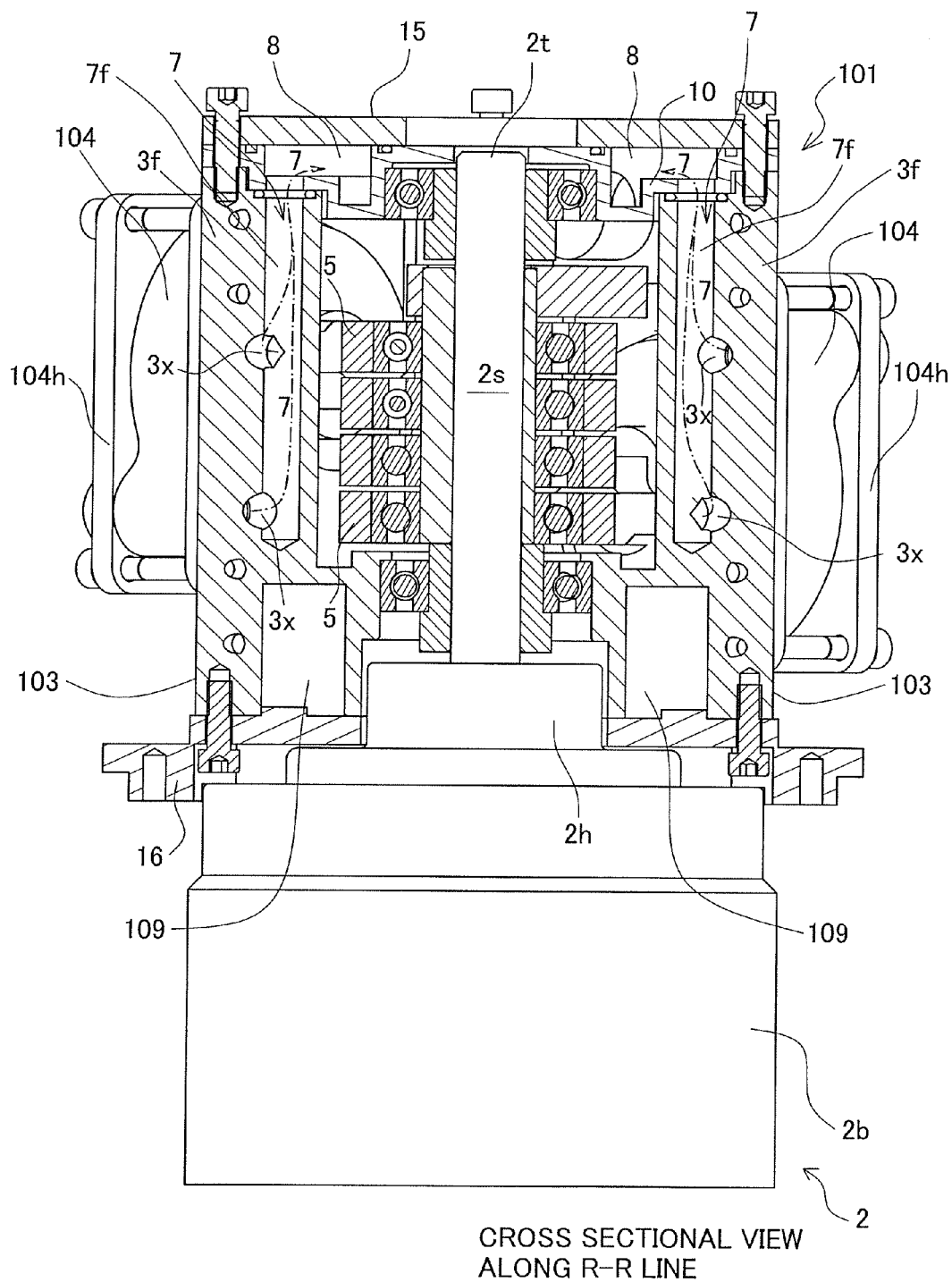
FIG. 36 is a schematic cross-sectional view taken along the R-R line in FIG. 33(a).

FIG. 36 is a schematic cross-sectional view taken along the R-R line in FIG. 33(a).

Figure 37:
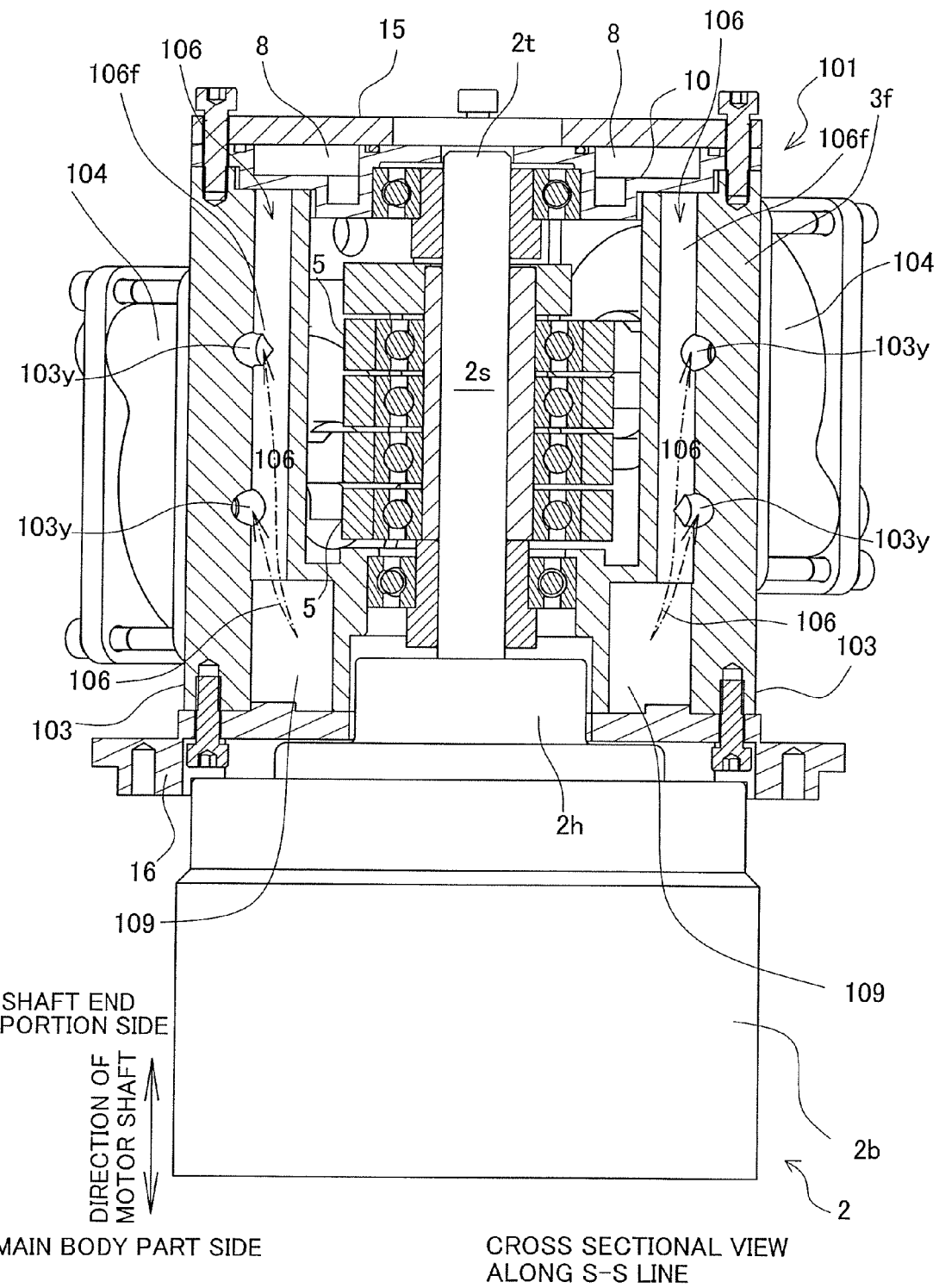
FIG. 37 is a schematic cross-sectional view taken along the S-S line in FIG. 33(a).

FIG. 37 is a schematic cross-sectional view taken along the S-S line in FIG. 33(a).

The reciprocating compressor 101 according to the present embodiment is provided with first parallel portions 7*f* and second parallel portions 106*f* inside of a metallic member corresponding to the first member 3*f*. As a casing 103 of the present embodiment is differently arranged in comparison to the previous embodiment, a cylinder 104 is also differently arranged in terms of, for example, the positions of through holes (illustration omitted).

The exhaust passages 7 in the reciprocating compressor 101 each include a first parallel portion 7*f* extending in an axial direction of a motor shaft 2*s* (same as the above embodiment. See FIGS. 33(*a*) and 36). Further, the intake passages 106 each include a second parallel portion 106*f* extending in the axial direction of the motor shaft 2*s* (see FIGS. 33(*a*) and 37).

A pair of first parallel portions 7*f* and a pair of second parallel portions 106*f* are formed inside of the casing 103. The pair of first parallel portions 7*f* face each other across the motor shaft 2*s* (see the dashed line in FIG. 33(*a*)). The pair of second parallel portions 106*f* face each other across the motor shaft 2*s* (see the dot and dashed line in FIG. 33(*a*)). The pair of first parallel portions 7*f* and the pair of second parallel portions 106*f* are disposed so that a first parallel portion 7*f* is adjacent to a second parallel portion 106*f* (see FIGS. 33(*a*), 34, and 36).

Unlike the above embodiment, the casing 103 corresponding to the first member of the above embodiment is provided with four intake exits 103*y* (see FIG. 37). A shared intake passage 109 is provided in the casing 103. The shared intake passage 109 is provided closer to a main body part 2*b* than pistons 5 are to the main body part 2*b*, with respect to a motor shaft direction (see FIG. 34). An inlet 103*z* of the shared intake passage 109 is formed on an external wall of the casing 103 (see FIG. 35).

The reciprocating compressor 101 constituted as above is the same as the above embodiment in regard to the exhaust passages 7, but differs from the above embodiment in regard to the intake passages 106. The intake passages 106 pass through inside of the casing 103. Specifically, the second parallel portions 106*f* are formed inside of the casing 103. The intake passages 106 are connected to inside of each of the cylinders 104 (compression chamber 4*j*) (see dashed lines illustrating the intake passages 106 in FIG. 37).

Air first flows inside of the casing 103 through the inlet 103*z* provided to the casing 103. The air then flows into the shared intake passage 109 (see FIG. 35). The following describes each of the intake passages 106; i.e., a passage to the inside of the cylinder 104 (compression chamber 4*j*). Inside the casing 103, the shared intake passage 109 continues to the two second parallel portions 106*f*. Air in the shared intake passage 109 is supplied to the two second parallel portions 106*f* (see FIG. 37). The air flown through each of the two second parallel portions 106*f* is supplied to a first room through a through hole (corresponding to the through hole 4*b* of the above embodiment). The air inside the first room is then supplied to the compression chamber 4*j* through the through hole 4*c*. The intake passages 106 are each constituted as described above.

As described above, in the reciprocating compressor 101 of the present embodiment, the exhaust passages 7 each include a first parallel portion 7*f* extending in the axial direction of the motor shaft 2*s*, and the intake passages 106 each include a second parallel portion 106*f* extending in the axial direction of the motor shaft 2*s*. Further, the pair of first parallel portions 7*f* and a pair of second parallel portions 106*f* are formed inside of the casing 103, the pair of first parallel portions 7*f* facing each other across the motor shaft 2*s*, and the pair of second parallel portions 106*f* facing each other across the motor shaft 2*s*. Thus, all of the first parallel portions 7*f* of the exhaust passages 7 and the second parallel portions 106*f* of the intake passages 106 are provided inside the casing 103. This facilitates efficient utilization of the casing 103, thus more efficiently restraining a large compressor while uniting the passages between the cylinders.

(Third Embodiment)

The following describes a third embodiment of the reciprocating compressor according to the present embodiment. Note that the same parts as in the above embodiment(s) will be denoted by the same reference numerals in figures, without descriptions thereof.

Figure 38:
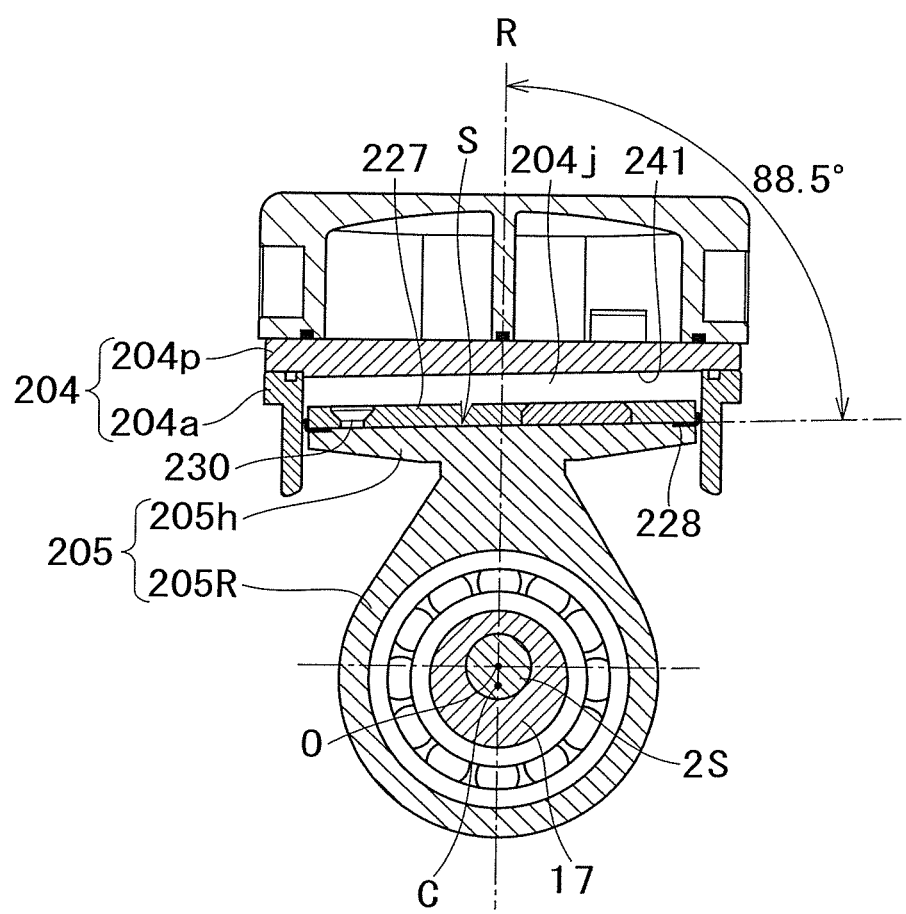
FIG. 38 is a schematic diagram illustrating a reciprocating compressor according to a third embodiment of the present invention.

FIG. 38 is a schematic diagram illustrating a reciprocating compressor according to a third embodiment of the present invention.

Figure 39:
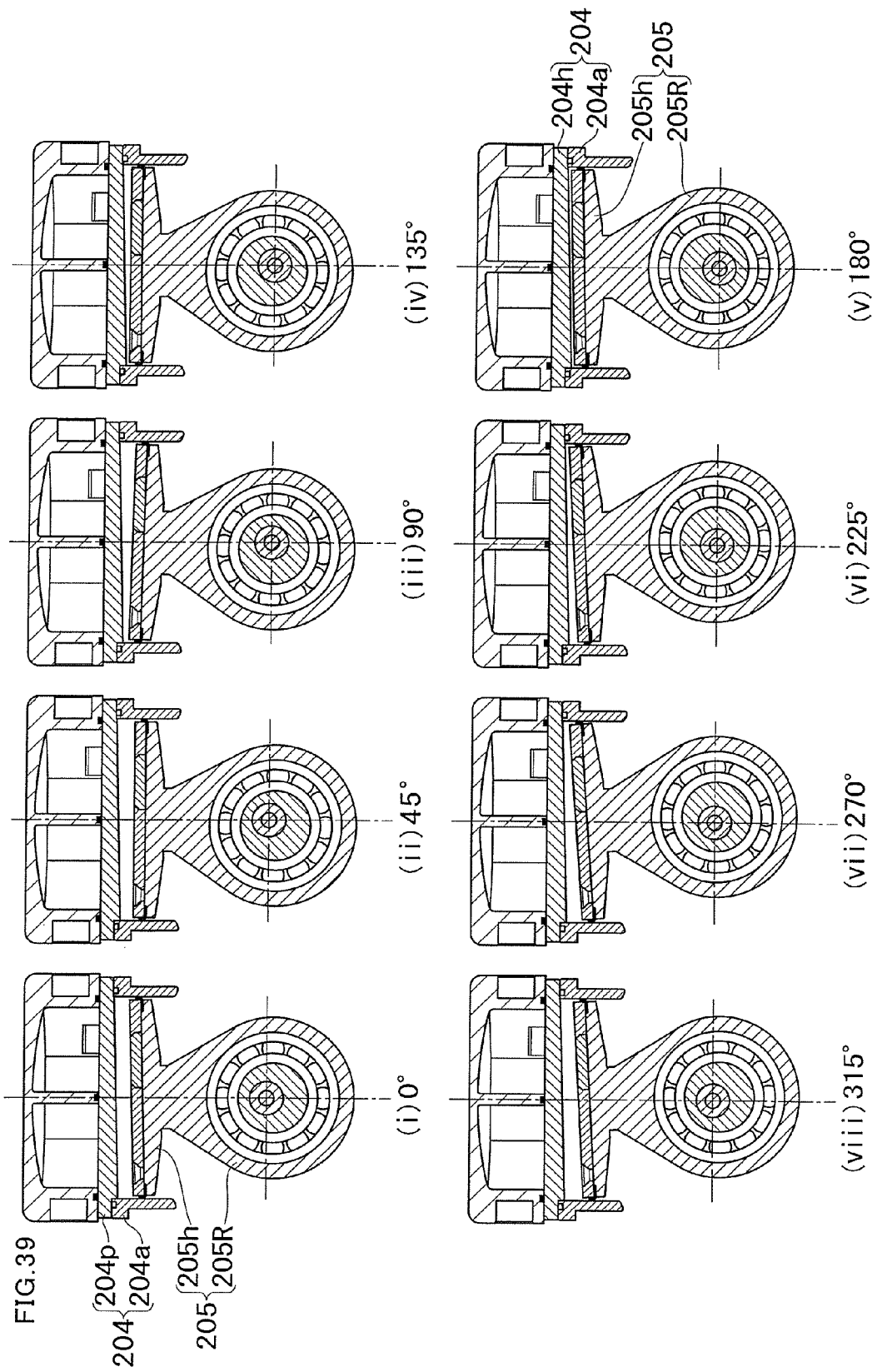
FIG. 39 is an explanatory view of an operation of the embodiment.

FIG. 39 is an explanatory view of an operation of the embodiment.

Figure 40:
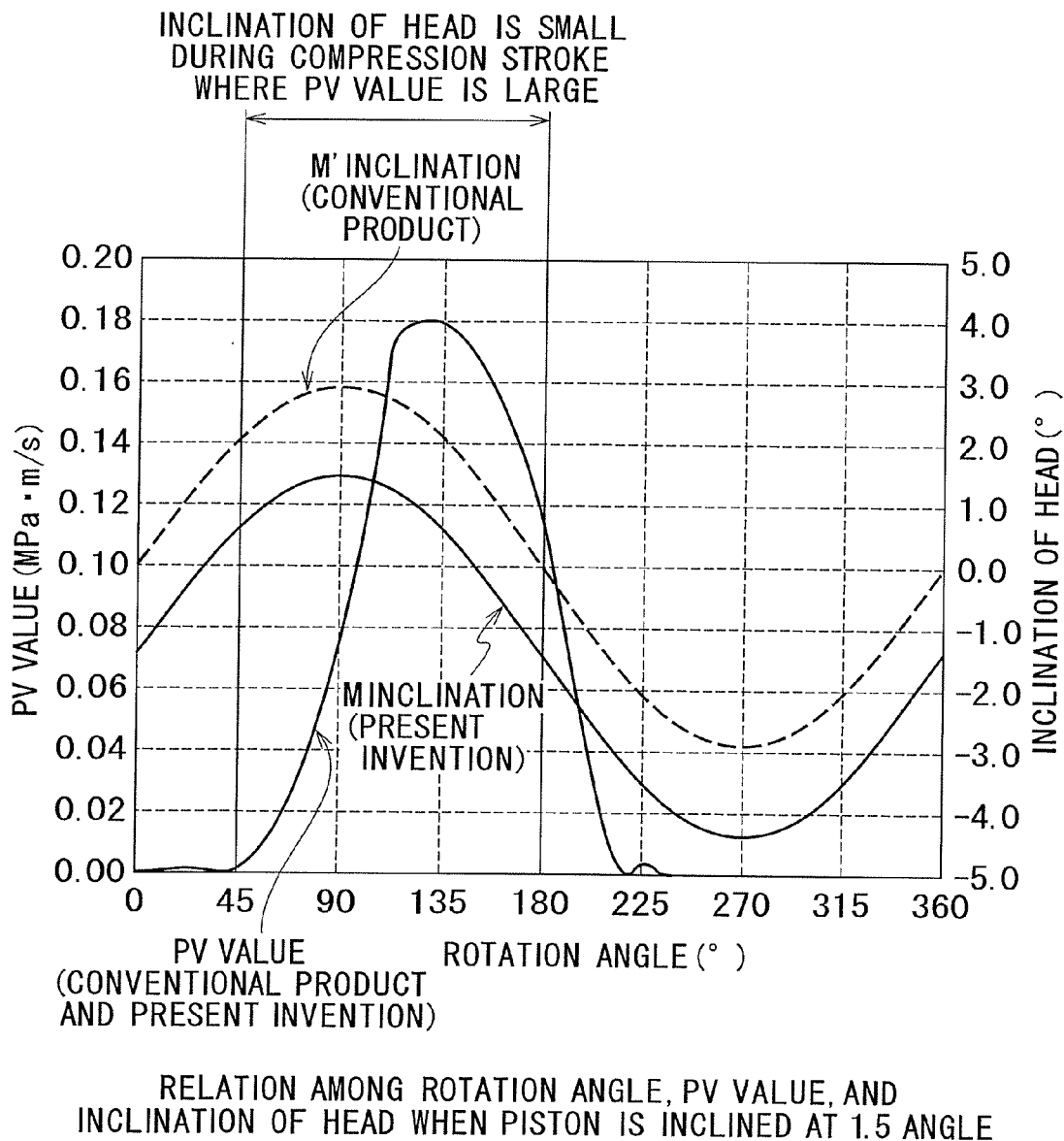
FIG. 40 is a view illustrating a relation among an angle of rotation, a PV value, and an angle of slope of head in the embodiment.

FIG. 40 is a view illustrating a relation among an angle of rotation, a PV value, and an angle of slope of head in the embodiment.

Figure 41:
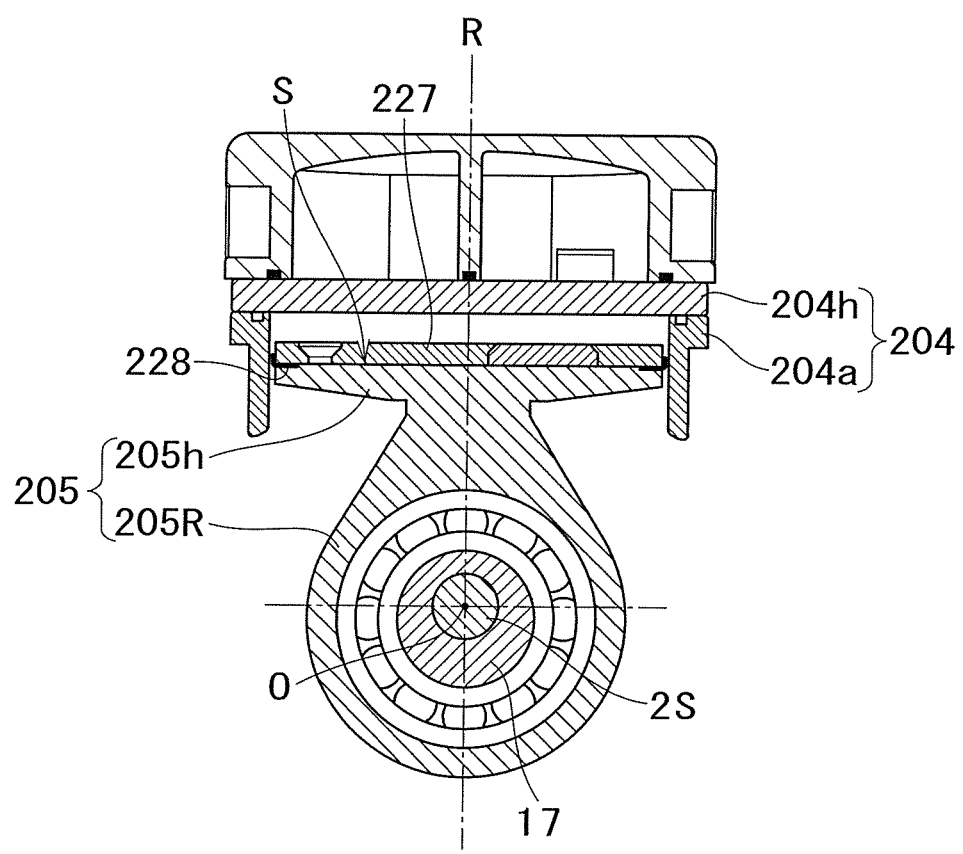
FIG. 41 is a schematic diagram illustrating a known reciprocating compressor.

FIG. 41 is a schematic diagram illustrating a known reciprocating compressor.

In the reciprocating compressor according to the present embodiment, when any one of the four pistons 5 is at the bottom dead center, a seal plane S along a seal member 228 of the piston 5 is out of square with respect to a reference plane R including a center C of an eccentric shaft 17 and a center O of a motor shaft 2*s*, as illustrated in FIG. 38.

As illustrated in FIG. 38, a cylinder 204 includes a main body part 204*a* and a plane member 204*p*. The plane member 204*p* is fixed to the main body part 204*a* to form a compression chamber 204*j*. Between the main body part 204*a* and the plane member 204*p* of the cylinder 204 is sealed by the elastic member 204A. The cylinder 204 is fixed to the casing (not illustrated).

The cylinder 204 is provided with a piston 205 therein. The piston 205 has a piston head part 205*h* and a rod part 205R formed integrally. The piston head part 205*h* is swingable and reciprocal within the cylinder 204. A ceiling sealing surface S of the piston head part 205*h* of the piston 205; i.e., the seal plane S has a part of the annular seal member 228 placed thereon. The part of the seal member 228 is sandwiched and fixed by a ceiling surface S of the piston head part 205*h* and a retainer plate 227. Other part of the seal member 228 protrudes from the piston head part 205*h* and the retainer plate 227 to contact an inner surface of the cylinder 204, in order to perform a sealing function. The retainer plate 227 is fixed to the piston head part 205*h* by a screw 230.

As illustrated in FIG. 38, when the piston 205 is at the bottom dead center, the ceiling surface S of the piston head part 205*h* of the piston 205; i.e., the seal plane S along the annular seal member 228 is out of square with respect to the reference plane R including the center O of the motor shaft 2*s* and the center C of the eccentric shaft 17. More specifically, when the piston 205 is at the bottom dead center, the ceiling surface S of the piston head part 205*h* of the piston 205; i.e., the seal plane S along the annular seal member 228 forms an 88.5-degree angle with the reference plane R. In other words, when the piston 205 is at the bottom dead center, the ceiling surface S (seal plane S) of the piston head part 205*h* is inclined at a 1.5-degree angle with respect to a plane perpendicular to the reference plane R, and is inclined at a 1.5-degree angle with respect to a central axis of the cylinder 204. Thus, when an angle of rotation of the motor shaft 2*s* is substantially at 149 degrees close to 135 degrees which results in a maximum PV value, an angle of slope with respect to a plane perpendicular to the reference plane R; i.e., an angle of slope of the ceiling surface S of the piston head part 205h of the piston 205 with respect to the plane perpendicular to the reference plane R is zero, as illustrated in FIG. 40.

When the piston 205 is at the bottom dead center or the top dead center, a ceiling surface 241 of the compression chamber 204j of the cylinder 204 is parallel to the ceiling surface S of the piston head part 205h of the piston 205. In other words, the ceiling surface 241 of a compression chamber 22 of the cylinder 204 is inclined at a 1.5-degree angle with respect to a plane perpendicular to the central axis of the cylinder 204. Thus, no dead space is formed between the ceiling surface 241 of the compression chamber 22 of the cylinder 204 and an upper surface of the retainer plate 227 when the piston 205 is at the top dead center. This increases compression efficiency.

The following describes an operation of the reciprocating compressor constituted as described above, with reference to FIGS. 38, 39, and 40.

In FIG. 40, the horizontal axis represents the angle of rotation of the motor shaft 2s. The right vertical axis represents the angle of slope of the ceiling surface S of the piston head part 205h of the piston 205 with respect to a plane perpendicular to the central axis of the cylinder 204. The left vertical axis represents the PV value.

In the reciprocating compressor, when the motor 2 drives the motor shaft 2s to rotate clockwise from a state illustrated in FIG. 38, the piston 205 oscillates while reciprocating as illustrated by (i) to (viii) in FIG. 39, to admit and compress a gas such as air.

As indicated by the curve M in FIG. 40, the ceiling surface S of the piston head part 205h of the piston 205; i.e., the seal surface S along the annular seal member 228 is inclined at a 1.5-degree angle with respect to a plane perpendicular to the reference plane R (plane perpendicular to the central axis of the cylinder 204) at the bottom dead center (0-degree angle of rotation of the motor shaft 2s) or the top dead center (180-degree angle of rotation of the motor shaft 2s). As the motor shaft 2s rotates, the angle of slope (angle of slope of head) of the ceiling surface S of the piston head part 205h of the piston 205; i.e., the seal surface S along the annular seal member 228 changes, as illustrated in FIGS. 39 and 40.

As the curve M in FIG. 40 illustrates, the angle of slope of the ceiling surface S of the piston head part 205h of the piston 205; i.e., the absolute value of the angle of slope of the seal plane S is smaller in the compression stroke and larger in the intake stroke than an angle of slope of the ceiling surface S of the piston head part 205h of a standard piston 205 indicated by the curve M' illustrated in FIG. 41.

Thus, in the compression stroke where the PV value is large and thus a high load is imposed on the sealing member 228, the absolute value of the angle of slope of the seal surface S (curve M in FIG. 40) of the present embodiment is smaller than the absolute value of the angle of slope of the ceiling surface S (curve M' in FIG. 49) of the conventional example illustrated in FIG. 41. This causes the seal member 228 to substantially uniformly contact the inner surface of the cylinder 204. Therefore, lopsided wear of the seal member 228 is prevented and thus a longer-life seal member 228 is realized. Further, a gap between the cylinder 204 and the seal member 228 is reduced, which prevents air leakage thus improves the compression efficiency.

Compared to during a compression stroke, the PV value is generally small and the load imposed on the seal member 228 is relatively small during an intake stroke. Thus, a large angle of slope of the ceiling surface S of the head part 205h of the piston 205; i.e., a large absolute value of the angle of rotation of the seal plane S barely causes harm such as localized wear of the seal member 228 or air leakage.

Further in the above embodiment, the absolute value of an angle of rotation of the seal plane S with respect to a plane perpendicular to the reference plane R is smaller during a compression stroke than during an intake stroke. This allows substantially uniform contact of the seal member 228 with the inner surface of the cylinder when a large load is imposed on the seal member 228. Therefore, lopsided wear of the seal member 228 is prevented and thus a longer-life seal member 228 is realized. Further, a gap between the cylinder 204 and the seal member 228 is reduced, which prevents air leakage thus improves the compression efficiency.

Further in the above embodiment, the ceiling surface S of the piston head part 205h of the piston 205; i.e., the seal plane S is perpendicular to the reference plane R when the angle of rotation of the motor shaft 2s is at around 135 degrees with which the PV value of the seal member is maximized, and the seal plane S is not inclined with respect to the central axis of the cylinder 204 when a maximum load is imposed on the seal member 228. This prevents localized wear of the seal member 228 and thus realizes a long-life seal member. Further, air leakage is prevented, thus improving the compression efficiency.

Further in the above embodiment, the seal member 228 is attached to the ceiling surface S of the piston head part 205h of the piston 205 by the retainer plane 227. Thus, adjustment of the angle of slope of the ceiling surface S of the piston head part 205h allows the inclination of the seal plane S to be easily set.

Further in the present invention, the ceiling surface S of the piston head part 205h of the piston 205 is parallel to the ceiling surface 241 of the compression chamber 204j of the cylinder 204. This reduces a dead space between the upper surface of the retainer plate 227 and the ceiling surface 241 of the compression chamber 204j of the cylinder 204. The compression efficiency is thus improved.

Although the embodiments of the present invention have been described with reference to the figures, it should be understood that specific structures are not limited to the embodiments. The scope of the present invention is indicated not by the above description of the embodiments, but by the claims. Further, the scope of the present invention includes connotations equal to the scope of the claims and every change within the scope of the claims.

The above embodiments, for instance, are each provided with both a shared intake passage and a shared exhaust passage. However, at least one of a shared intake passage and a shared exhaust passage is required. Thus, one of a shared intake passage and a shared exhaust passage may be absent.

Further in the above embodiments, the exhaust passages each include a first parallel portion extending in the axial direction of the motor shaft, and the intake passages each include a second parallel portion extending in the axial direction of the motor shaft. Nevertheless, the intake passages and the exhaust passages are not required to include the first parallel portions and the second parallel portions, respectively. Further, only one of the first parallel portions and the second parallel portions may be formed in the exhaust passages and the intake passages.

Further in the above embodiments, the piston head part 5h and the retainer plate 27 fastened by a bolt have the seal member 28 and the spacer 30 therebetween; however, when the seal member 28 serves as the spacer 30, the piston head par 5h and the retainer plate 27 may only have the seal member 28 therebetween.

Further in the above embodiments, the side portion of the bearing support member 10 and the side portion of the casing 3 are circumferentially adjacent with respect to the motor shaft 2s, the side portion of the bearing support member 10 and the side portion of the casing 3 respectively being provided with the cooling inlet 10j and the cooling vent 3j. Nevertheless, the side portions of the bearing support member 10 and the casing 3 may be provided in any positional relation with respect to the motor shaft 2s. For example, the side portion of the bearing support member 10 and the side portion of the casing 3 may oppose each other across the motor shaft 2s.

Further, in the above embodiments, the cooling inlet 10j is provided on a side portion of the bearing support member 10. The cooling inlet, however, may be formed at any position of the reciprocating compressor as long as the cooling inlet 10j is able to admit a cooling medium inside the exhaust gas passage Z. Further, the cooling inlet 3j is formed to a side portion of the casing 3. The cooling inlet 3j, however, may be formed at any position of the reciprocating compressor, as long as the cooling inlet 3j is able to exhaust a cooling medium from the exhaust gas passage Z.

Further in the above embodiments, the fluid to be admitted to the reciprocating compressor is air; however, the reciprocating compressor may admit and compress a gas fluid other than air (e.g., nitrogen, oxygen, carbon dioxide, a cooling medium, or the like).

Further in the third embodiment, the seal member 228 is fixed to the piston head part 205h of the piston 205 by the retainer plate 227. However, a groove may be formed to a not-illustrated piston head part of a piston and an annular seal member may fit into the groove without the retainer plate, the groove being along a surface inclined with respect to a plane perpendicular to the central axis of the cylinder. In short, it is merely required that the seal plane along the annular seal member is inclined with respect to a plane perpendicular to the axial center of the cylinder when the piston is at the top dead center or the bottom dead center.

Further in the third embodiment, the angle of slope of the ceiling surface S of the piston head part 205h of the piston 205 with respect to a plane perpendicular to the central axis of the cylinder 204 is 1.5 degrees. However, the angle of slope is, of course, not limited to 1.5 degrees.

Although not illustrated, a crankpin of a crankshaft may be employed as the eccentric shaft in the above embodiments.

Further in the above fourth embodiment, the oxygen concentrator 100 including a first and a second two adsorption vessels is described. However, the present invention may be applied to an oxygen concentrator 100 having one, or three or more adsorption vessels. Nevertheless, at least two adsorption vessels serving as adsorption containers alternately repeat switching between adsorption and desorption, and thus exhausts a gas which contains adsorbed nitrogen. This efficiently cools the interior of the sealed reciprocating compressor.

Further in the above fourth embodiment, the oxygen concentrator 100 is described, which oxygen concentrator 100 utilized in home oxygen therapy for a patient with respiratory disorders or the like. However, utilization of the oxygen concentrator 100 is not limited to this, but the present invention may be employed for every field where highly-concentrated oxygen is to be provided.

INDUSTRIAL APPLICABILITY

Utilization of the present invention realizes a smaller and light reciprocating compressor with higher efficiency and longer life time, producing lower noise and less vibration.

What is claimed is:

1. A reciprocating compressor comprising:
   a motor having a motor shaft;
   a casing accommodating the motor shaft;
   four cylinders provided in perpendicular directions relative to an axial direction of the motor shaft, the four cylinders being a first cylinder, a second cylinder, a third cylinder and a fourth cylinder; and
   four pistons, with each piston having
      a piston head part fitted into one of the four cylinders in a reciprocal fashion, and
      a rod part formed integrally with the piston head part, the rod part being rotatably mounted to an eccentric shaft that is fixed to the motor shaft,
   a plurality of exhaust passages each connected to inside of one of the four cylinders;
   a plurality of intake passages each connected to inside of one of the four cylinders,
   two of the exhaust passages respectively connected to the first cylinder and the second cylinder adjacent to each other share a first conduit formed inside the casing parallel to the motor shaft and disposed between the first cylinder and a second cylinder,
   two of the exhaust passages respectively connected to the third cylinder and the fourth cylinder adjacent to each other share another first conduit formed inside the casing parallel to the motor shaft and disposed between the third cylinder and the fourth cylinder,
   two of the intake passage respectively connected to the second cylinder and the third cylinder adjacent to each other share a second conduit formed inside the casing parallel to the motor shaft and disposed between the second cylinder and the third cylinder, and
   two of the intake passages respectively connected to the first cylinder and the fourth cylinder adjacent to each other share another second conduit formed inside the casing parallel to the motor shaft and disposed between the first cylinder and the fourth cylinder.

2. The reciprocating compressor according to claim 1, wherein
   two of the four cylinders are disposed along a first straight line passing through a center of the motor shaft, and
   two of the four cylinders are disposed along a second straight line which is perpendicular to the first straight line, the second straight line also passing through the center of the motor shaft.

3. The reciprocating compressor according to claim 1, wherein
   the piston head parts of the four pistons are arranged to make intake-compression strokes while maintaining a ninety-degree phase difference relative to each other.

4. The reciprocating compressor according to claim 1, wherein
   each of the rod parts of the four pistons is rotatably mounted to a single, common eccentric shaft that is fixed to the motor shaft.

5. The reciprocating compressor according to claim 1, wherein
   the casing is provided with a plurality of first positioning parts,
   each of the four cylinders is provided with a second positioning part disposed so as to correspond to one of the first positioning parts, and
   each of the four cylinders is positioned by the second positioning part and a corresponding one of the first positioning parts so as to align an axial center of the cylinder and an axial center of the piston head part of the piston.

6. The reciprocating compressor according to claim 1, further comprising
a plurality of adjust members, with each adjust member being provided between neighboring ones of the rod parts of the pistons in an axial direction of the motor shaft, each of which adjust members adjusts a position of a rod part.

7. The reciprocating compressor according to claim 1, wherein
each of the four cylinders includes:
a cylindrical main body part provided in an axial direction of the cylinder; and
a sheet plane member fixed to an end of the main body part by a bolt, and wherein
the main body part and the plane member have an elastic member provided therebetween.

8. The reciprocating compressor according to claim 1, wherein
each piston head part has a retaining plate fixed to the piston lead part by a bolt with an elastic spacer provided therebetween.

9. The reciprocating compressor according to claim 1, further comprising:
at least one of
a shared intake passage uniting the plurality of intake passages, and
a shared exhaust passage uniting the plurality of exhaust passages,
the at least one of the shared intake passage and the shared exhaust passage overlapping at least one of an axial region and a peripheral region thereof, with the axial region extending in the axial direction of the motor shaft.

10. The reciprocating compressor according to claim 9, wherein
the at least one of the shared intake passage and the shared exhaust passage is an annular passage extending around the axial region.

11. The reciprocating compressor according to claim 10, wherein
the shared exhaust passage is the at least one of the shared intake passage and the shared exhaust passage, and the shared exhaust passage extends two-dimensionally along a plane perpendicular to the axial direction of the motor shaft.

12. The reciprocating compressor according to claim 10, further comprising:
a bearing support member provided on a shaft end portion of the motor shaft, the bearing support member being provided with the at least one of the shared exhaust passage and the shared intake passage.

13. The reciprocating compressor according to claim 9, wherein
the first parallel portion extends in the axial direction of the motor shaft.

14. The reciprocating compressor according to claim 13, wherein
each parallel portion is formed inside the casing.

15. The reciprocating compressor according to claim 9, wherein
the motor includes a main body part,
the reciprocating compressor includes both the shared intake passage and the shared exhaust passage, which are arranged to sandwich the four cylinders therebetween in the axial direction of the motor shaft, and
one of the shared intake passage and the shared exhaust passage is disposed on a shaft end portion side of the motor shaft, and the other of the shared intake passage and the shared exhaust passage is disposed on a main body part side of the motor shaft.

16. The reciprocating compressor according to claim 9, wherein
the second parallel portion extends in the axial direction of the motor shaft.

17. The reciprocating compressor according to claim 9, wherein
the casing includes a first member and a second member,
each exhaust passage passes through the first member,
each intake passage passes through the second member, and
the first member and the second member are separate parts, with the first member having higher thermal conductivity than the second member.

18. The reciprocating compressor according to claim 9, wherein
each exhaust passage is provided with an adhesive.

19. The reciprocating compressor according to claim 1, wherein
each of the piston head parts has a seal member attached thereto, and
the piston head parts and the seal members are arranged such that a seal plane along the seal member of each piston is out of square with respect to a reference plane including a center of the motor shaft and a center of the eccentric shaft when each piston is at a bottom dead center position.

20. The reciprocating compressor according to claim 19, wherein
the piston head parts and the seal members are further arranged such that a sealing surface of each piston head part is out of square with respect to the reference plane when each piston is at the bottom dead center position, the sealing surfaces serving as the sealing planes of the seal members.

21. The reciprocating compressor according to claim 19, wherein
the piston head parts and the seal members are further arranged such that an angle formed between the seal plane of each piston and the reference plane at an opposite side to a travel direction of a center of the eccentric shaft is acute with respect to the reference plane when each piston is at the bottom dead center position.

22. The reciprocating compressor according to claim 20, wherein
part of each seal member is sandwiched and fixed between the sealing surface of one of the piston head parts and a retainer plate.

23. The reciprocating compressor according to claim 20, wherein
the piston head parts and the seal members are further arranged such that e sealing surface of each piston head part is substantially parallel to a compression chamber of the one of the four cylinders in which each piston head part is fitted when each piston is at a top dead center position.

24. The reciprocating compressor according to claim 19, wherein
the piston head parts and the seal members are further arranged such that an absolute value of an angle of slope of each seal plane with respect to a plane perpendicular to the reference plane is smaller during a compression stroke than during an intake stroke.

25. The reciprocating compressor according to claim 19, wherein
the piston head parts and the seal members are further arranged such that each seal plane is perpendicular to the reference plane when an angle of rotation of the motor shaft is at around an angle with which a PV value of the seal member is maximized.

26. The reciprocating compressor according to claim 1, further comprising:
an exhaust gas passage provided inside of at least one of the casing and the four cylinders;
a cooling inlet configured to admit a cooling medium into the exhaust passage; and
a cooling vent configured to exhaust the cooling medium from the exhaust gas passage.

27. An oxygen concentrator including the reciprocating compressor according to claim 26, the oxygen concentrator further comprising:
an adsorption container configured to admit air compressed by the reciprocating compressor, the adsorption container containing an adsorbent which selectively adsorbs nitrogen;
a condensed oxygen gas extraction unit configured to extract condensed oxygen gas from the adsorption container;
an oxygen tank configured to store the condensed oxygen gas extracted from the adsorption container by the condensed oxygen gas extraction unit; and
a gas exhaust member configured to exhaust a nitrogen containing gas desorbed from the adsorbent by reducing pressure of the adsorption container,
the cooling medium being the nitrogen-containing gas exhausted from the adsorption container by the gas exhaust member.

* * * * *